(12) United States Patent
Kumar et al.

(10) Patent No.: US 12,054,463 B2
(45) Date of Patent: Aug. 6, 2024

(54) RADIOLABELED MICROTUBULE IMAGING COMPOUNDS AND USES THEREOF

(71) Applicant: The Trustees of Columbia University in the City of New York, New York, NY (US)

(72) Inventors: Dileep Kumar, New York, NY (US); J. John Mann, New York, NY (US); Akiva Mintz, New York, NY (US); Kiran Kumar Solingapuram Sai, Winston Salem, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 16/646,630

(22) PCT Filed: Oct. 30, 2018

(86) PCT No.: PCT/US2018/058187
§ 371 (c)(1),
(2) Date: Mar. 12, 2020

(87) PCT Pub. No.: WO2019/089575
PCT Pub. Date: May 9, 2019

(65) Prior Publication Data
US 2020/0290976 A1 Sep. 17, 2020

Related U.S. Application Data

(60) Provisional application No. 62/578,903, filed on Oct. 30, 2017.

(51) Int. Cl.
| | | |
|---|---|---|
| C07D 239/94 | (2006.01) | |
| A61K 51/04 | (2006.01) | |
| C07B 59/00 | (2006.01) | |
| C07D 401/04 | (2006.01) | |
| C07D 401/12 | (2006.01) | |
| C07D 403/04 | (2006.01) | |
| C07D 471/04 | (2006.01) | |
| C07D 487/04 | (2006.01) | |
| C07D 491/04 | (2006.01) | |

(52) U.S. Cl.
CPC ........ *C07D 239/94* (2013.01); *A61K 51/0459* (2013.01); *C07B 59/002* (2013.01); *C07D 401/04* (2013.01); *C07D 401/12* (2013.01); *C07D 403/04* (2013.01); *C07D 471/04* (2013.01); *C07D 487/04* (2013.01); *C07D 491/04* (2013.01)

(58) Field of Classification Search
CPC .. C07D 239/94; C07D 401/04; C07D 401/12; C07D 403/04; C07D 471/04; C07D 487/04; C07D 491/04; A61K 51/0459; C07B 59/002

USPC ........................................................ 424/9.1
See application file for complete search history.

(56) References Cited

U.S. PATENT DOCUMENTS

| 3,985,749 A | 10/1976 | Foster |
| 2011/0300132 A1 | 12/2011 | Tung et al. |
| 2014/0235633 A1 | 8/2014 | Li et al. |

OTHER PUBLICATIONS

Kniess et al. Med. Chem. Commun. 2015, 6, 1714-1754. (Year: 2015).*
Ravert et al. J Label Compd Radiopharm 2002, 45, 471-477. (Year: 2002).*
Farde et al. TINS, 19, 1996, 211-214. (Year: 1996).*
"Pubchem CID 5287565" Create Date: Mar. 26, 2005 (Mar. 26, 2005) Date Accessed: Feb. 18, 2019 (Feb. 18, 2019).
"Pubchem CID 9898839" Create Date: Oct. 25, 2006 (Oct. 25, 2006) Date Accessed: Feb. 18, 2019 (Feb. 18, 2019).
"Pubchem CID 71543088" Create Date: Jun. 11, 2013 (Jun. 11, 2013) Date Accessed: Feb. 18, 2019 (Feb. 18, 2019).
"Pubchem CID 71543176" Create Date: Jun. 11, 2013 (Jun. 11, 2013) Date Accessed: Feb. 18, 2019 (Feb. 18, 2019).
"Pubchem CID 118729850" Create Date: Mar. 8, 2016 (Mar. 8, 2016) Date Accessed: Feb. 18, 2019 (Feb. 18, 2019).
International Search Report and Written Opinion in International PCT application PCT/US18/58187, dated Mar. 7, 2019.
Harada et al. Characterization of the radiolabeled metabolite of tau PET tracer 18F-THK5351, Eur J Nucl Med Mal Imaging. 2016; 43(12): 2211-2218. Abstract.
Bickel, How to Measure Drug Transport across the Blood-Brain Barrier, U. NeuroRx. 2005; 2(1): 15-26.
Jordan et al., Microtubules as a Target for Anticancer Drugs, Nature Reviews Cancer 4, 253-265 (2004).
Van der Veldt AA, Lammertsma AA. In vivo imaging as a pharmacodynamic marker. Clin Cancer Res. 2014; 20(10): 2569-77.
Pike VW. PET Radiotracers: crossing the blood-brain barrier and surviving metabolism, Trends Pharmacol Sci. 2009; 30(8): 431-440.
Sirisoma et al. Discovery of N-( 4-methoxyphenyl)-N,2-dimethylquinazolin-4-amine, a potent apoptosis inducer and efficacious anticancer agent with high blood brain barrier penetration. J Med Chem. 2009; 52(8):2 341-51.
Kasibhatla et al. MPC-6827: a small-molecule inhibitor of microtubule formation that is not a substrate for multidrug resistance pumps. Cancer Res. 2007; 67(12): 5865-71.

(Continued)

*Primary Examiner* — Michael G. Hartley
*Assistant Examiner* — Sean R Donohue
(74) *Attorney, Agent, or Firm* — Leason Ellis LLP

(57) ABSTRACT

The present disclosure relates to radiolabeled compounds and methods of uses for diagnosis, monitoring, and treatment of various degenerative neurological disorders, neuropsychiatric disorders, brain injuries, vascular diseases, and cancers. Radiolabled compounds for imaging of microtubules or microtubules and other targets using positron-emission tomography (PET) are specifically disclosed.

4 Claims, 14 Drawing Sheets

(56) References Cited

OTHER PUBLICATIONS

Tsimberidou et al. Phase I clinical trial of MPC-6827 (Azixa), a microtubule destabilizing agent, in patients with advanced cancer. Mal Cancer Ther. 2010; 9(12): 3410-9.

Grossmann et al. Phase I trial of verubulin (MPC-6827) plus carboplatin in patients with relapsed glioblastoma multiforme. J Neurooncol. 2012; 10(2): 257-64. Abstract.

Devambatla et al. Design, Synthesis, and Preclinical Evaluation of 4-Substituted-5-methylfuro[2,3-d] pyrimidines as Microtubule Targeting Agents That Are Effective against Multidrug Resistant Cancer Cells. J Med Chem. 2016; 59(12): 5752-65.

Wang et al. Optimization of 4-(Ncycloamino) phenylquinazolines as a novel class of tubulin-polymerization inhibitors targeting the colchicine site. J Med Chem. 2014; 57(4): 1390-402.

Guan et al. WX-132-18B, a novel microtubule inhibitor, exhibits promising anti-tumor effects, Oncotarget. May 9, 2017. doi: 10.18632/oncotarget.I 7710.

Wilson et al., An admonition when measuring the lipophilicity of radiotracers using counting techniques. Applied Radiation and Isotopes, 2001, 54: 203-208. Abstract.

Kitange et al. Evaluation of mgmt promoter methylation status and correlation with temozolomide response in orthotopic glioblastoma xenograft model. J Neuro Oncol. 2009; 92:23-31.

Sarkaria et al. Use of an orthotopic xenograft model for assessing the effect of epidermal growth factor receptor amplification on glioblastoma radiation response. Clin Cancer Res. 2006; 12: 2264-2271.

Sarkaria et al. Identification of molecular characteristics correlated with glioblastoma sensitivity to EGFR kinase inhibition through use of an intracranial xenograft test panel. Mal Cancer Ther. 2007; 6: 1167-1174.

Fournier AE, McKerracher L. Expression of specific tubulin isotypes increases during regeneration of injured CNS neurons, but not after the application of brain-derived neurotrophic factor (BDNF). J Neurosci. 1997;17(12): 4623-32.

Lockman et al. Synthesis of Substituted Quinazolines: Application to the Synthesis of Verubulin. Synthetic Communications, 2012, 42 (12), 1715-1723. Abstract.

Kumar et al. Radiosynthesis and In vivo evaluation of [IIC]MPC-6827, the first brain penetrant microtubule PET ligand, J. Med. Chem. 2018, 61(5): 2118-2123.

Solingapuram et al. Development of [11C]HD-800, a high affinity PET tracer for imaging microtubule, J Nucl Med. 2018, vol. 59, No. supplement 1, 6. Abstract.

Solingapuram et al., Radiosynthesis and evaluation of [11C]HD-800, a high affinity brain penetrant PET tracer for maging microtubules, ACS Medicinal Chemistry Letters, 2018, 9 (5), 452-456.

Banerjee et al. Heterocyclic-Fused Pyrimidines as Novel Tubulin Polymerization Inhibitors Targeting the Colchicine Binding Site: Structural Basis and Antitumor Efficacy. J Med Chem. 2018; 61(4): 1704-1718.

Cui et al. In Vivo and Mechanistic Studies on Antitumor Lead 7-Methoxy-4-(2-methylquinazolin-4-yl)-3,4-dihydroquinoxalin-2(1H)-one and Its Modification as a Novel Class of Tubulin-Binding Tumor-Vascular Disrupting Agents. J Med Chem. 2017; 60(13): 5586-5598.

Minegishi et al. Methyl 3-((6-Methoxy-1,4-dihydroindeno[I,2-c]pyrazol-3-yl)amino)benzoate (GN39482) as a Tubulin Polymerization Inhibitor Identified by MorphoBase and ChemProteoBase Profiling Methods. J. Med. Chem. 2015, 58, 4230-4241. Abstract.

\* cited by examiner

RADIOLABELED MICROTUBULE IMAGING COMPOUNDS AND USES THEREOF

CROSS-REFERENCE TO RELATED APPLICATION

The present application is a U.S. National Stage application of PCT/US2018/058187 filed on Oct. 30, 2018, which claims priority to U.S. Provisional Patent Application No. 62/578,903 filed on Oct. 30, 2017, which is incorporated herein by reference in its entirety.

FIELD OF THE INVENTION

The present disclosure relates to radiolabeled compounds and methods of use thereof, to diagnose, monitor, and treat neurological disorders, such as various degenerative neurological disorders, neuropsychiatric disorders, brain injuries, vascular diseases, and cancers in the brain and throughout the body. New drug treatment development can be accelerated by such radiolabeled compounds. Compositions comprising radiolabeled compounds are also disclosed.

BACKGROUND OF THE INVENTION

Imaging methods currently exist which enable monitoring of healthy and diseased tissues in vivo. In vivo monitoring allows one to assess how various treatments affect tissue chemistry and function in both a normal as well as a diseased state. Positron emission tomography (PET) is one such non-invasive imaging technique that is used in nuclear medicine to study in vivo biochemical and biological processes [1]. In PET, labeled compounds, such as radiotracers, may be administered in micromolar amounts to quantify tissue molecules in nanomolar or picomolar concentrations, allowing imaging studies to be performed without disturbing the biological systems being studied. PET radiotracers emit positrons, which then collide with electrons, generating gamma rays. The emitted gamma rays can be detected by scanners and then processed to obtain three dimensional images of tissues. PET has the ability to collect images repeatedly over time, thus providing information about the changes in distribution of the radiotracers. Other imaging techniques which detect radiotracers include nuclear scintigraphy and single photon emission computed tomography (SPECT). Magnetic resonance spectroscopy (MRS) can only measure down to microgram concentrations, much less sensitive than PET methods. Magnetic resonance imaging (MRI) and computer tomography (CT) measure general tissue structure or blood flow, but not individual molecule concentrations.

Using PET imaging techniques and radiotracers, a wide variety of different cellular processes can be studied, including, for example, the movement of microtubules, radiotracer uptake by cells, substrate metabolic rates, changes in receptor density/affinity, and regional blood flow [2].

Microtubules are an important part of healthy tissues. Abnormalities of microtubules are linked to the pathology of many diseases [3]. In addition, microtubules can be drug treatment targets [3]. There are only a few PET radiotracers available for imaging microtubules [4], but none of them can cross the blood brain barrier (BBB), preventing their use for imaging/diagnosing and for treating brain diseases [5].

Thus, there is a need for PET radiotracers that can cross the blood brain barrier. These radiotracers could be used in vivo: (a) as biomarkers for diseases involving microtubules outside and inside the brain, including malignancies, taupathies, traumatic brain injuries and other CNS disorders; nonbrain tissue disorders, and (b) for conducting target occupancy studies for small molecule therapeutic agent development.

SUMMARY

The present disclosure provides a compound of Formula (I) or (I'):

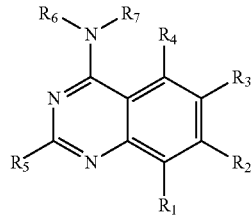

Formula (I)

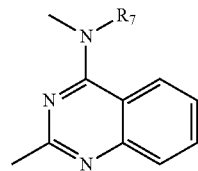

Formula (I')

or a pharmaceutically acceptable salt thereof, where, $R_1$-$R_7$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, $N(R'')_2$, CN, OR'', and SR'', where each occurrence of R'' is independently H, $C_1$-$C_6$ alkyl, $C_1$-$C_6$ fluoroalkyl, $C_2$-$C_6$ alkenyl, $C_2$-$C_6$ alkynyl, aryl, ($C_1$-$C_6$ alkylene)-aryl, $C_3$-$C_7$ cycloalkyl, $C_3$-$C_7$ cycloalkenyl or 3- to 7-membered heterocycle; each of which can be substituted or unsubstituted, and each of which and/or its substituents are optionally labeled with $^{11}C$, $^{18}F$, $^{75}Br$, $^{76}Br$, $^{120}I$, $^{123}I$, $^{124}I$, $^{125}I$, $^{131}I$, or $^{3}H$.

In a further embodiment, the present disclosure provides a compound selected from the group consisting of:

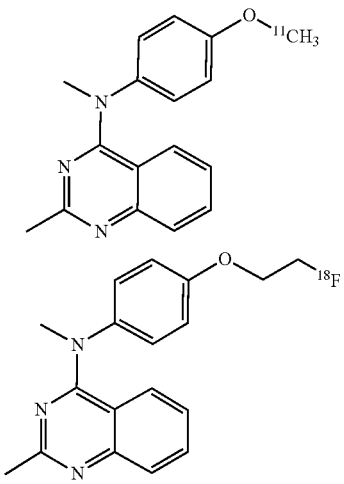

-continued

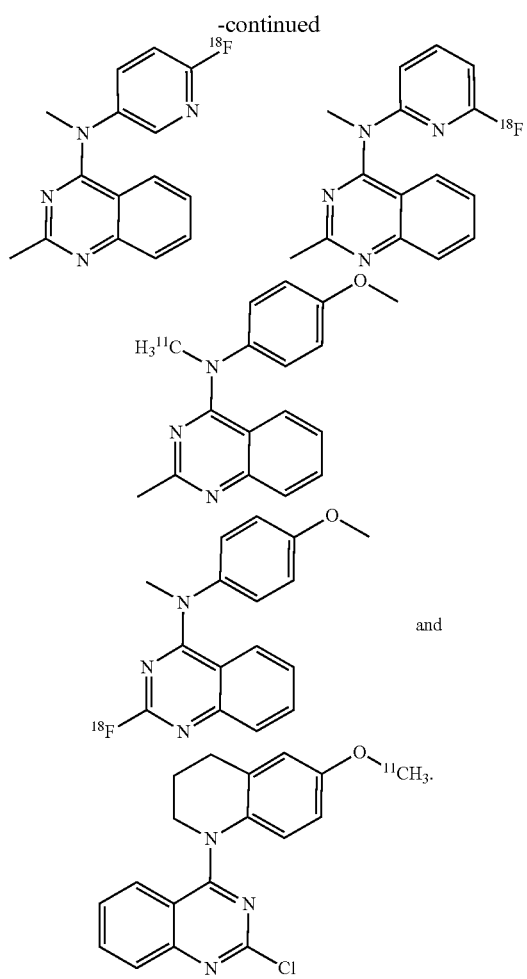

The present disclosure also provides a pharmaceutically acceptable salt thereof.

In another embodiment, the present disclosure provides a compound of Formula (II) or (II'):

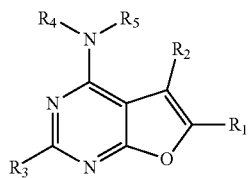

Formula (II)

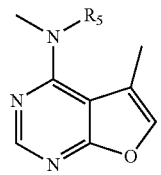

Formula (II')

or a pharmaceutically salt thereof, where, $R_1$-$R_5$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, N(R")$_2$, CN, OR", and SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, $C_3$-$C_7$ cycloalkenyl, or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

In another embodiment, the present disclosure provides a compound selected from the group consisting of:

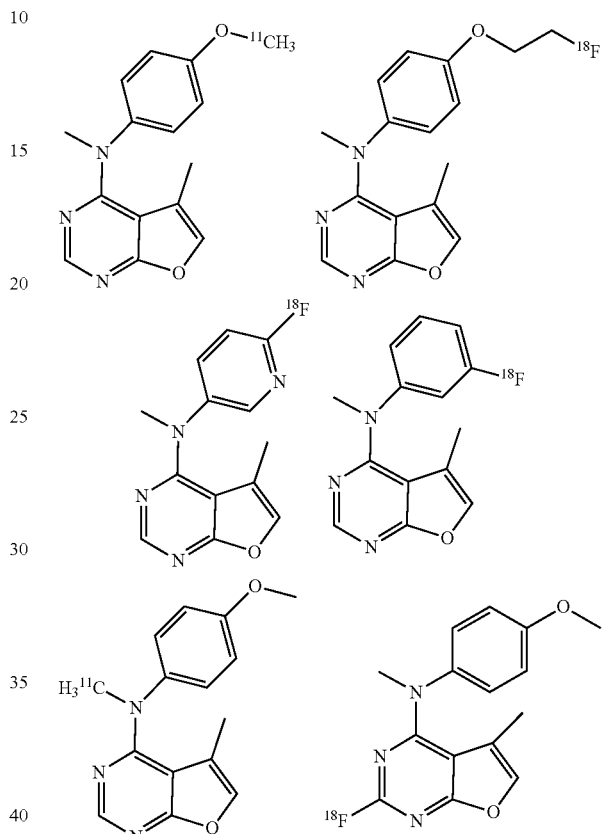

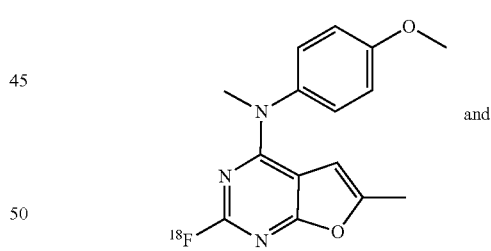

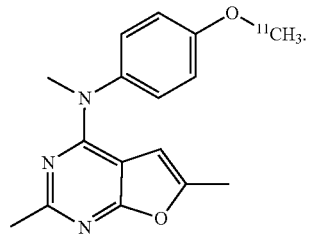

The present disclosure also provides a pharmaceutically acceptable salt thereof.

In a third embodiment, the present disclosure provides a compound of Formula (III):

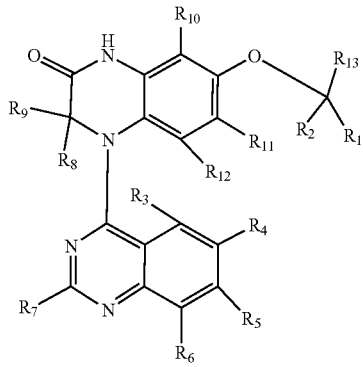

Fomula (III)

or a pharmaceutically acceptable salt thereof, where, $R_1$-$R_{12}$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, and 3- to 7-membered heterocycle; and $R_{13}$ is selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, N(R")$_2$, CN, OR", or SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

In one embodiment, the present disclosure provides a compound of Formula (III') or (III"):

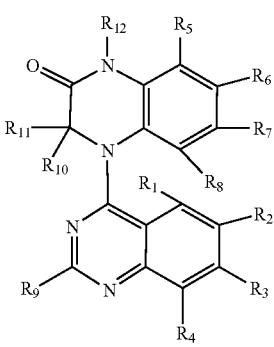

Formula (III')

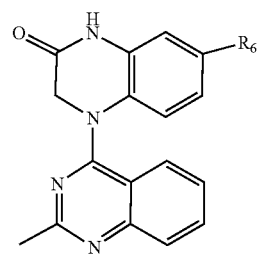

Formula (III")

or a pharmaceutically acceptable salt thereof, where, $R_1$-$R_{12}$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halo, $C_1$-$C_6$ haloalkyl, N(R")$_2$, CN, OR" or SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

In another aspect, the present disclosure provides a compound selected from the group consisting of:

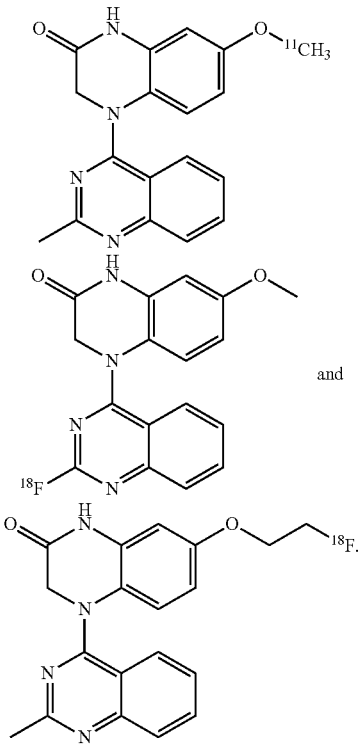

and

The present disclosure also provides a pharmaceutically acceptable salt thereof.

In another embodiment, the present disclosure provides a compound of Formula (IV) or (IV'):

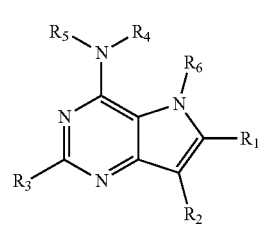

Formula (IV)

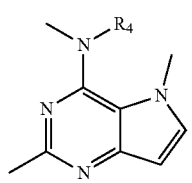

Formula (IV')

or a pharmaceutically acceptable salt thereof, where, $R_1$-$R_6$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, N(R")$_2$, CN, OR", and SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

In another embodiment, the present disclosure provides the following compounds:

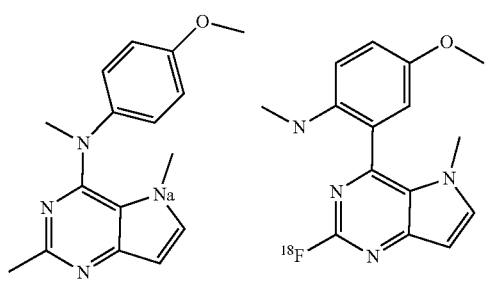

and

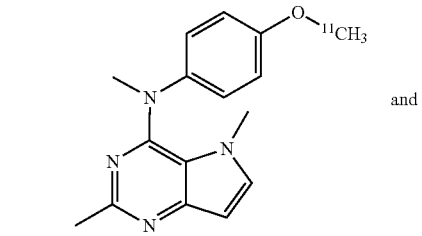

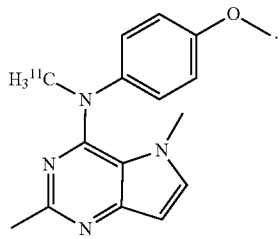

The present disclosure also provides a pharmaceutically acceptable salt thereof.

In another embodiment, the present disclosure provides a compound of Formula (V) or (V'):

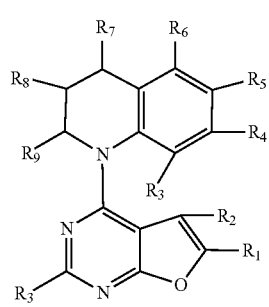

Formula (V)

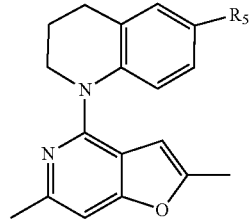

Formula (V')

or a pharmaceutically acceptable salt thereof, where, $R_1$-$R_9$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, N(R")$_2$, CN, OR", and SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

In another embodiment, the present disclosure provides the following compounds:

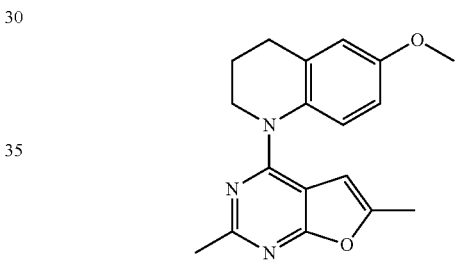

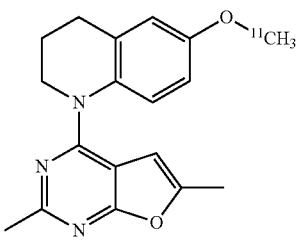

and

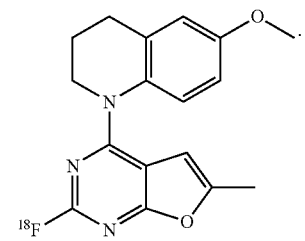

The present disclosure also provides a pharmaceutically acceptable salt thereof.

The present disclosure provides a compound of Formula (VI), (VI') or (VI"):

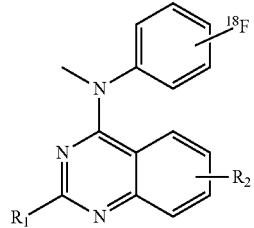
Formula (VI)

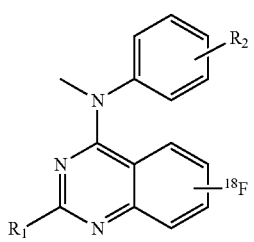
Formula (VI')

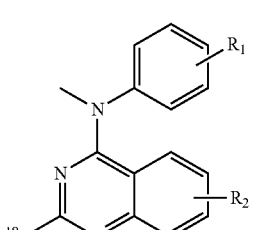
Formula (VI")

or a pharmaceutically acceptable salt thereof, where, $R_1$ and $R_2$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, $N(R")_2$, CN, OR", and SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^{3}$H.

The present disclosure provides a compound of Formula (VII), (VII') or (VII"):

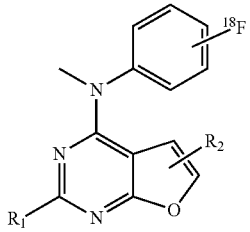
Formula (VII)

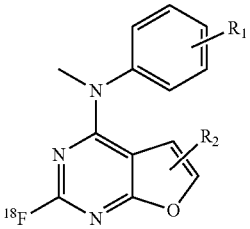
Formula (VII')

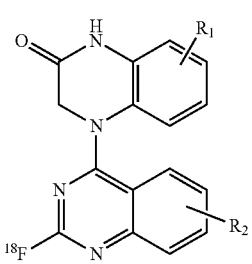
Formula (VII")

or a pharmaceutically acceptable salt thereof, where, $R_1$ and $R_2$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, $N(R")_2$, CN, OR", and SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^{3}$H.

The present disclosure provides a compound of Formula (VIII), (VIII') or (VIII"):

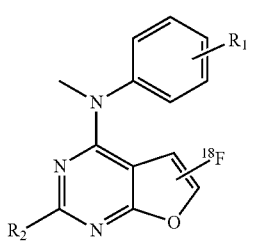
Formula (VIII)

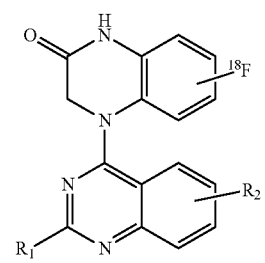
Formula (VIII')

Formula (VIII″)

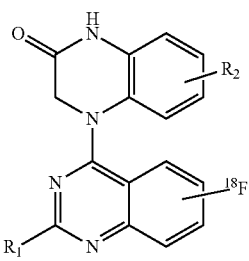

or a pharmaceutically acceptable salt thereof, where, $R_1$ and $R_2$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, $N(R'')_2$, CN, OR″ or SR″, where each occurrence of R″ is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

The present disclosure provides a compound of Formula (IX), (IX'), (IX″) or (IX‴):

Formula (IX)

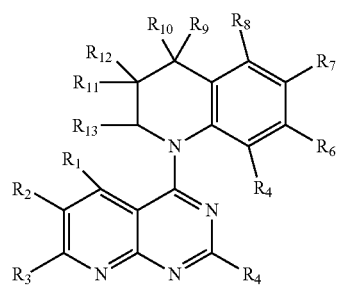

Formula (IX')

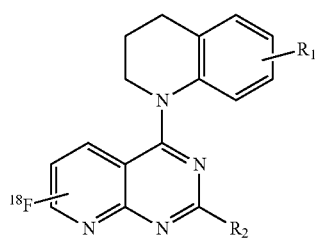

Formula (IX″)

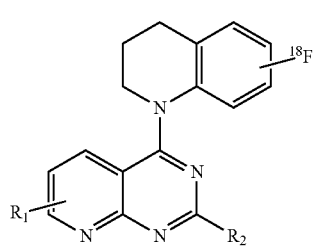

Formula (IX‴)

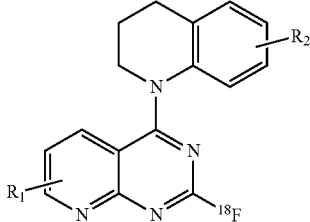

or a pharmaceutically acceptable salt thereof, where, $R_1$-$R_{13}$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, $N(R'')_2$, CN, OR″, and SR″, where each occurrence of R″ is independently H, $C_1$-$C_6$ alkyl, $C_1$-$C_6$ fluoroalkyl, $C_2$-$C_6$ alkenyl, $C_2$-$C_6$ alkynyl, aryl, ($C_1$-$C_6$ alkylene)-aryl, $C_3$-$C_7$ cycloalkyl, $C_3$-$C_7$ cycloalkenyl, or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

The present disclosure provides a compound selected from the group consisting of:

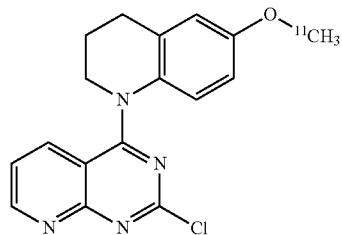

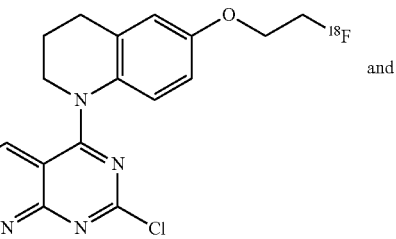

and

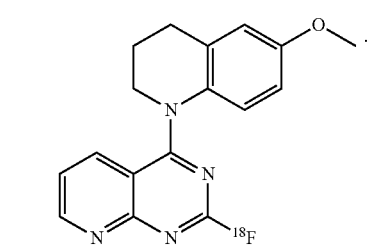

The present disclosure also provides a pharmaceutically acceptable salt thereof.

The present disclosure provides a compound of Formula (X):

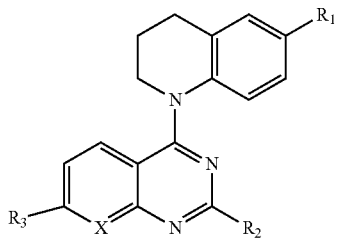

Formula (X)

X = C, N or a pharmaceutically acceptable salt thereof, where, X is C or N; $R_1$-$R_3$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, N(R")$_2$, CN, OR", and SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

The present disclosure provides a compound of Formula (XI):

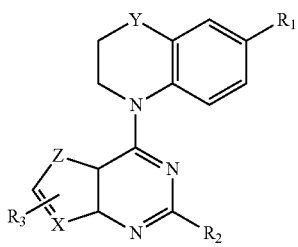

Formula (XI)

X = NH, O S; Z = O, NH or a pharmaceutically acceptable salt thereof, where, X is NH, O or S; Z is O or NH; $R_1$-$R_3$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$haloalkyl, N(R")$_2$, CN, OR", and SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

The present disclosure provides a compound of Formula (XII):

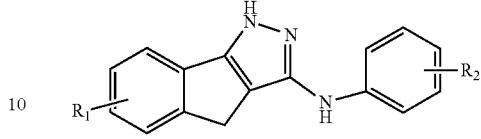

Formula (XII)

or a pharmaceutically acceptable salt thereof, where, $R_1$ and $R_2$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, N(R")$_2$, CN, OR", and SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

In one embodiment, the present disclosure provides the following compounds:

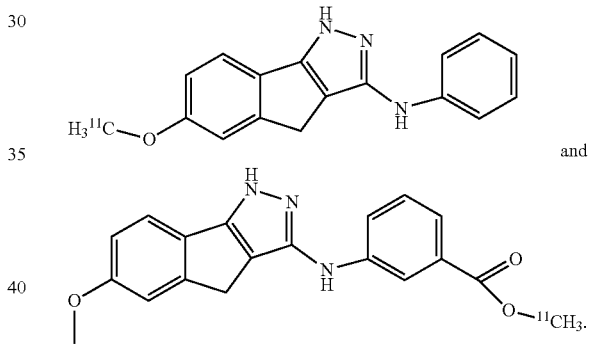

and

The present disclosure also provides a pharmaceutically acceptable salt thereof.

In one embodiment, the present disclosure provides the following compound:

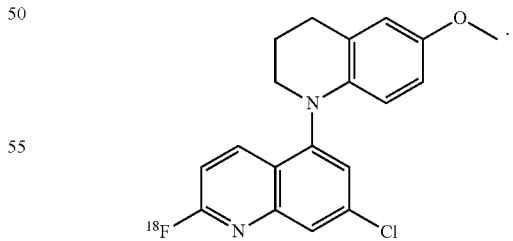

The present disclosure also provides a pharmaceutically acceptable salt thereof.

Also encompassed by the present disclosure is a composition comprising the present compound and a pharmaceutically acceptable carrier. The composition may be an imaging composition, e.g., for imaging or detecting microtubules and/or other targets (e.g., receptor tyrosine kinases). The composition may be for brain imaging, spinal cord imaging, or peripheral nervous system imaging.

The present disclosure also provides for a method of imaging or detecting microtubules and/or other targets (e.g., receptor tyrosine kinases) in a subject (in vivo), the method comprising, administering to the subject the present composition or compound (where the compound may be at an imaging-effective amount) or a pharmaceutically acceptable salt thereof. The method may further comprise detecting the radioactive emission of the present composition or compound.

The method may be for imaging microtubules in the nervous system of the subject, including the central nervous system (e.g., the brain and/or the spinal cord), or the peripheral nervous system of the subject.

The present disclosure also provides for a method of imaging or detecting microtubules and/or other targets (e.g., receptor tyrosine kinases) in a cell, a plurality of cells, a tissue, or an organ, the method comprising, administering to the cell, a plurality of cells, a tissue, or an organ, (or contacting the cell, a plurality of cells, a tissue, or an organ with) the present composition or compound (where the compound may be at an imaging-effective amount) or a pharmaceutically acceptable salt thereof. The method may further comprise detecting the radioactive emission of the present composition or compound.

The present disclosure provides for a pharmaceutical composition comprising a therapeutically effective amount of the present compound (and a pharmaceutically acceptable carrier).

The present disclosure provides for a composition (e.g., an imaging composition) comprising an effective amount (e.g., an imaging-effective amount) of the present compound (and a pharmaceutically acceptable carrier).

The present disclosure provides for a method of treating a neurological disorder in a subject in need thereof, the method comprising, administering to the subject the present composition or compound. The method may comprise administering the present composition or compound to the nervous system of the subject, including the central nervous system (e.g., the brain and the spinal cord), or peripheral nervous system of the subject.

The present disclosure provides for the following syntheses.

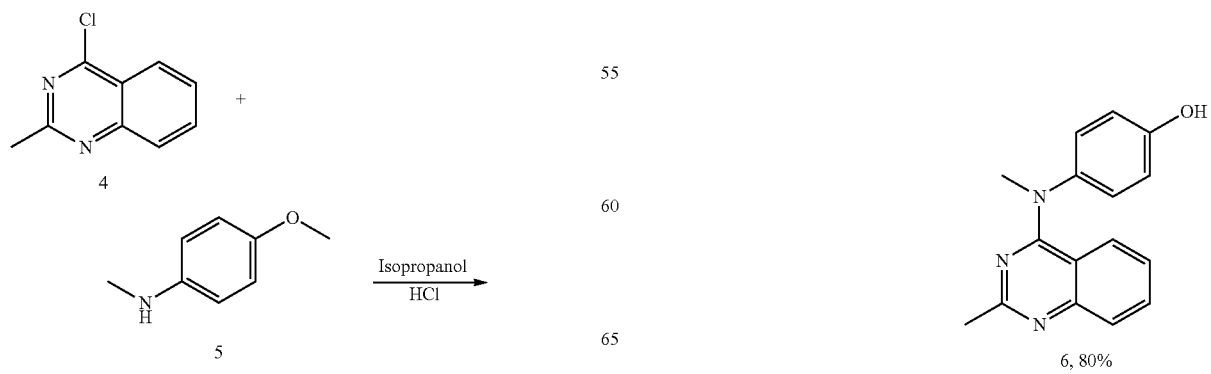

SCHEME 1

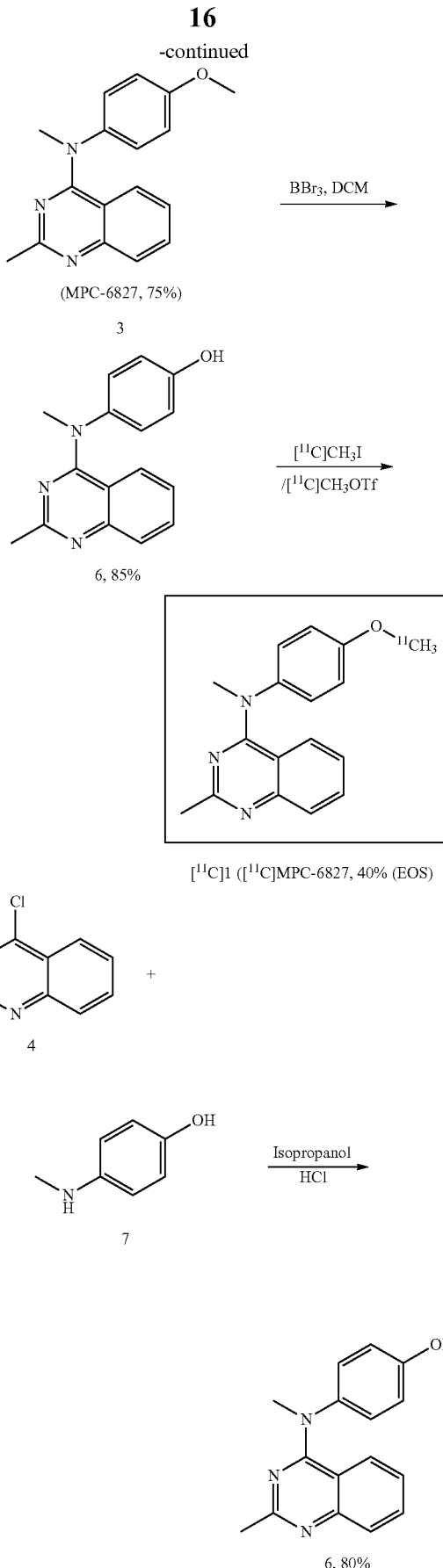

-continued
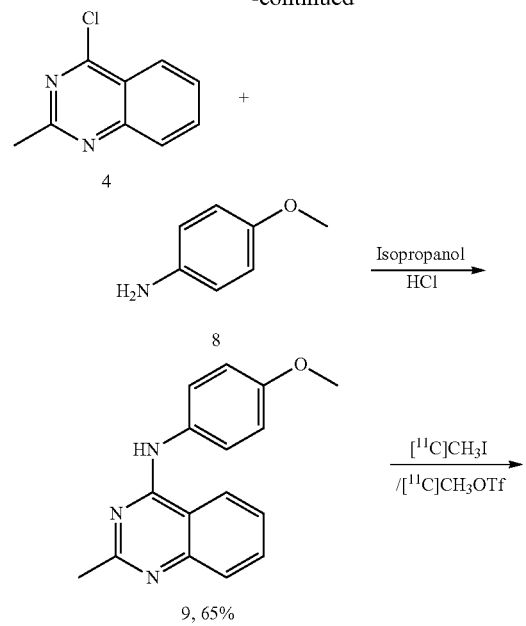
9, 65%
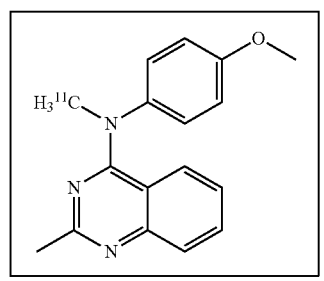
[11C]1 (N-[11C]N-MPC-6827), 8% (EOS)
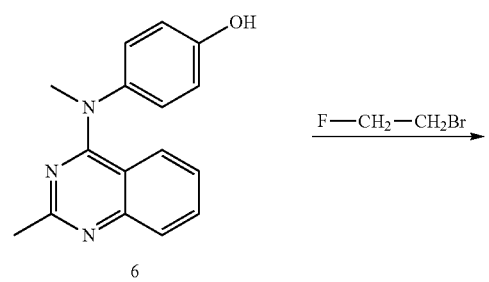
6
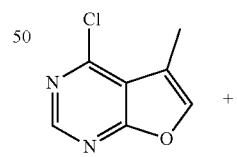
16 (Fluoroethyl-MPC-6827), 90%
SCHEME 2
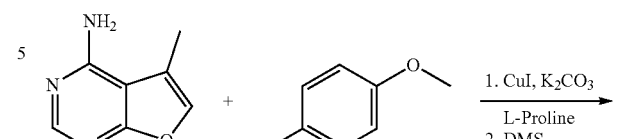
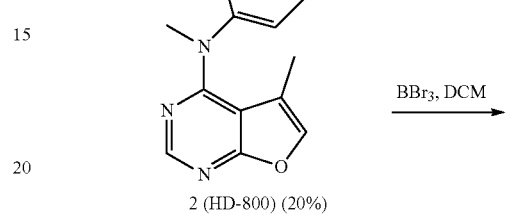
2 (HD-800) (20%)
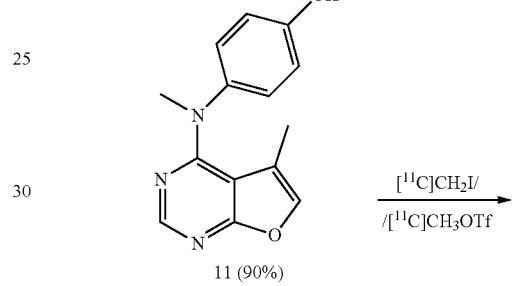
11 (90%)
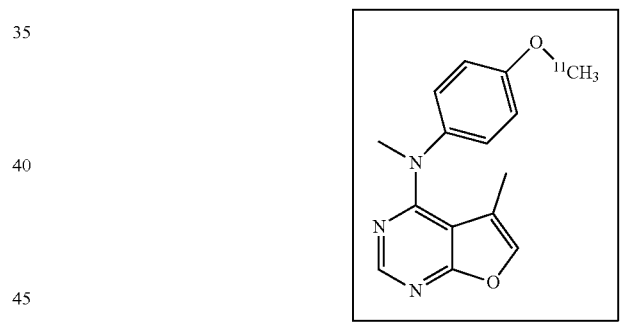
[11C]2([11C]HD-800) 60% (EOS)
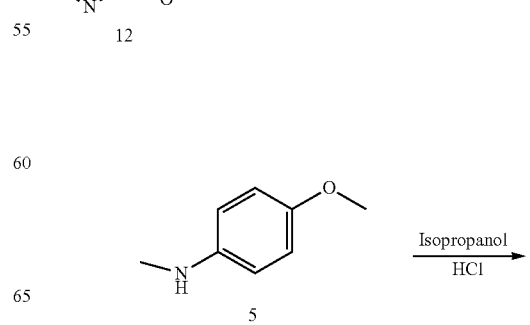
5

-continued
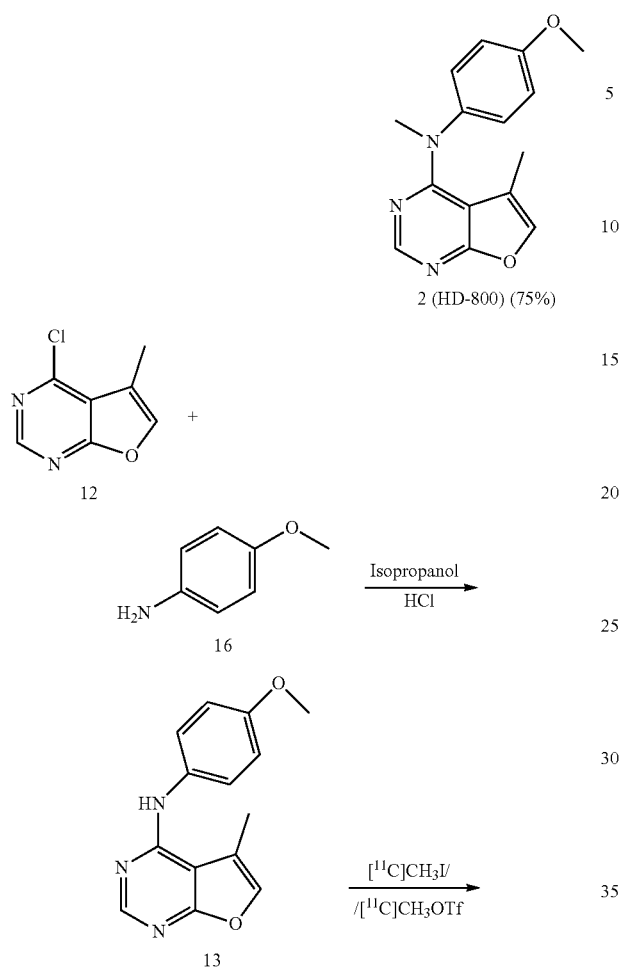
SCHEME 3
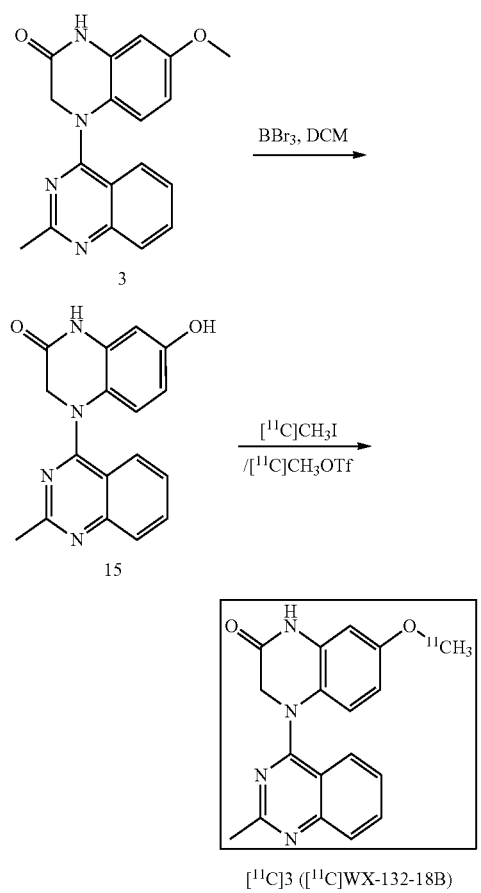
SCHEME 4
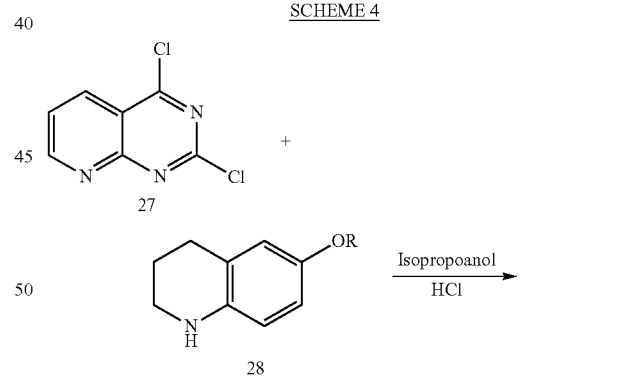
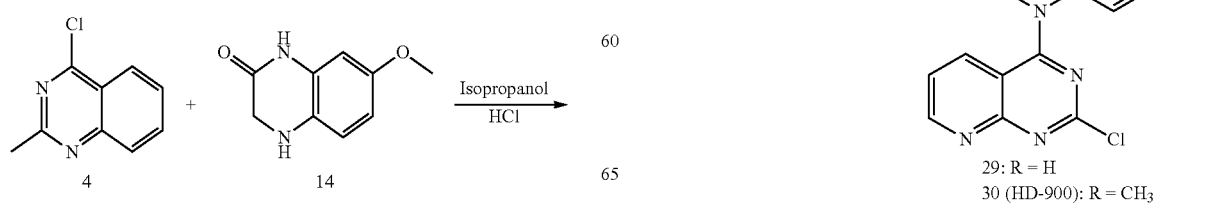

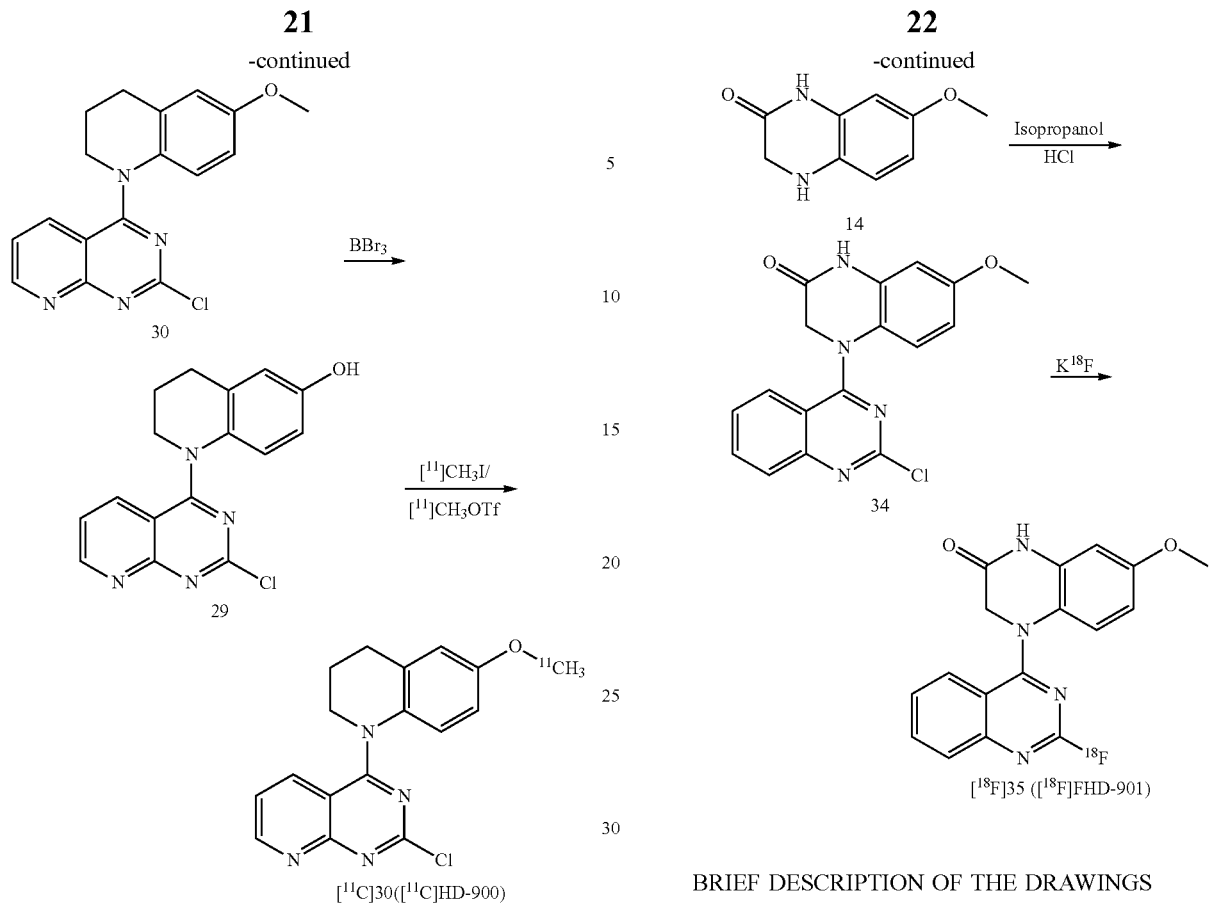

DETAILED DESCRIPTION OF THE INVENTION

Figure 1:
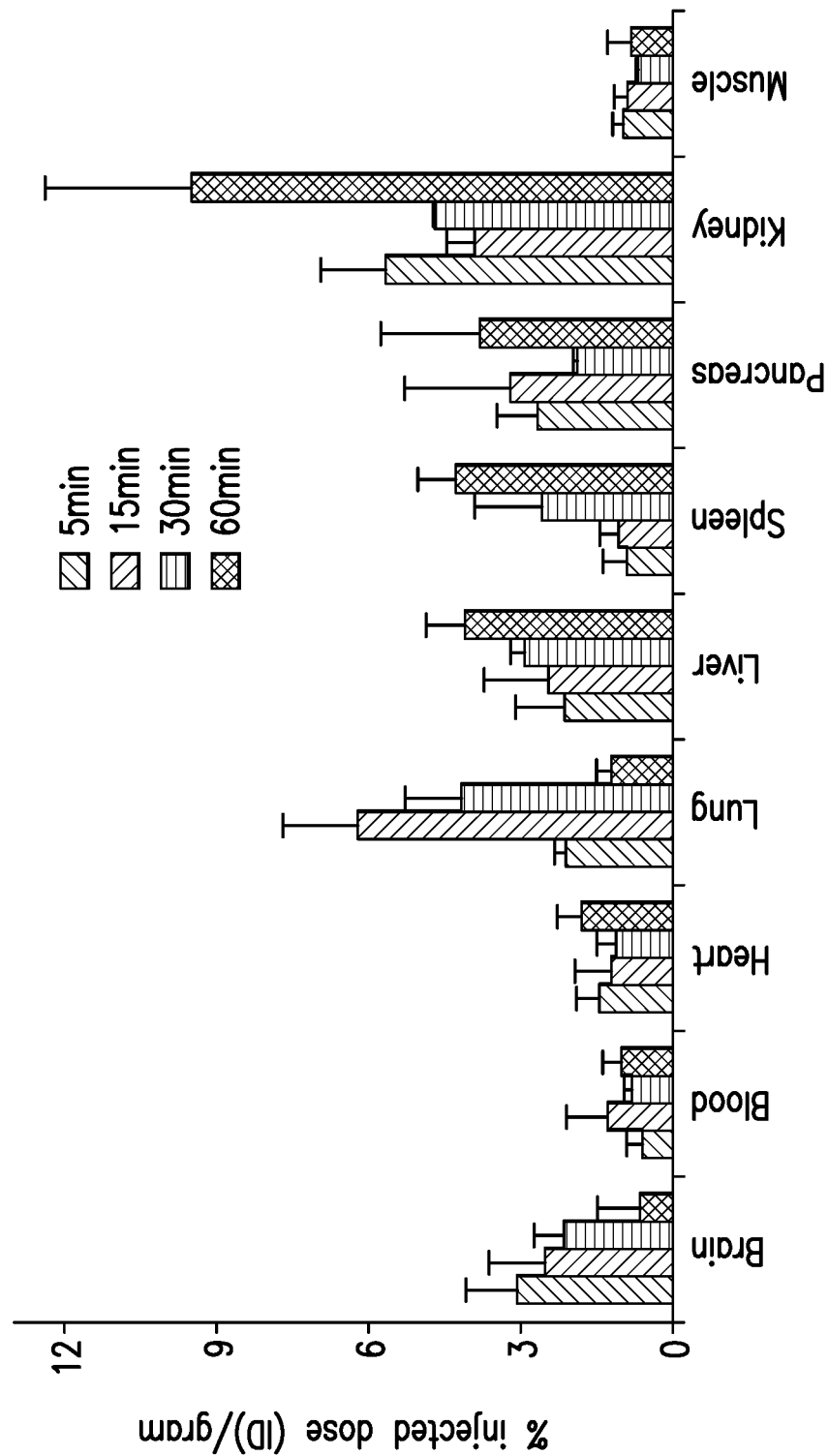
FIG. 1. Baseline biodistribition of [$^{11}$C]MPC-6827 in male white mice (n=3).

The present compounds (including radiolabeled compounds) can be used as imaging agents for microtubules and/or other targets (such as cell surface receptors including receptor tyrosine kinases). The present disclosure provides for a method of imaging or detecting microtubules and/or other targets in a subject, a cell, a plurality of cells, a tissue, or an organ, where the present composition or compound is administered to the subject, a cell, a plurality of cells, a tissue, or an organ. The present composition or compound may be used to treat a neurological disorder in a subject.

Using imaging techniques and radiotracers, a wide variety of different cellular processes can be studied, including, for example, the movement of microtubules, radiotracer uptake by cells, substrate metabolic rates, changes in receptor density/affinity, and regional blood flow [2]. Because abnormalities of microtubules are linked to the pathology of a large number of disorders, microtubules are both an important biomarker and drug target [3]. The compounds of the present disclosure may be used as PET imaging of radiotracers labeling microtubules inside and outside the brain. No radiotracer was previously shown to be able to do both.

Formula (I)

In one embodiment, the compound is represented by Formula (I) or (I') as shown below:

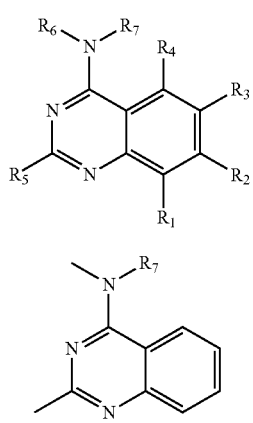

Formula (I)

Formula (I')

or a pharmaceutically acceptable salt thereof, where, $R_1$-$R_7$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, N(R")$_2$, CN, OR", and SR", where each occurrence of R" is independently H, C1-C6 alkyl, C1-C6 fluoroalkyl, C2-C6 alkenyl, C2-C6 alkynyl, aryl, (C1-C6alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^{3}$H.

Embodiments of the compounds (including radiolabeled compounds) of Formula (I) or (I') are shown below:

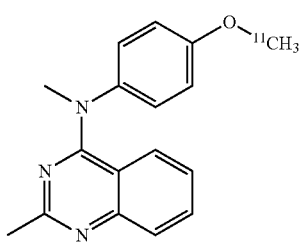

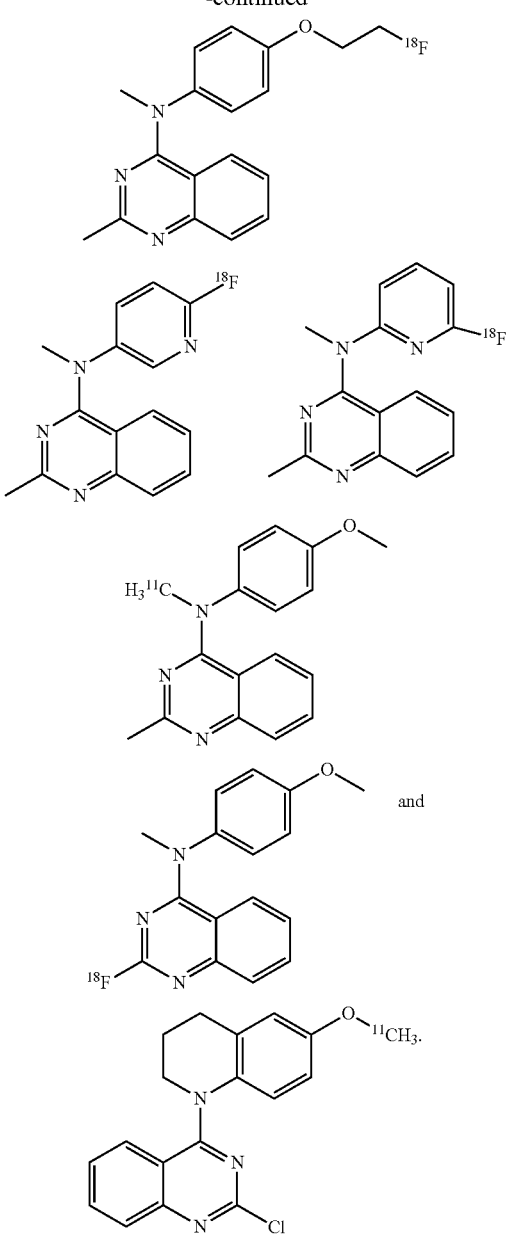

The present disclosure also provides a pharmaceutically acceptable salt thereof.

Formula (II)

In a second embodiment, the compound is represented by Formula (II) or Formula (II') showed below:

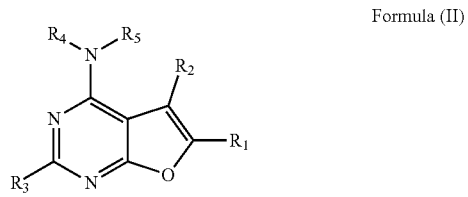

Formula (II)

-continued

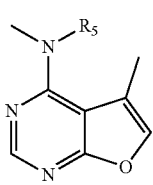

Formula (II')

or a pharmaceutically salt thereof, where, $R_1$-$R_5$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ by haloalkyl, $N(R")_2$, CN, OR", and SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}C$, $^{18}F$, $^{75}Br$, $^{76}Br$, $^{120}I$, $^{123}I$, $^{124}I$, $^{125}I$, $^{131}I$, or $^3H$.

Embodiments of the compounds of Formula (II) or (II') are shown below:

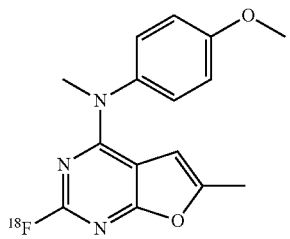

and

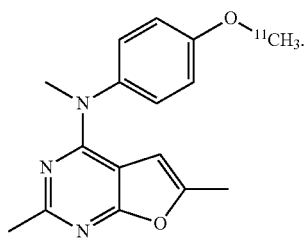

The present disclosure also provides a pharmaceutically acceptable salt thereof.

Formula (III)

In a third embodiment, the compound is represented by Formula (III) showed below:

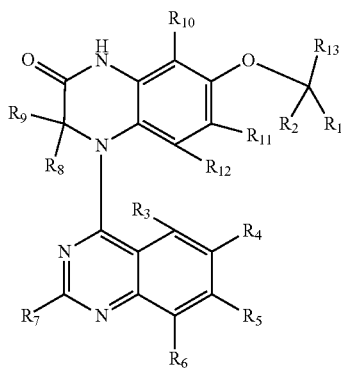

(III)

or a pharmaceutically salt, where, $R_1$-$R_{12}$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, and 3- to 7-membered heterocycle; and, $R_{13}$ is selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, $N(R")_2$, CN, OR" or SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}C$, $^{18}F$, $^{75}Br$, $^{76}Br$, $^{120}I$, $^{123}I$, $^{124}I$, $^{125}I$, $^{131}I$, or $^3H$.

In one embodiment, the present disclosure provides a compound of Formula (III') or (III"):

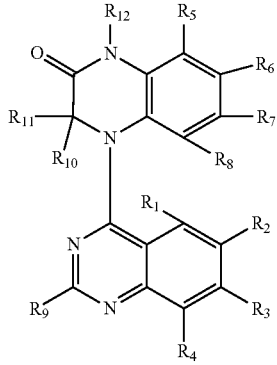
Formula (III')

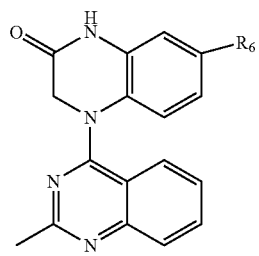
Formula (III")

or a pharmaceutically salt thereof, where, $R_1$-$R_{12}$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, N(R")$_2$, CN, OR", and SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

Embodiments of the compounds of Formula (III), (III') or (III") are shown below:

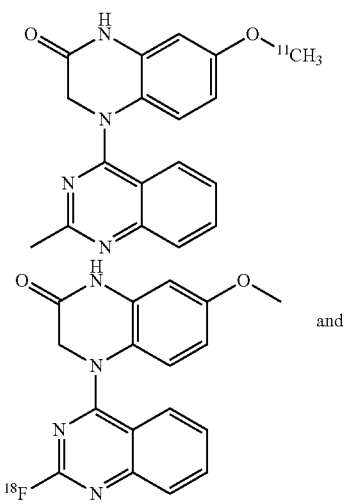

and

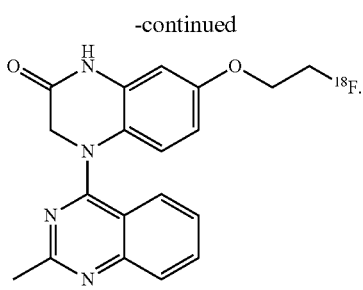

The present disclosure also provides a pharmaceutically acceptable salt thereof.

Formula (IV)

In another embodiment, the present disclosure provides a compound of Formula (IV) or (IV'):

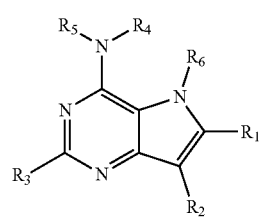
Formula (IV)

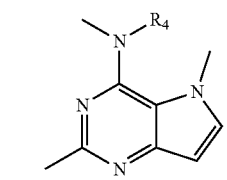
Formula (IV')

or a pharmaceutically salt thereof, where, $R_1$-$R_6$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, or 3- to 7-membered heterocycle, halogen, $C_1$-$C_6$ haloalkyl, N(R")$_2$, CN, OR" or SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

In another embodiment, the present disclosure provides the following compounds:

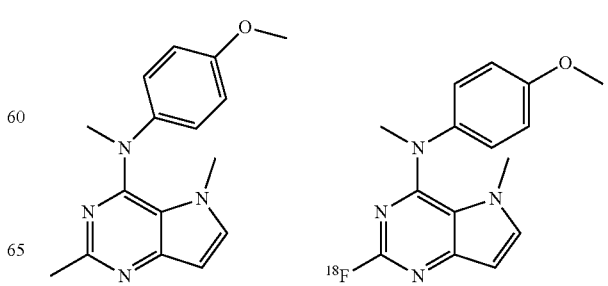

-continued

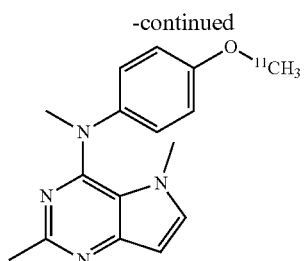

and

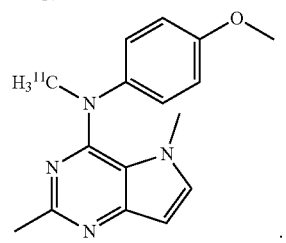

The present disclosure also provides a pharmaceutically acceptable salt thereof.

Formula (V)

In another embodiment, the present disclosure provides a compound of Formula (V) or (V'):

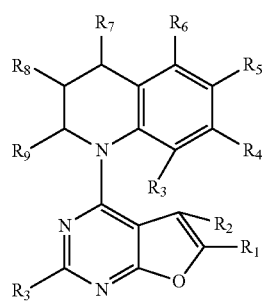

Formula (V)

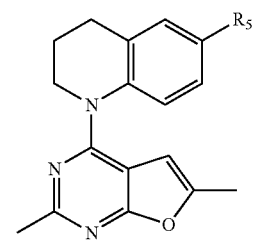

Formula (V')

or a pharmaceutically salt thereof, where, $R_1$-$R_9$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, or 3- to 7-membered heterocycle, halogen, $C_1$-$C_6$ haloalkyl, N(R")$_2$, CN, OR", and SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^{3}$H.

In another embodiment, the present disclosure provides the following compounds:

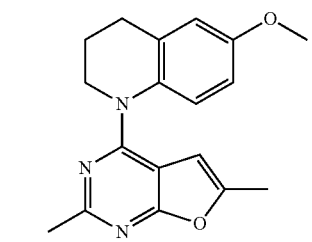

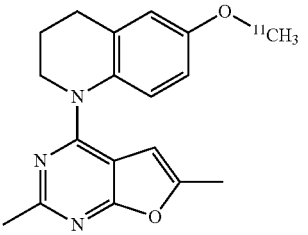

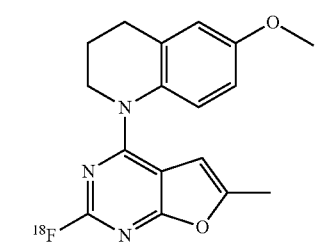

and

The present disclosure also provides a pharmaceutically acceptable salt thereof.

Formula (VI)

The present disclosure provides a compound of Formula (VI), (VI') or (VI"):

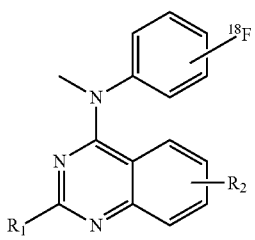

Formula (VI)

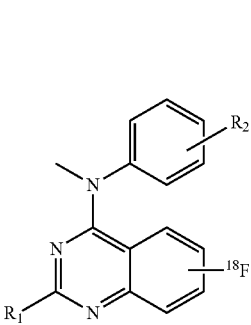

Formula (VI')

Formula (VI")

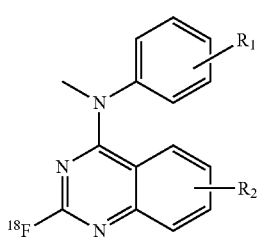

or a pharmaceutically acceptable salt thereof, where, $R_1$ and $R_2$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, N(R")$_2$, CN, OR", and SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

Formula (VII)

The present disclosure provides a compound of Formula (VII), (VII') or (VII"):

Formula (VII)

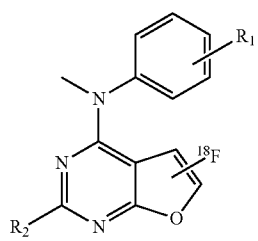

Formula (VII')

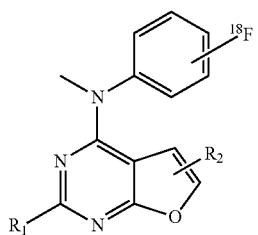

Formula (VII")

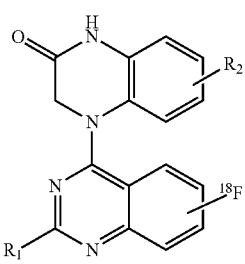

or a pharmaceutically acceptable salt thereof, where, $R_1$ and $R_2$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, N(R")$_2$, CN, OR", and SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

Formula (VIII)

The present disclosure provides a compound of Formula (VIII), (VIII') or (VIII"):

Formula (VIII)

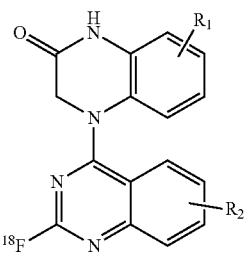

Formula (VIII')

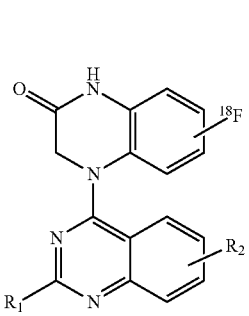

Formula (VIII")

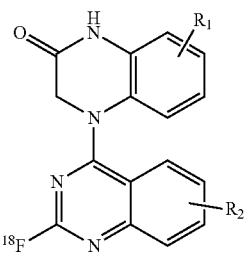

or a pharmaceutically acceptable salt thereof, where, $R_1$ and $R_2$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, N(R")$_2$, CN, OR" or SR", where each occurrence of R" is independently H, $C_1$-$C_6$ alkyl, $C_1$-$C_6$ fluoroalkyl, C2-C6 alkenyl, C2-C6 alkynyl, aryl, (C1-C6 alkylene)-aryl, C3-C7 cycloalkyl, C3-C7 cycloalkenyl or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

Formula (IX)

The present disclosure provides a compound of Formula (IX), (IX'), (IX") or (IX'''):

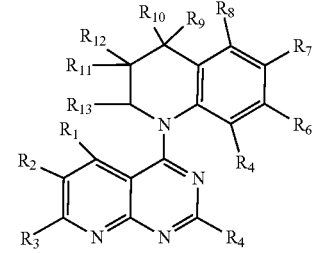

Formula (IX)

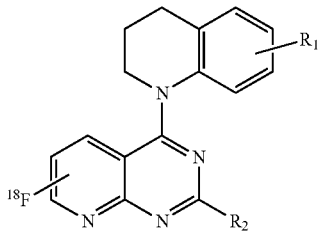

Formula (IX')

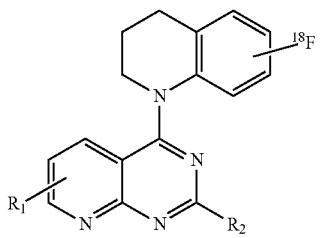

Formula (IX")

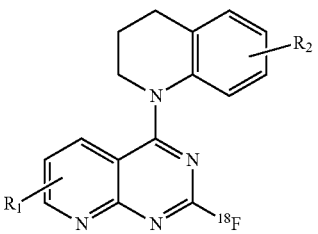

Formula (IX''')

or a pharmaceutically acceptable salt thereof, where, $R_1$-$R_3$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, N(R")$_2$, CN, OR", and SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}C$, $^{18}F$, $^{75}Br$, $^{76}Br$, $^{120}I$, $^{123}I$, $^{124}I$, $^{125}I$, $^{131}I$, or $^3H$.

The present disclosure provides a compound selected from the group consisting of:

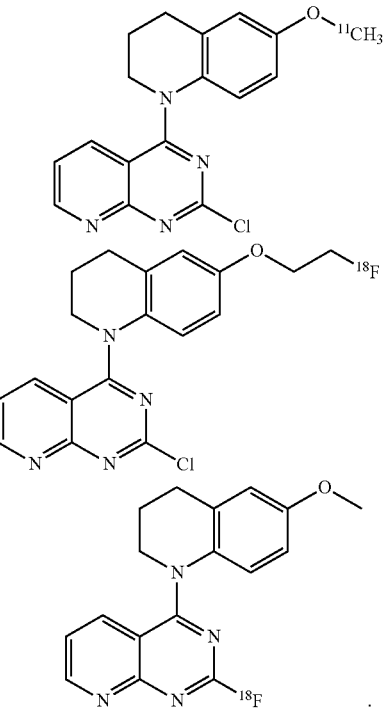

and

The present disclosure also provides a pharmaceutically acceptable salt thereof.

Formula (X)

The present disclosure provides a compound of Formula (X):

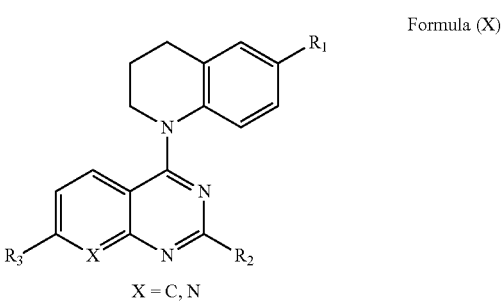

Formula (X)

X = C, N or a pharmaceutically acceptable salt thereof, where, X is C or N; $R_1$-$R_3$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, N(R")$_2$, CN, OR", and SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}C$, $^{18}F$, $^{75}Br$, $^{76}Br$, $^{120}I$, $^{123}I$, $^{124}I$, $^{125}I$, $^{131}I$, or $^3H$.

Formula (XI)

The present disclosure provides a compound of Formula (XI):

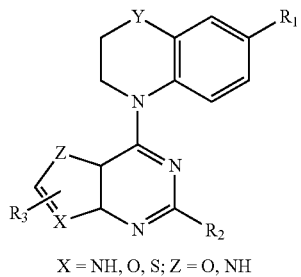

Formula (XI)

X = NH, O, S; Z = O, NH or a pharmaceutically acceptable salt thereof, where, X is NH, O or S; Z is O or NH; $R_1$-$R_3$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$haloalkyl, N(R")$_2$, CN, OR", and SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

Formula (XII)

The present disclosure provides a compound of Formula (XII):

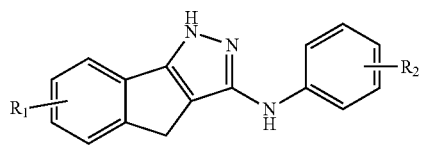

Formula (XII)

or a pharmaceutically acceptable salt thereof, where,
$R_1$ and $R_2$ are independently selected from the group consisting of H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halogen, $C_1$-$C_6$ haloalkyl, N(R")$_2$, CN, OR", and SR", where each occurrence of R" is independently H, C1-C6 alkyl, C1-C6 fluoroalkyl, C2-C6 alkenyl, C2-C6 alkynyl, aryl, (C1-C6 alkylene)-aryl, C3-C7 cycloalkyl, C3-C7 cycloalkenyl, or 3- to 7-membered heterocycle; each of which can be substituted or unsubstituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

In one embodiment, the present disclosure provides the following compounds:

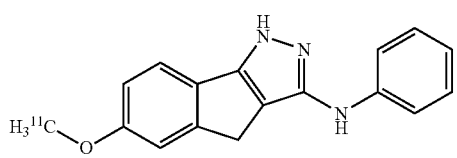

and

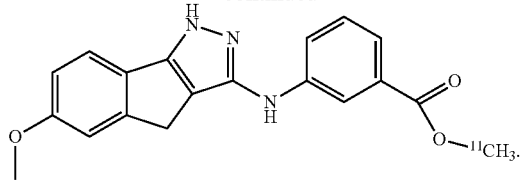

The present disclosure also provides a pharmaceutically acceptable salt thereof.

In one embodiment, the present disclosure provides the following compound:

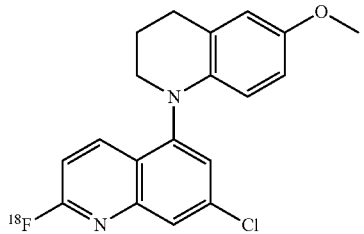

The present disclosure also provides a pharmaceutically acceptable salt thereof.

Also encompassed by the present disclosure is a composition comprising the present compound and a pharmaceutically acceptable carrier. The composition may be an imaging composition, e.g., for imaging or detecting microtubules. The composition may be for brain, spinal cord, or peripheral nervous system imaging.

The present disclosure also provides for a method of imaging or detecting microtubules in a subject (in vivo), the method comprising, administering to the subject the present composition or compound (where the compound may be at an imaging-effective amount) or a pharmaceutically acceptable salt thereof. The method may further comprise detecting the radioactive emission of the present composition or compound. The method may be for imaging microtubules in the nervous system of the subject, including the central nervous system (e.g., the brain and the spinal cord), or peripheral nervous system of the subject.

The present disclosure provides for a pharmaceutical composition comprising a therapeutically effective amount of the present compound (and a pharmaceutically acceptable carrier).

The present disclosure provides for a method of treating a neurological disorder in a subject, the method comprising, administering to the subject the present composition or compound. The method may comprise administering subject the present composition or compound to the nervous system of the subject, including the central nervous system (e.g., the brain and the spinal cord), or peripheral nervous system of the subject.

The present compounds may have one or more chiral centers, and, may exist in various stereoisomeric forms. Accordingly, the present compounds encompass all possible stereoisomers including, for example, tautomeric forms, diastereomers, enantiomers, and cis/trans-isomers. Also encompassed by the present disclosure are polymorphs, amorphous forms, solvates and hydrates of the present compounds.

The term "alkyl" as used herein, refers to a straight chain or branched non-cyclic hydrocarbon, wherein one of the hydrocarbon's hydrogen atoms has been replaced with a single bond. Hence, the term "$C_1$-$C_6$ alkyl" as used herein, refers to a straight chain or branched non-cyclic hydrocarbon having from 1 to 6 carbon atoms, wherein one of the hydrocarbon's hydrogen atoms has been replaced with a single bond. Representative straight chain $C_1$-$C_6$ alkyls include methyl, ethyl, n-propyl, n-butyl, n-pentyl, and n-hexyl. Representative branched $C_1$-$C_6$ alkyls include isopropyl, sec-butyl, isobutyl, tert-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, neohexyl, isohexyl, and the like. In certain embodiments, the $C_1$-$C_6$ alkyl may be substituted with one or more of the following groups: halo, O—($C_1$-$C_6$ alkyl), OH, CN, COOR', OC(O)R', N(R')$_2$, NHC(O)R' or C(O)NHR' groups wherein each R' is independently H or unsubstituted $C_1$-$C_6$ alkyl.

The term "haloalkyl" as used herein, refers to a $C_1$-$C_6$ alkyl group wherein one or more of the $C_1$-$C_6$ alkyl group's hydrogen atoms have been replaced with a halogen atom. Representative halogen atoms include fluorine, bromine and iodine. Representative fluoroalkyls include monofluoromethyl —CHF$_2$, —CH$_2$F, —CF$_3$, —CH(F)CH$_3$, or —CF$_2$CH$_3$. In certain embodiments, the haloalkyl may be substituted with one or more of the following groups: halo, O—($C_1$-$C_6$ alkyl), OH, CN, COOR', OC(O)R', N(R')$_2$, NHC(O)R' or C(O)NHR' groups wherein each R' is independently H or unsubstituted $C_1$-$C_6$ alkyl.

The term "alkenyl" as used herein, refers to a straight chain or branched non-cyclic hydrocarbon including at least one carbon-carbon double bond, wherein one of the hydrocarbon's hydrogen atoms has been replaced with a single bond. Hence, the term "$C_2$-$C_6$ alkenyl" as used herein, refers to a straight chain or branched non-cyclic hydrocarbon having from 2 to 6 carbon atoms and including at least one carbon-carbon double bond, wherein one of the hydrocarbon's hydrogen atoms has been replaced with a single bond. Representative straight chain and branched $C_2$-$C_6$ alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, and the like. In certain embodiments, the $C_2$-$C_6$ alkenyl may be substituted with one or more of the following groups: halo, O—($C_1$-$C_6$ alkyl), OH, CN, COOR', OC(O)R', N(R')$_2$, NHC(O)R' or C(O)NHR' groups wherein each R' is independently H or unsubstituted $C_1$-$C_6$ alkyl.

The term "alkynyl" as used herein, refers to a straight chain or branched non-cyclic hydrocarbon including at lease one carbon-carbon triple bond, wherein one of the hydrocarbon's hydrogen atoms has been replaced with a single bond. Hence, the term "$C_2$-$C_6$ alkynyl" as used herein, refers to a straight chain or branched non-cyclic hydrocarbon having from 2 to 6 carbon atoms and including at lease one carbon-carbon triple bond, wherein one of the hydrocarbon's hydrogen atoms has been replaced with a single bond. Representative straight chain and branched $C_2$-$C_6$ alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, and the like. In certain embodiments, the $C_2$-$C_6$ alkynyl may be substituted with one or more of the following groups: halo, O—($C_1$-$C_6$ alkyl), OH, CN, COOR', OC(O)R', N(R')$_2$, NHC(O)R' or C(O)NHR' groups wherein each R' is independently H or unsubstituted $C_1$-$C_6$ alkyl.

The term "alkylene" as used herein, refers to a straight chain or branched non-cyclic hydrocarbon, wherein two of the hydrocarbon's hydrogen atoms have been replaced with a single bond. Hence, the term "$C_1$-$C_6$ alkylene" as used herein, refers to a straight chain or branched non-cyclic hydrocarbon having from 1 to 6 carbon atoms, wherein two of the hydrocarbon's hydrogen atoms have been replaced with a single bond.

A "$^{11}$C-labeled $C_1$-$C_6$ alkylene group" is a $C_1$-$C_6$ alkylene group, as defined above, wherein one of the $C_1$-$C_6$ alkylene group's carbon atoms has been replaced with a $^{11}$C isotope.

A "$^{11}$C-labeled $C_1$-$C_6$ alkyl group" is a $C_1$-$C_6$ alkyl group, as defined above, wherein one of the $C_1$-$C_6$ alkyl group's carbon atoms has been replaced with a $^{11}$C isotope. Representative $^{11}$C-labeled $C_1$-$C_6$ alkylene groups include, but are not limited to, $^{11}$CH$_2$, CH$_2$$^{11}$CH$_2$, CH$_2$CH$_2$$^{11}$CH$_2$, CH$_2$CH$_2$CH$_2$$^{11}$CH$_2$, CH$_2$CH$_2$CH$_2$CH$_2$$^{11}$CH$_2$, and CH$_2$CH$_2$CH$_2$CH$_2$CH$_2$$^{11}$CH$_2$.

A "$^{18}$F-labeled $C_1$-$C_6$ alkylene group" is a $C_1$-$C_6$ alkyl group, as defined above, wherein one of the $C_1$-$C_6$ alkyl group's hydrogen atoms has been replaced with a $^{18}$F isotope.

The term "alkenylene" as used herein, refers to a straight chain or branched non-cyclic hydrocarbon including at least one carbon-carbon double bond, wherein two of the hydrocarbon's hydrogen atoms have been replaced with a single bond. Hence, the term "$C_2$-$C_6$ alkenylene" as used herein, refers to a straight chain or branched non-cyclic hydrocarbon having from 2 to 6 carbon atoms and including at least one carbon-carbon double bond, wherein two of the hydrocarbon's hydrogen atoms have been replaced with a single bond.

A "$^{11}$C-labeled $C_2$-$C_6$ alkenylene group" is a $C_2$-$C_6$ alkenylene group, as defined above, wherein one of the $C_2$-$C_6$ alkenylene group's carbon atoms has been replaced with a $^{11}$C isotope.

A "$^{18}$F-labeled $C_2$-$C_6$ alkenylene group" is a $C_2$-$C_6$ alkenylene group, as defined above, wherein one of the $C_2$-$C_6$ alkenylene group's hydrogen atoms has been replaced with a $^{18}$F isotope.

The term "alkynylene" as used herein, refers to a straight chain or branched non-cyclic hydrocarbon including at lease one carbon-carbon triple bond, wherein two of the hydrocarbon's hydrogen atoms have been replaced with a single bond. Hence, the term "$C_2$-$C_6$ alkynylene" as used herein, refers to a straight chain or branched non-cyclic hydrocarbon having from 2 to 6 carbon atoms and including at lease one carbon-carbon triple bond, wherein two of the hydrocarbon's hydrogen atoms have been replaced with a single bond.

A "$^{11}$C-labeled $C_2$-$C_6$ alkynylene group" is a $C_2$-$C_6$ alkynylene group, as defined above, wherein one of the $C_2$-$C_6$ alkynylene group's carbon atoms has been replaced with a $^{11}$C isotope.

A "$^{18}$F-labeled $C_2$-$C_6$ alkynylene group" is a $C_2$-$C_6$ alkynylene group, as defined above, wherein one of the $C_2$-$C_6$ alkynylene group's hydrogen atoms has been replaced with a $^{18}$F isotope.

The term "alkoxycarbonyl" means a moiety of the formula —COOR', where R' is unsubstituted $C_1$-$C_6$ alkyl. Examples of such alkoxycarbonyl include methoxycarbonyl, ethoxycarbonyl, and the like.

The term "aryl" as used herein refers to a $C_6$-$C_{14}$ aromatic group. Exemplary aryl groups include a phenyl group, a biphenyl group, biphenylene group, anthracene group, fulvene group, phenanthrene group, or a naphthyl group. In certain embodiments, the aryl group may be substituted with one or more of the following groups: halo, O—$C_1$-$C_6$ alkyl, O—$C_2$-$C_6$ alkenyl, O—$C_2$-$C_6$ alkynyl, OH, CN, COOR', OC(O)R', N(R')$_2$, NHC(O)R', S—($C_1$-$C_6$ alkyl or alkenyl or alkynyl), S—(O)—$C_1$-$C_6$ alkyl, S(O)—$C_2$-$C_6$ alkenyl, S(O)—$C_2$-$C_6$ alkynyl, S—(O$_2$)—$C_1$-$C_6$ alkyl, S(O$_2$)—$C_2$-$C_6$ alkenyl, S(O$_2$)—$C_2$-$C_6$ alkynyl, or C(O)NHR' groups wherein each R' is independently —H or unsubstituted —$C_1$-$C_6$ alkyl.

The term "cycloalkyl" as used herein refers to a saturated non-aromatic monocyclic cycloalkyl ring. Hence, the term "$C_3$-$C_7$ cycloalkyl" as used herein refers to a 3-, 4-, 5-, 6- or 7-membered saturated non-aromatic monocyclic cycloalkyl ring. Representative $C_3$-$C_7$ monocyclic cycloalkyl groups include, but are not limited to, cyclopropyl, cyclobutyl, cyclopentyl, cyclohexyl and cycloheptyl. In certain embodiments, the cycloalkyl group may be substituted with one or more of the following groups: halo, O—$C_1$-$C_6$ alkyl, O—$C_2$-$C_6$ alkenyl, O—$C_2$-$C_6$ alkynyl, OH, CN, COOR', OC(O)R', N(R')$_2$, NHC(O)R', S—($C_1$-$C_6$ alkyl or alkenyl or alkynyl), S—(O)—$C_6$ alkyl, S(O)—$C_2$-$C_6$ alkenyl, S(O)—$C_2$-$C_6$ alkynyl, S—(O$_2$)—$C_1$-$C_6$ alkyl, S(O$_2$)—$C_2$-$C_6$ alkenyl, S(O$_2$)—$C_2$-$C_6$ alkynyl, or C(O)NHR' groups wherein each R' is independently H or unsubstituted $C_1$-$C_6$ alkyl.

The term "cycloalkenyl" as used herein refers to non-aromatic monocyclic carbocyclic ring having at least one endocyclic double bond. Hence, the term "$C_3$-$C_7$ cycloalkenyl" as used herein refers to a 3-, 4-, 5-, 6- or 7-membered non-aromatic monocyclic carbocyclic ring having at least one endocyclic double bond, but which is not aromatic. It is to be understood that when any two groups, together with the carbon atom to which they are attached form a $C_3$-$C_7$ monocyclic cycloalkenyl group, the carbon atom to which the two groups are attached remain tetravalent. Representative $C_3$-$C_7$ monocyclic cycloalkenyl groups include, but are not limited to, cyclopropenyl, cyclobutenyl, 1,3-cyclobutadienyl, cyclopentenyl, 1,3-cyclopentadienyl, cyclohexenyl, 1,3-cyclohexadienyl, cycloheptenyl, 1,3-cycloheptadienyl, 1,4-cycloheptadienyl and -1,3,5-cycloheptatrienyl. In one embodiment, the cycloalkenyl group is substituted with one or more of the following groups: halo, O—$C_1$-$C_6$ alkyl, O—$C_2$-$C_6$ alkenyl, O—$C_2$-$C_6$ alkynyl, OH, CN, COOR', OC(O)R', N(R')$_2$, NHC(O)R', S—($C_1$-$C_6$ alkyl or alkenyl or alkynyl), S—(O)—$C_1$-$C_6$ alkyl, S(O)—$C_2$-$C_6$ alkenyl, S(O)—$C_2$-$C_6$ alkynyl, S—(O$_2$)—$C_1$-$C_6$ alkyl, S(O$_2$)—$C_2$-$C_6$ alkenyl, S(O$_2$)—$C_2$-$C_6$ alkynyl, or C(O)NHR' groups wherein each R' is independently H or unsubstituted $C_1$-$C_6$ alkyl.

The terms "halo" or "halogen" as used herein, refer to F, Cl, Br, or I, or their radioactive isotopes. Exemplary radioactive isotopes include $^{18}F$, $^{75}Br$, $^{76}Br$, $^{120}I$, $^{123}I$, $^{124}I$, $^{125}I$, and $^{131}I$.

The term "3- to 7-membered heterocycle" refers to: (i) a 3- or 4-membered non-aromatic monocyclic cycloalkyl in which one of the ring carbon atoms has been replaced with a N, O or S atom; (ii) a 5-, 6-, or 7-membered aromatic or non-aromatic monocyclic cycloalkyl in which 1-4 of the ring carbon atoms have been independently replaced with a N, O or S atom. The term 3- to 7-membered heterocycle also encompasses any heterocycles described by (i) or (ii) which are fused to a benzene ring, or in which any one of the ring carbon atoms comprises a carbonyl group, such as in lactam and lactone ring systems. The non-aromatic 3- to 7-membered heterocycles can be attached via a ring nitrogen, sulfur, or carbon atom. The aromatic 3- to 7-membered heterocycles are attached via a ring carbon atom. Representative examples of a 3- to 7-membered heterocycle group include, but are not limited to, dihydrofuran-2-one, dihydrofuranyl, furanyl, benzofuranyl, furazanyl, imidazolidinyl, imidazolinyl, imidazolyl, benzimidazolyl, indazolyl, indolinyl, indolyl, indolizinyl, isoindolinyl, isothiazolyl, isoxazolyl, benzisoxazolyl, morpholinyl, oxadiazolyl, oxazolidinyl, oxazolyl, benzoxazolyl, oxazolidinyl, pyrimidinyl, phenanthridinyl, phenanthrolinyl, piperazinyl, piperidinyl, pyranyl, benzopyranyl, pyrazinyl, pyrazolidinyl, pyrazolinyl, pyrazolyl, pyridazinyl, pyridooxazole, pyridoimidazole, pyridothiazole, pyridyl, pyrimidinyl, pyrrolidinyl, pyrrolinyl, quinolinyl, isoquinolinyl, quinoxalinyl, phthalazinyl, cinnolinyl, quinolizinyl, quinazolinyl, quinuclidinyl, tetrahydrofuranyl, thiadiazinyl, thiadiazolyl, thiazolyl, benzthiazolyl, thienyl, thienothiazolyl, thienooxazolyl, thienoimidazolyl, thiomorpholinyl, thiophenyl, benzothiphenyl, triazinyl, and triazolyl. In one embodiment, the 3- to 7-membered heterocycle group is substituted with one or more of the following groups: halo, O—($C_1$-$C_6$ alkyl), OH, CN, COOR', OC(O)R', N(R')$_2$, NHC(O)R' or C(O)NHR' groups wherein each R' is independently H or unsubstituted $C_1$-$C_6$ alkyl.

The term "5- to 7-membered aromatic heterocycle" refers to a 5-, 6-, or 7-membered aromatic monocyclic cycloalkyl in which 1-4 of the ring carbon atoms have been independently replaced with a N, O or S atom. The term 5- to 7-membered aromatic heterocycle also encompasses any heterocycles described which are fused to a benzene ring, or in which any one of the ring carbon atoms comprises a carbonyl group, such as in lactam and lactone ring systems. The 5- to 7-membered aromatic heterocycles are attached via a ring carbon atom. Representative examples of a 5- to 7-membered aromatic heterocycle group include, but are not limited to, furanyl, benzofuranyl, furazanyl, imidazolyl, benzimidazolyl, indazolyl, indolyl, indolizinyl, isoindolinyl, isothiazolyl, isoxazolyl, benzisoxazolyl, oxadiazolyl, oxazolidinyl, oxazolyl, benzoxazolyl, oxazolidinyl, pyrimidinyl, phenanthridinyl, phenanthrolinyl, pyranyl, benzopyranyl, pyrazinyl, pyrazolyl, pyridazinyl, pyridooxazole, pyridoimidazole, pyridothiazole, pyridyl, pyrimidinyl, quinolinyl, isoquinolinyl, quinoxalinyl, phthalazinyl, cinnolinyl, quinolizinyl, quinazolinyl, thiadiazinyl, thiadiazolyl, thiazolyl, benzthiazolyl, thienyl, thienothiazolyl, thienooxazolyl, thienoimidazolyl, thiophenyl, and benzothiphenyl. In certain embodiments, the 5- to 7-membered aromatic heterocycle group may be substituted with one or more of the following groups: halo, O—($C_1$-$C_6$ alkyl), OH, CN, COOR', OC(O)R', N(R')$_2$, NHC(O)R' or C(O)NHR' groups wherein each R' is independently H or unsubstituted $C_1$-$C_6$ alkyl.

The term "imaging-effective amount" when used in connection with a radiolabeled compound is an amount of the radiolabeled compound that is sufficient to produce a visible image, e.g., of microtubules in a tissue or organ of interest, when the radiolabeled compound is administered to a person. The method of detection of the compounds may include, nuclear scintigraphy, positron emission tomography (PET), single photon emission computed tomography (SPECT), magnetic resonance imaging (MRI), magnetic resonance spectroscopy (MRS), computed tomography (CT), or a combination thereof depending on the intended use and the imaging methodology available to the medical or research personnel.

Formulations

The radiolabeled compounds may be formulated using a variety of different excipients. Such physiologically acceptable excipients can be liquids, such as water for injection, bacteriostatic water for injection, sterile water for injection, and oils, including those of petroleum, subject, vegetable, or synthetic origin, such as peanut oil, soybean oil, mineral oil, sesame oil and the like. The pharmaceutical excipients can be saline, gum acacia; gelatin, starch paste, talc, keratin, colloidal silica, urea and the like. In addition, auxiliary, stabilizing, thickening, lubricating, and coloring agents can be used. In one embodiment, the physiologically acceptable excipients are sterile when administered to a subject. Water is a particularly useful excipient when the radiolabeled compounds of the present disclosure are administered intravenously. Saline solutions and aqueous dextrose and glycerol solutions can be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. The radiolabeled compounds can also contain minor amounts of wetting or emulsifying agents, or pH buffering agents.

The present compounds can exist as pharmaceutically acceptable salts. The term "pharmaceutically acceptable salt" represents salts or zwitterionic forms of the compounds. The salts can be prepared during the final isolation and purification of the compounds or separately by reacting the appropriate compound with a suitable acid or base. Pharmaceutically acceptable salts include acid and basic addition salts [7].

Suitable acids for use in the preparation of pharmaceutically acceptable salts are acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid, undecylenic acid, valeric acid and ascorbic acid.

Suitable bases for use in the preparation of pharmaceutically acceptable salts are inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

In another embodiment, the radiolabeled compounds can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized-powder or water free concentrate in a hermetically sealed container such as an ampule or sachette indicating the quantity of active agent. Where the radiolabeled compounds are to be administered by infusion, they can be dispensed, for example, with an infusion bottle containing sterile pharmaceutical grade water or saline. Where the radiolabeled compounds are administered by injection, an ampule of sterile water for injection or saline is often used so that the ingredients can be mixed prior to administration.

Consistent with the pharmaceutical compositions, kits and/or formulations described herein, other additives may be added to reduce radiolysis such as, for example, ascorbic acid. The formulations, kits and/or compositions may further comprise a suitable organic solvent, such as an alcohol, which may be present in amounts up to about 20%. In some embodiments, the alcohol is present from about 1% to about 5%; from about 5% to about 10%; from about 10% to about 15%; or from about 15% to about 20%. In some embodiments, the alcohol is present in about 10%. In some embodiments, the organic solvent is ethanol.

Imaging

The present compound can be used as an imaging agent (in an imaging composition) to image microtubules in a subject (in vivo).

The present method may use the present compound as an imaging agent (in an imaging composition) and employ a nuclear imaging technique such as positron emission tomography (PET) and single photon emission computed tomography (SPECT). The method may detect/monitor a distribution of the imaging agent within the subject or a portion thereof.

The method for imaging/detecting microtubules in a subject may comprise the step of administering to the subject an imaging composition comprising the present compound. The method may further comprise the step of detecting the radioactive emission of the present compound after administration. In one embodiment, the detecting step is carried out using PET. In another embodiment, the detecting step is carried out using SPECT.

In one embodiment, the microtubules being imaged/detected are in the brain of the subject.

Methods for imaging/detecting microtubules in vivo can be used to diagnose/monitor neurological disorders or diseases, or predispositions to neurological disorders or diseases.

The present methods for imaging microtubules may provide images of the location of microtubules and serve as a guide to a surgeon. In one embodiment, the surgeon is a neurosurgeon operating on the brain of a subject.

Diseases

The present compounds/compositions may be used in the diagnosis/identification, prophylaxis and/or treatment of diseases/disorders related to the function of microtubules. In one embodiment, the compounds/compositions are used in methods to diagnose a disease/disorder related to the function of microtubules. In another embodiment, the compounds/compositions are used in methods to diagnose predisposition to a disease/disorder related to the function of microtubules. Alternatively, the compounds/compositions are used in methods to monitor the course of, or treatment thereof, a disease/disorder related to the function of microtubules in a subject. Thus, whether a therapeutic regimen or treatment aimed at ameliorating the cause of the disease, or the disease process itself, is effective, can be determined by monitoring/detecting/imaging microtubules at suspected sites of disease (e.g., the brain).

The diseases that can be evaluated or treated using the present compounds or compositions include neurological disorders such as degenerative neurological disorders, neuropsychiatric disorders, and brain injury, as well as vascular diseases and cancer.

Degenerative neurological disorders include, neurodegenerative disease, such as stroke, Alzheimer's disease (AD), Pick's disease, Lewy body dementia (LBD), amyotrophic lateral sclerosis (ALS), Huntington's disease, Frontotemporal Degeneration (FTD), progressive supranuclear palsy (PSP) and corticobasal degeneration (CBD), Hereditary Spastic Paraplegia (HSP), and Huntington's disease (HD) or temporal lobe epilepsy; a pain disorder, including neuropathic pain or cancer pain; psychotic disorders such as addiction, alcoholism, schizophrenia, major depressive disorder (MDD) and bipolar disorder (BPD); a developmental disorder such as autism, a movement disorder, such as Parkinson's disease (PD), Mlultiple sclerosis (MS); brain injuries such as TBI, CTE and spinal cord injury (SCI).

Cancers that can be evaluated using the radiolabeled compounds for imaging, include, but are not limited to, nervous system cancers, such as a malignant glioma (e.g., astrocytoma, anaplastic astrocytoma, glioblastoma multiforme), retinoblastoma, pilocytic astrocytoma (grade I), meningiomas, metastatic brain tumors, neuroblastoma, pituitary adenomas, skull base meningiomas, and skull base cancer, lung cancer, ear, nose and throat cancer, leukemia, colon cancer, melanoma, pancreatic cancer, mammary cancer, prostate cancer, breast cancer, hematopoietic cancer, ovarian cancer, basal cell carcinoma, biliary tract cancer; bladder cancer; bone cancer; breast cancer, cervical cancer; choriocarcinoma; colon and rectum cancer; connective tissue cancer, cancer of the digestive system; endometrial cancer; esophageal cancer; eye cancer; cancer of the head and neck; gastric cancer; intra-epithelial neoplasm; kidney cancer; larynx cancer; leukemia including acute myeloid leukemia, acute lymphoid leukemia, chronic myeloid leukemia, chronic lymphoid leukemia; liver cancer; lymphoma including Hodgkin's and Non-Hodgkin's lymphoma; myeloma; fibroma, neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas.

In certain embodiments, besides showing affinity to microtubules (binding to microtubules), the present compound also possesses affinity to one or more receptor tyrosine kinases (RTKs), including, but not limited to, VEGFR2, PDGFR, and EGFR. Non-limiting examples of such compounds include, compounds of Formulas (II) or (II') or their salts; compounds selected from the group consisting of:

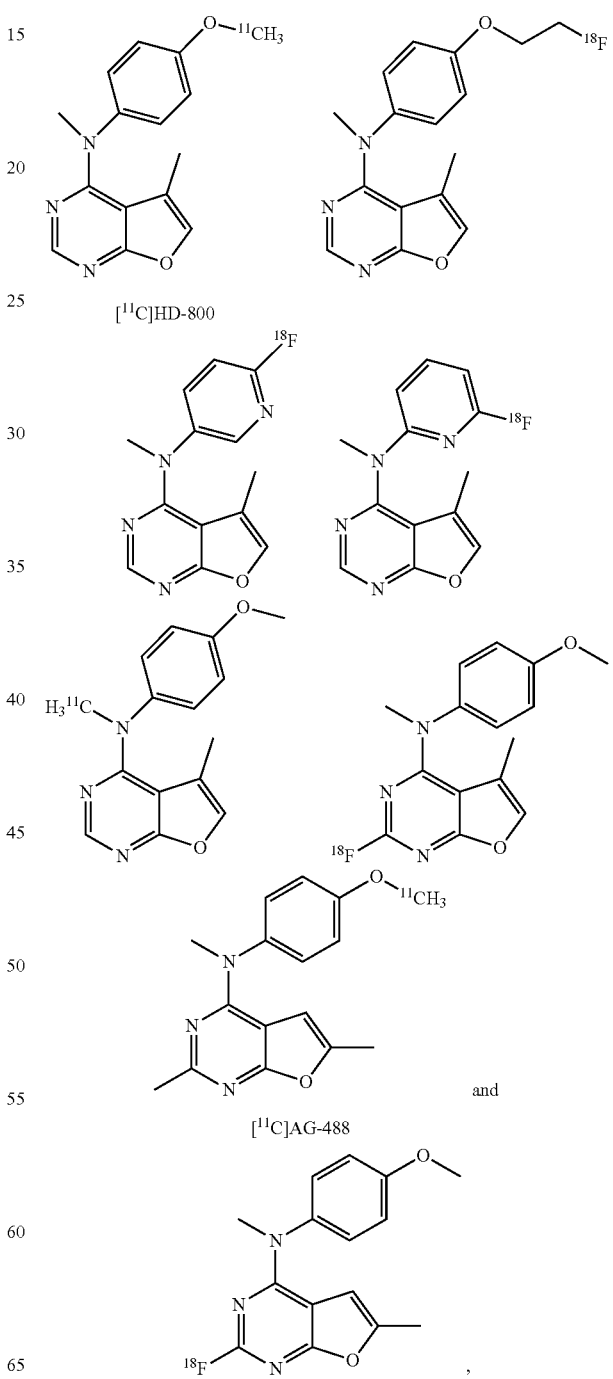

or their sails; compounds of Formulas (V) or (V') or their salts; and compounds

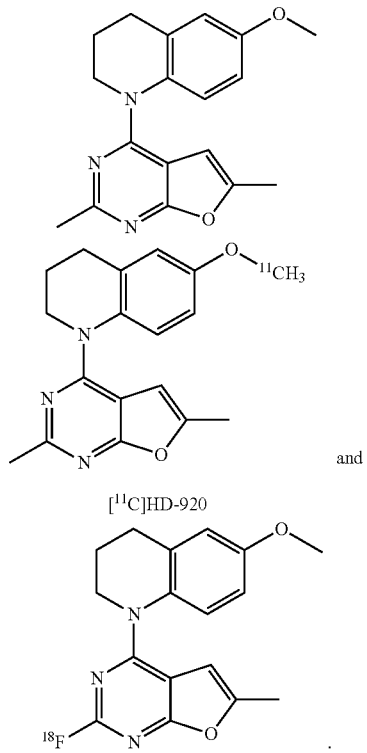

[¹¹C]HD-920 and

For example, HD-800 is more potent than the VEGFR2-binding agent sunitinib (IC50=9.3 nM for HD-800 vs. 18.9 nM for sunitinib). AG-488 has affinity to VEGFR2 similar to that of sunitinib. See, Devambatla et al., Design, synthesis and preclinical evaluation of 5-methyl-N4-aryl-furo[2,3-d]pyrimidines as single agents with combination chemotherapy potential, Bioorganic & Medicinal Chemistry Letters 28 (2018) 3085-3093. Compound HD-920 is a potent EGFR-binding agent (IC$_{50}$=3.4 nM) with microtubule-binding activity. See Zhng et al, The design, synthesis and biological evaluation of conformationally restricted 4-substituted-2,6-dimethylfuro[2,3-d]pyrimidines as multi-targeted receptor tyrosine kinase and microtubule inhibitors as potential antitumor agents, Bioorganic & Medicinal Chemistry Letters 23 (2015) 2408-2423.

The inhibitions of RTKs, specifically growth factor receptors, are positively correlated with microtubule loss in at least some neurodegeneration diseases, cancer and brain injury. In certain embodiments, a compound possessing affinities to both microtubules and RTK inhibits tumor cells better than an agent binding to only microtubules or only to one or more RTKs. In certain embodiments, an imaging agent possessing affinities to both microtubules and RTK shows better signal-to-noise ratio under diseased conditions. The higher signal-to-noise ratio is also useful for diagnosis of diseases.

Dosage Ranges

The radiolabeled compounds have high specific activity. In one embodiment, the invention provides radiolabeled compounds having a specific activity that is greater than about 100 Ci/micromole. In certain embodiments, the specific activity is from about 500 to about 1,000 Ci/mmol; about 1,000 to about 2,000 Ci/mmol; about 2,000 to about 3,000 Ci/mmol; about 3,000 to about 4,000 Ci/mmol; about 4,000 to about 5,000 Ci/mmol; or greater than 5,000 Ci/mmol; wherein any of the aforementioned ranges may be combined and/or overlap, and wherein the lower and/or upper limits of any of the aforementioned ranges may combined as appropriate.

The amount of the radiolabeled compound that is effective as an imaging agent to detect microtubules in a subject can be determined using standard clinical and nuclear medicine techniques. In addition, in vitro or in vivo testing can optionally be employed to help identify optimal dosage ranges. The precise dose to be employed will also depend on certain factors and should be decided according to the judgment of the practitioner and each subject's circumstances in view of published clinical studies. Suitable imaging-effective dosage amounts, however, range from about 0.01 mCi to about 30 mCi; about 2 mCi to about 30 mCi; about 10 to about 30 mCi or preferably from about 2 mCi to about 5 mCi. In some embodiments, the radiolabeled compounds will have a specific activity of >100 Ci/μmol at the time of administration to ensure a low injected mass and adequate counts for imaging. The imaging-effective dosage amounts refer to total amounts administered; that is, if more than one dose of a radiolabeled compound is administered, the imaging-effective dosage amounts correspond to the total amounts administered.

Kits

The present disclosure also provides for a kit comprising the present compound/composition. Kits include package(s) (e.g., vessels) comprising the present compounds or compositions. The present compound/composition may be present in unit dosage forms.

Examples of pharmaceutical packaging materials include, but are not limited to, bottles, tubes, inhalers, pumps, bags, vials, containers, syringes, bottles, and any packaging material suitable for a selected formulation and intended mode of administration and treatment.

Kits can contain instructions for administering the present compound/composition to a subject, a cell, a plurality of cells, a tissue, or an organ. Kits also can comprise instructions for uses of the present compound/composition. Kits can contain labeling or product inserts for the compound/composition. The kits also can include buffers for preparing solutions for carrying out the present methods. The instruction of the kits may state that the compound/composition can be used in a method of imaging or detecting microtubules or other targets in a subject, a cell, a plurality of cells, a tissue, or an organ, where the present composition or compound is administered to the subject, a cell, a plurality of cells, a tissue, or an organ (or the present composition or compound contacts a cell, a plurality of cells, a tissue, or an organ). The instruction may state that present composition or compound can be used to treat a neurological disorder in a subject.

Subjects include mammals, preferably humans, but can also be an animal such as dogs and cats, farm animals such as cows, pigs, sheep, horses, goats and the like, and laboratory animals (e.g., rats, mice, monkeys, baboons, guinea pigs, and the like).

The following are examples of the present disclosure and are not to be construed as limiting.

Example 1 Synthesis of Unlabeled MPC-6827 and Radiosynthesis of [11C]MPC-8627

Synthesis of MPC-6827 (1) is accomplished via appropriate modifications of a previous report.[20]

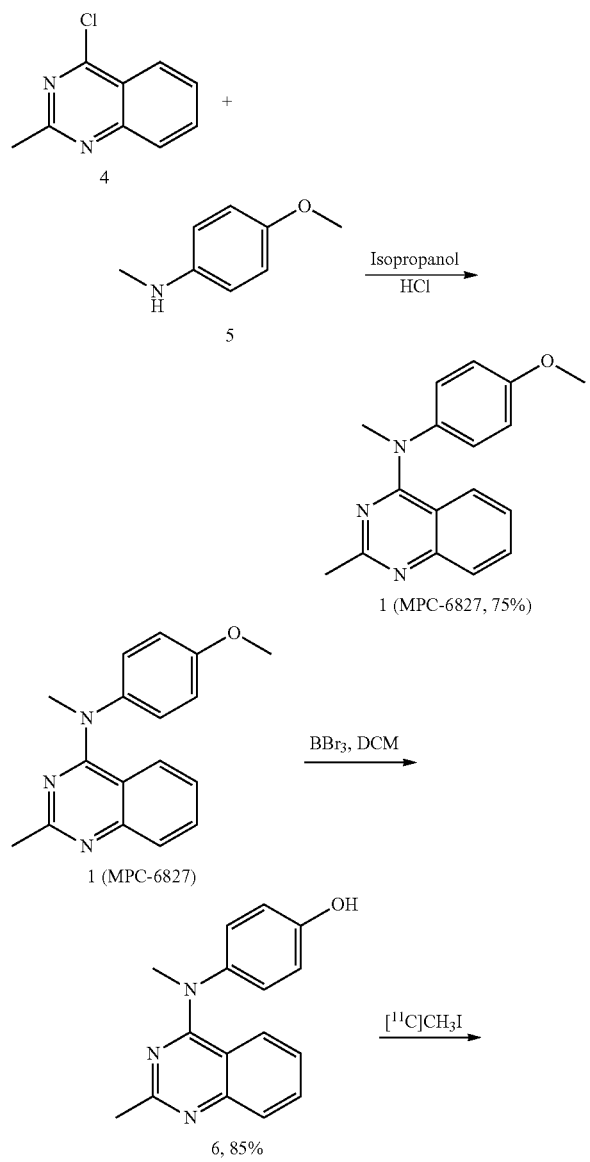

Compound 6 and N-desmethyl analogue 9 may be synthesized alternatively as follows.

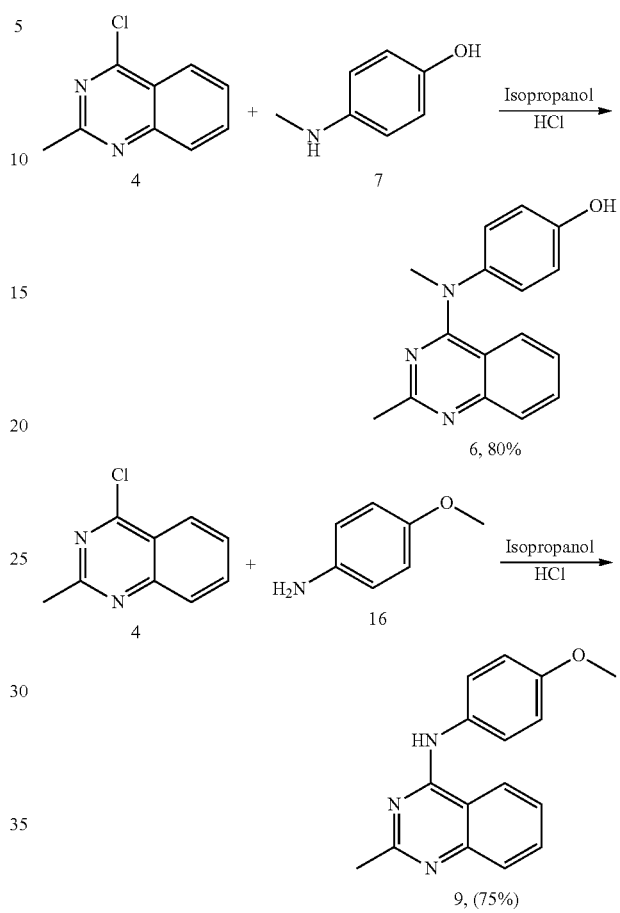

Desmethyl-MPC-6827 (6): 2 mL anhydrous dichloromethane was added to an argon charged reaction vessel containing MPC-6827 (85 mg, 0.3 mmol) at 0° C. 1M solution of $BBr_3$ in dichloromethane (1 mL) was added dropwise to it at 0° C. The solution was stirred for 1 h at room temperature. An aliquot of reaction mixture was quenched with methanol, performed analytical HPLC and conformed complete conversion of MPC-6827. The reaction was quenched by dropwise addition of methanol (1 mL) at 0° C., diluted with water (5 mL), extracted with 50 mL of dichloromethane (2×25 mL) followed by 50 mL of ethyl acetate (2×25 mL). The combined organic extracts were washed with brine, dried over anhydrous $MgSO_4$. Solvent was evaporated under reduced pressure and the residue obtained was washed with ice cold hexane to obtain compound 6 (70 mg, 85%) as a yellow solid. 6: $^1H$ NMR (400 MHz, $CD_3OD$) δ: 2.7 (s, 3H, $CH_3$), 3.7 (s, 3H, $CH_3$), 6.8 (m, 3H), 7.1 (m, 3H), 7.6 (m, 2H); HRMS (EI+) calculated for: $C_{16}H_{16}N_3O$: 266.1293; Found: 266.1294.

Alternative synthesis of compound 6. To a solution of 4-chloro-2-methylquinazoline (4, 90 mg, 0.5 mmol) and 4-(methylamino)phenol (7, 70 mg, 0.575 mmol) in 2 mL of anhydrous isopropanol (IPA) added 2 drops of concentrated HCl and the reaction mixture was stirred at room temperature overnight. The yellow precipitate was collected by filtration, washed with cold isopropanol, and dried under vacuum to afford compound 6 (105 mg, 80%) as yellow solid. Analytical data of compound 6 is identical with the product obtained using previous method.

Synthesis of 9: To a solution of 4-chloro-2-methylquinazoline (4, 90 mg, 0.5 mmol) and anisol (16, 70 mg, 5.75 mmol) in 2 mL of anhydrous isopropanol (IPA) added 2 drops of concentrated HCl and the reaction mixture was stirred at room temperature overnight. The yellow precipitate was collected by filtration, washed with cold isopropanol, and dried under vacuum to afford compound 9 (95 mg, 75%) as yellow solid.

9: $^1$H NMR (400 MHz, DMSOd6) δ 2.5 (3H, s, CH$_3$), 3.8 (3H, s, CH$_3$), 6.9 (2H, d), 7.6 (2H, d), 7.6 (2H, m), 7.9 (1H, m), 8.1 (1H, d); HRMS (EI+) calculated for: $C_{16}H_{16}N_3O$: 266.1317; Found: 266.1293.

The radiochemical synthesis of [$^{11}$C] MPC-6827 was optimized and automated on aGE-FX2MeI/FX2M radiochemistry module by alkylating the desmethyl-MPC6827 precursor (6) with [$^{11}$C] MeI in DMF using NaOH. [$^{11}$C] MPC-6827 was produced with a radiochemical yield (RCY) of 40%, in >99% radiochemical purity and a specific activity of 2+0.5 Ci/μmol (decay corrected to end of synthesis (EOS)). The radioligand was stable in 5% ethanol-saline formulation for 4 h and the log $P_{oct/wat}$ was estimated as 3.8 by shake flask method [15]. MPC-6827 did not show binding to a panel of kinases [8-11]. Except for histamine 4 receptor (H4R, Ki=155 nM), MPC-6827 did not exhibit any significant affinity (Ki=>10 μM) for a variety of brain targets (Table 1).

TABLE 1

Affinity and selectivity of MPC-6827

| Targets | Affinity (nM) | Targets | Affinity (nM) |
|---|---|---|---|
| Microtubule | 1.5[9] | CB2 | >10,000 |
| 5-HT1A | >10,000 | D1, D2 | >10,000 |
| 5-HT1B | >10,000 | D3, | >10,000 |
| 5-HT1D | >10,000 | D4 | >10,000 |
| 5-HT1E | >10,000 | KAR | >10,000 |
| 5-HT2A | >10,000 | D4 | >10000 |
| 5-HT2B | >10,000 | D5 | >10,000 |
| 5-HT2C | >10,000 | DAT | >10,000 |
| 5-HT3 | >10,000 | DOR | >10,000 |
| 5-HT7 | >10,000 | EP | >10,000 |
| Adenosine | >10,000 | GABA | >10,000 |
| α1A-1C | >10,000 | H4 | >10,000 |
| α2A | >10,000 | HERG | >10,000 |
| α2B | >10,000 | KOR | >10,000 |
| α2C | >10,000 | M | >10,000 |
| β1 | >10,000 | H3, H4 | >10,000 |
| β2 | >10,000 | MDR1 | >10,000 |
| β3 | >10,000 | H1 | >10,000 |
| BZP | >10,000 | H2 | 155 |
| Ca++ channel | >10,000 | MOR | 6,479 |
| AMPA | >10,000 | mGluR | >10,000 |
| NET | >10,000 | NMDA | >10,000 |
| NK | >10,000 | SERT | >10,000 |
| Sigma1 | 426 | Sigma2 | >10,000 |
| Na+ Channel | >10,000 | NT1 | >10,000 |
| CB1 | >10,000 | I | >10,000 |
| mGluRs | >10,000 | VMAT | >10,000 |
| NOP | >10,000 | NMDA | >10,000 |
| PBR | >10,000 | NT | >10,000 |
| Oxytocin | >10,000 | PKC | >10,000 |
| Smoothened | >10,000 | V1-2 | >10,000 |

Figure 2:
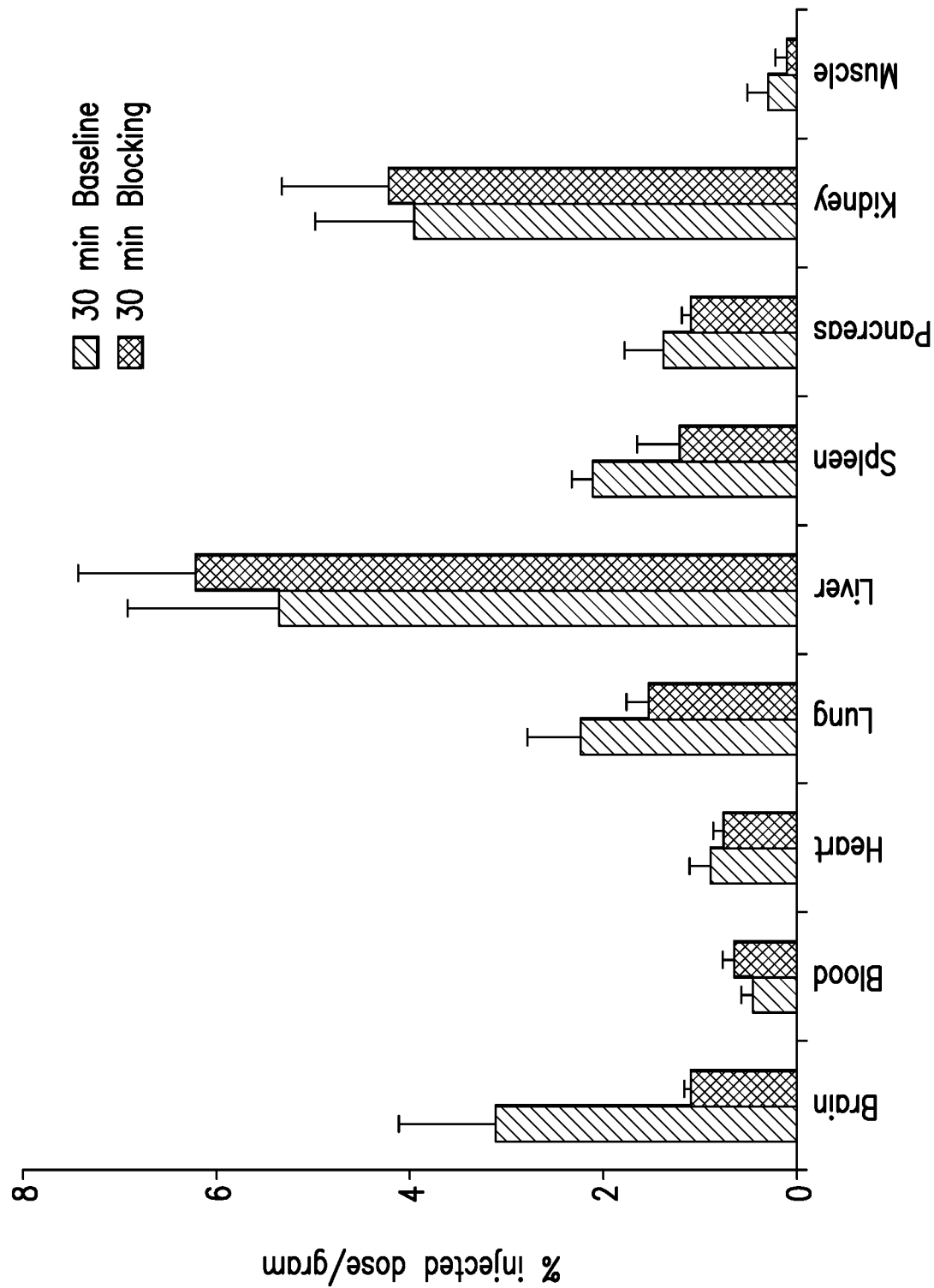
FIG. 2. Blocking biodistribition of [$^{11}$C]MPC-6827 in male white mice (n=3) at 30 min.
Figure 3:
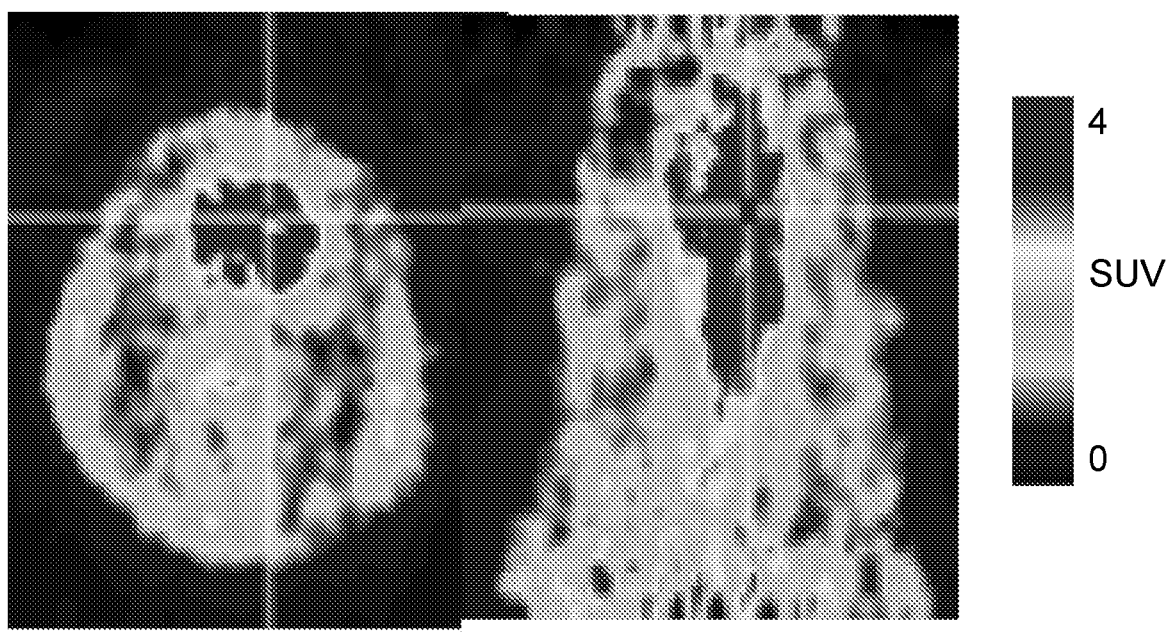
FIG. 3. Sum of the 0-60 minute microPET images of [$^{11}$C]MPC-6827 in rat brain (cross lines represent center of brain).
Figure 4:
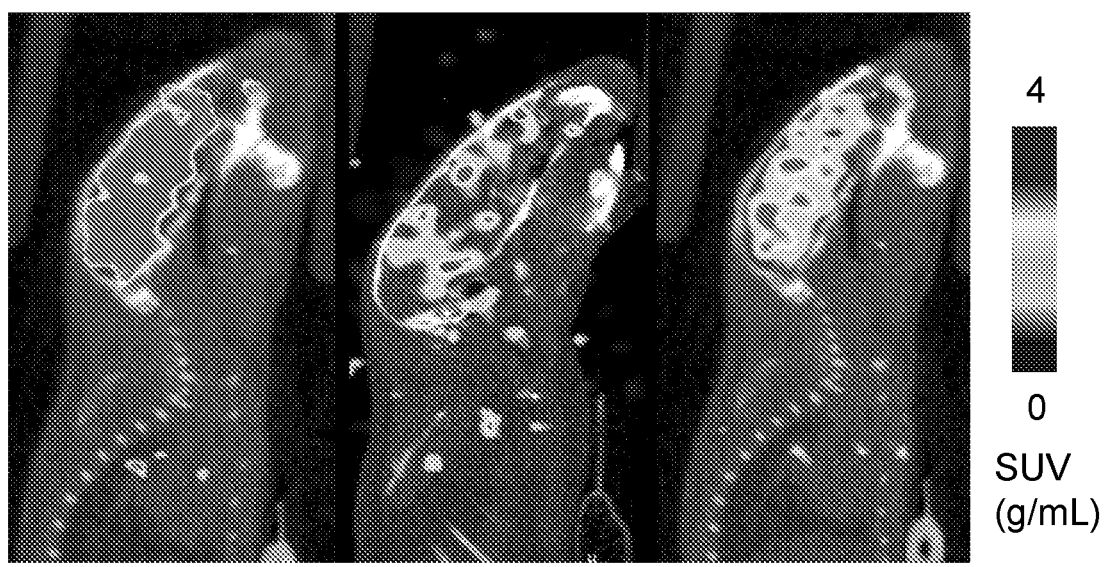
FIG. 4. microPET sagittal images of [$^{11}$C]MPC-6827 in mouse brain (left: baseline; middle: blocking with 5 mg/kg MPC-6827; right: blocking with 5 mg/kg HD-800).

MT: microtubule; 5-HT: 5-hydroxytryptamin; A: adenosine; a: alpha; 0: beta; BZP: benzodiazepine; AMPA: R-amino-3-hydroxy-5-methyl-4-isoxazolepropionic acid; CB: cannabinoid; D: dopamine; DAT: dopamine transporters; DOR: delta opioid receptors; EP: prostanoid receptors: GABA: gamma-amino butyric acid; H: histamine; hERG: human ether-a-go-go; KA: Kainate; KOR: kappa opioid receptors; M: muscarinic; MDR: multidrug resistance; MOR: mu opioid receptor; mGluR: metabotropic glutamate receptors; NMDA: N-methyl-D-aspartic acid; NK: neurokinin; NET: norepinephrine transporter; NT: neurotrophin; PKC: Protein kinase C; SERT: serotonin transporter; V: vasopressin; VMAT: vesicular monoamine transporter Biodistribution and In Vivo Imaging of [$^{11}$C] MPC-6827, [$^{11}$C]HD-800 and [$^{18}$F]FEMPC-6827 in Mice Biodistribution of [$^{11}$C] MPC-6827 in white male mice indicated that radioligand penetrated the BBB and was retained in the brain (FIG. 1). The time-activity curves were expressed in g/mL normalized to the injected dose corrected for weight, to obtain standardized uptake values (SUVs). The brain SUV of [$^{11}$C] MPC-6827 is higher than that of the established brain PET/periphery PET tracers. The heart, blood and muscles also show binding to [$^{11}$C] MPC-6827 and are consistent with known distribution of MTs in these organs. The liver, spleen, pancreas and kidney exhibit high uptake of the tracer. The lungs show higher uptake up to 30 minutes, followed by washout. 70% specific binding in brain was established at 30 minutes prior to the injection of radiotracer with 5 mg/kg MPC-6827 (FIG. 2) in mice. MicroPET studies in rat indicated BBB penetration and excellent retention of [$^{11}$C]MPC-6827 in brain (FIG. 3). MicroPET studies in nude mice also show excellent brain uptake (FIG. 4, left) and the uptake was blocked with pre-administration with 5 mg/kg MPC-6827 and 5 mg/kg of HD-800 (FIG. 4, middle and right).

Figure 5A:
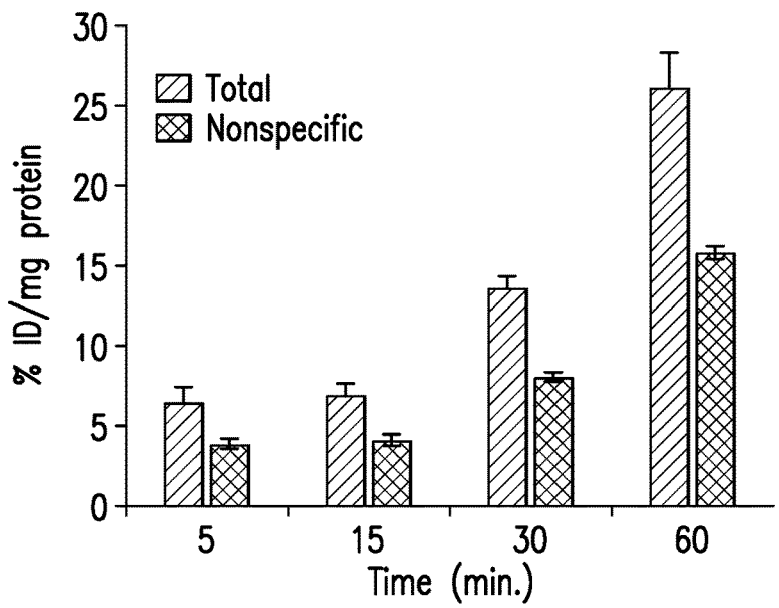
FIG. 5A. Uptake of [$^{11}$C]MPC-6827 in glioblastoma (GBM) U251 cells.
Figure 5B:
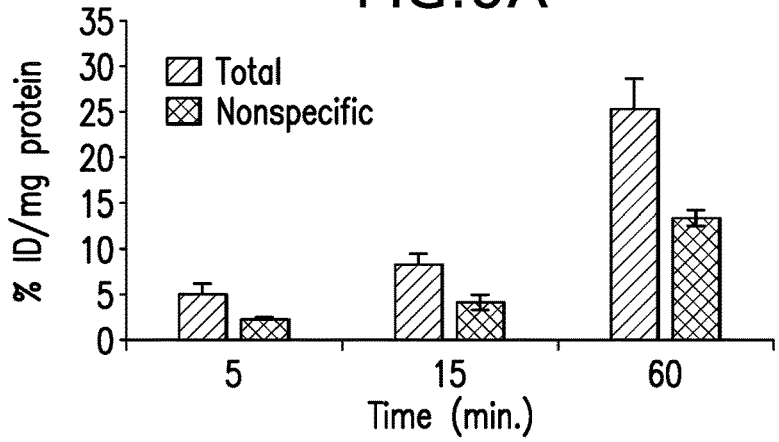
FIG. 5B. Uptake of [$^{11}$C]MPC-6827 in GBM PDX cells.
Figure 5C:
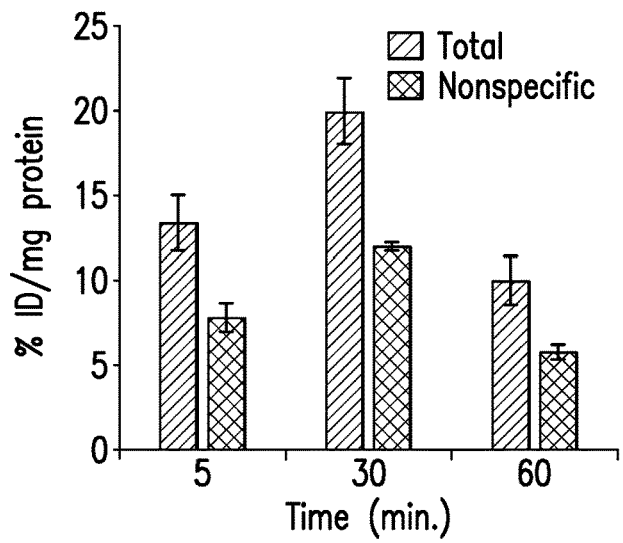
FIG. 5C. Uptake of [$^{11}$C]MPC-6827 in prostate cancer PC3 cells.

Proof of concept of radioligand binding in cancer has been demonstrated by excellent uptake and specific binding by in vitro cell uptake studies in glioblastoma (GBM) U251 cells, glioblastoma PDX and prostate cancer (PC3) cells (FIGS. 5A-5C).

Figure 6:
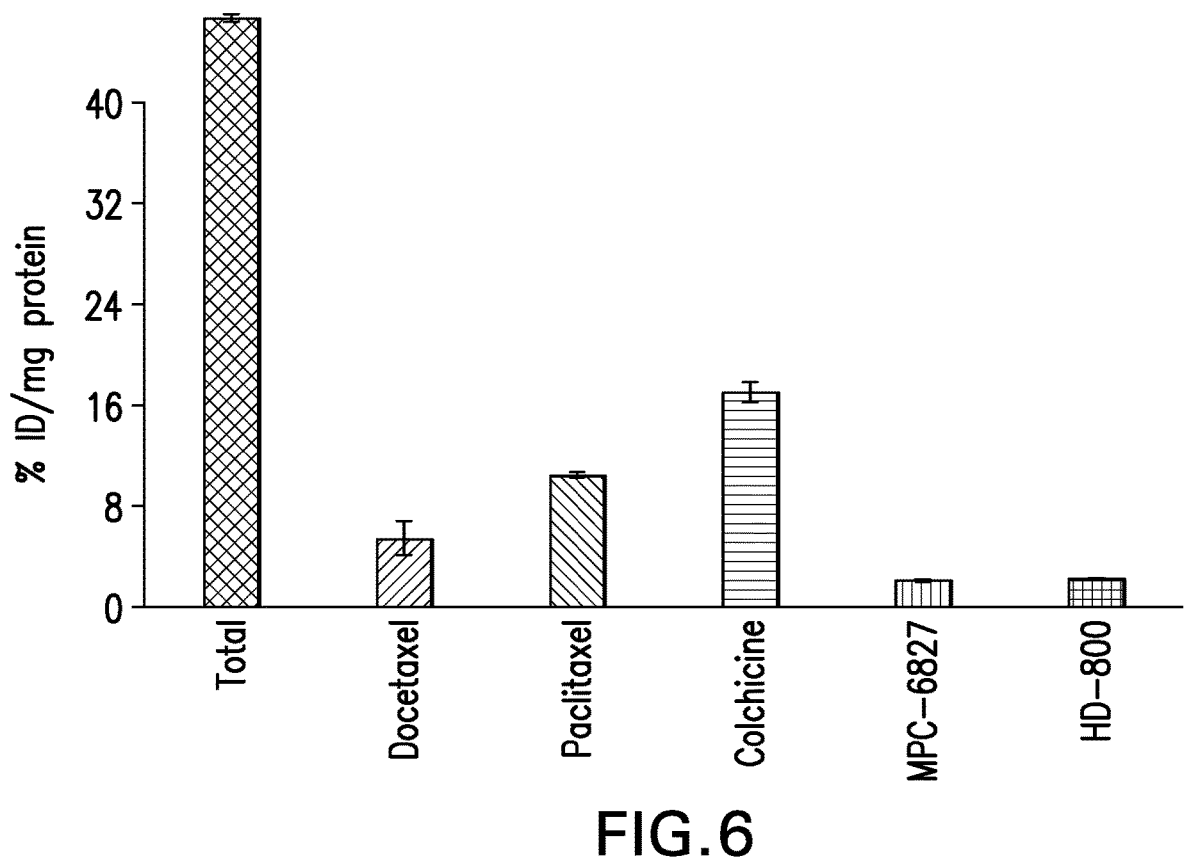
FIG. 6. Uptake of [$^{11}$C]MPC-6827 in MD3-MB-231 cells.

Cell uptake studies show [$^{11}$C]MPC-6827 exhibit equilibrium binding in MDA-MB-231 cells at 60-minute incubation time. [$^{11}$C]MPC-6827 showed 88%, 78%, 65%, 95%, and 95% specific binding with 5 μM each of docetaxel, paclitaxel, colchicine, MPC-6827 and MTA HD-800 (FIG. 6). Cell uptake studies with MDA-MB-231 cells showed [$^{11}$C]MPC-6827 binds to taxane and colchicine binding sites of microtubules (MTs). These results are consistent with the previous reports of photoaffinity and radioligand displacement studies showing MPC-6827 compete with paclitaxel and colchicine, but not with vinblastine.[9]

Figure 7:
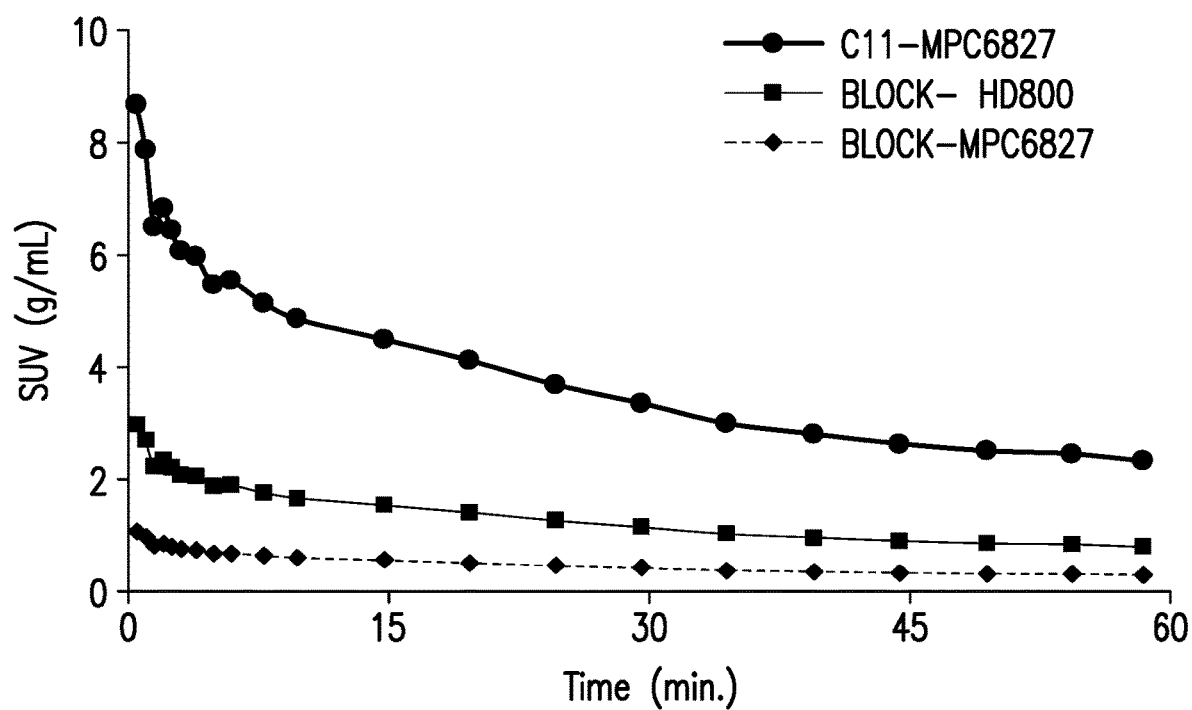
FIG. 7. Time activity curves of [$^{11}$C]MPC-6827 in mice.

In vivo binding of [$^{11}$C]MPC-6827 in athymic nude male mice show the radioligand penetrates the blood brain barrier (BBB) with excellent retention in the mouse brain (FIG. 7). Brain activity was substantially blocked by the i.v. administration of 5 mg/kg unlabeled MPC-6827 and HD-800, indicating specific binding of [$^{11}$C]MPC-6827 to brain MT. Radioligand binding in thyroid gland, is also displaced during the blocking experiments.[21-23]

Figure 10:
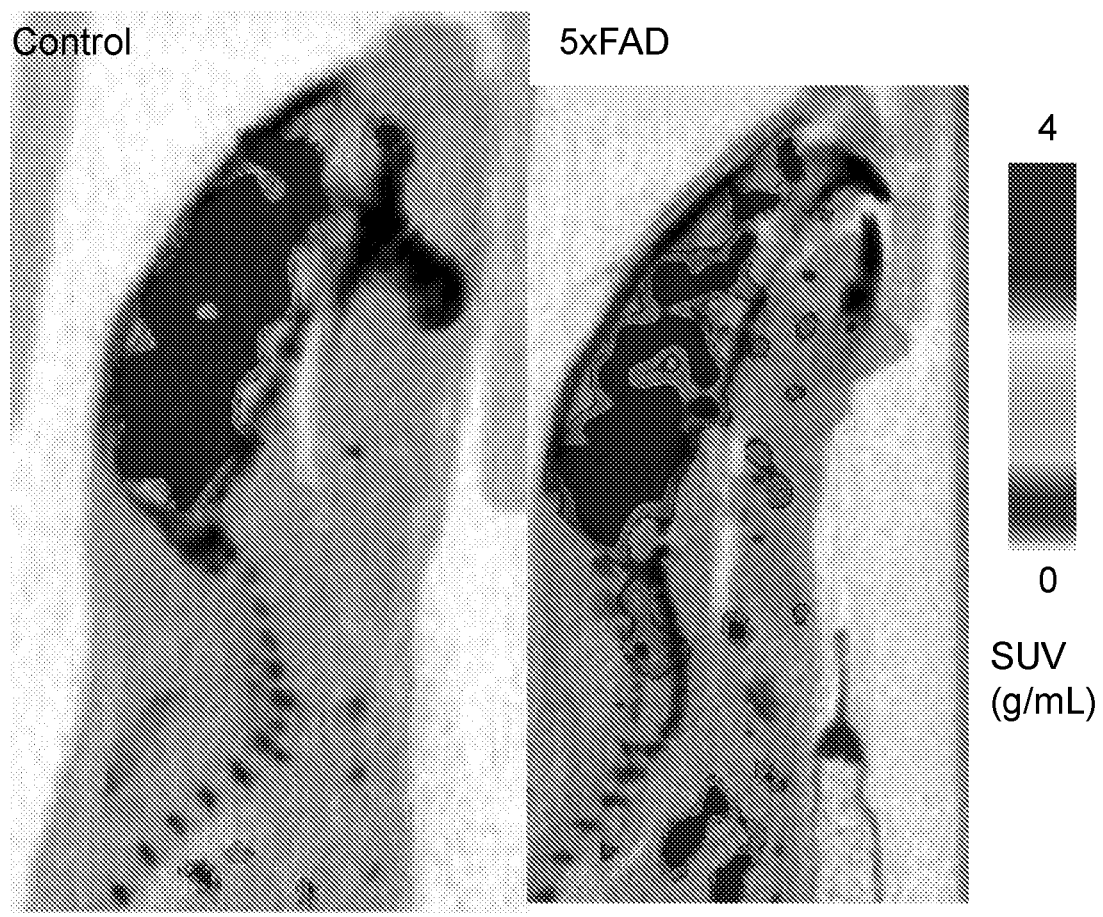
FIG. 10. MicroPET images of [$^{11}$C]MPC-6827 in AD animal model 5×FAD.
Figure 11:
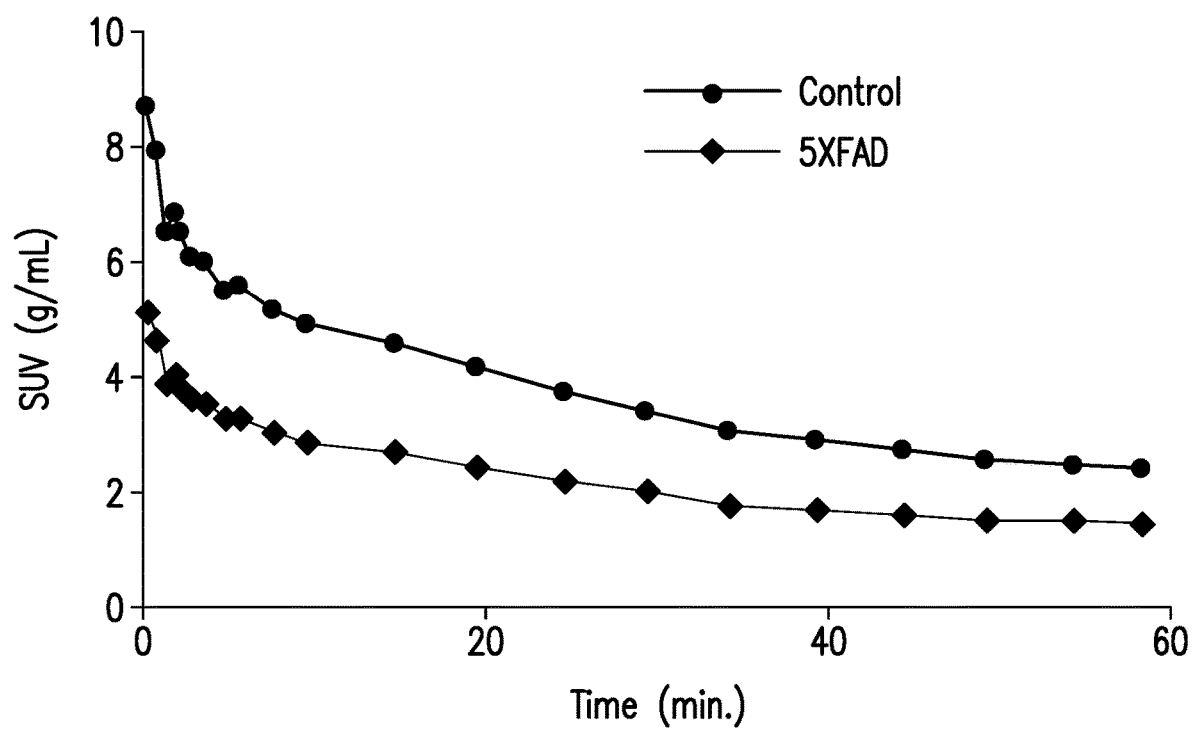
FIG. 11. Time activity curves of [$^{11}$C]MPC-6827 in AD animal model 5×FAD.

In vivo imaging of [$^{11}$C]MPC-6827 in amyloid overexpressing 5×FAD-AD mice (15 month-old) show 40% lower binding of radiotracer in the whole brain model in comparison to the wild type controls (FIGS. 10 and 11). The tracer binding in frontal and mid brain regions show significant lower binding than whole brain in comparison to wild type mice. These results offer [$^{11}$C]MPC-6827 as a promising imaging agent in AD patients.

Figure 12:
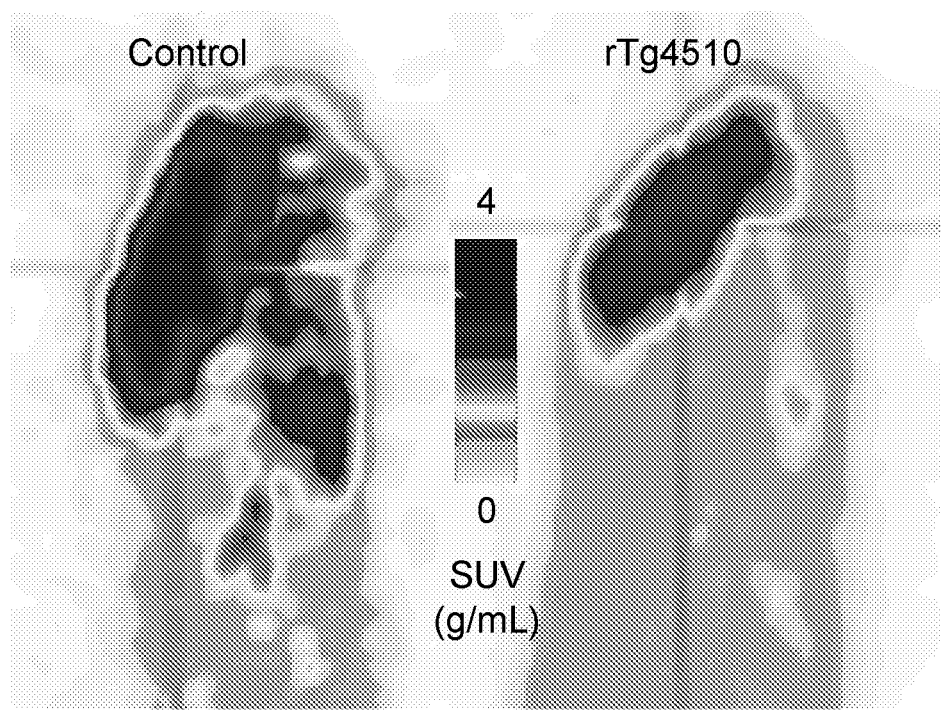
FIG. 12. MicroPET images of [$^{11}$C]MPC-6827 in AD animal model rTg4510.
Figure 13:
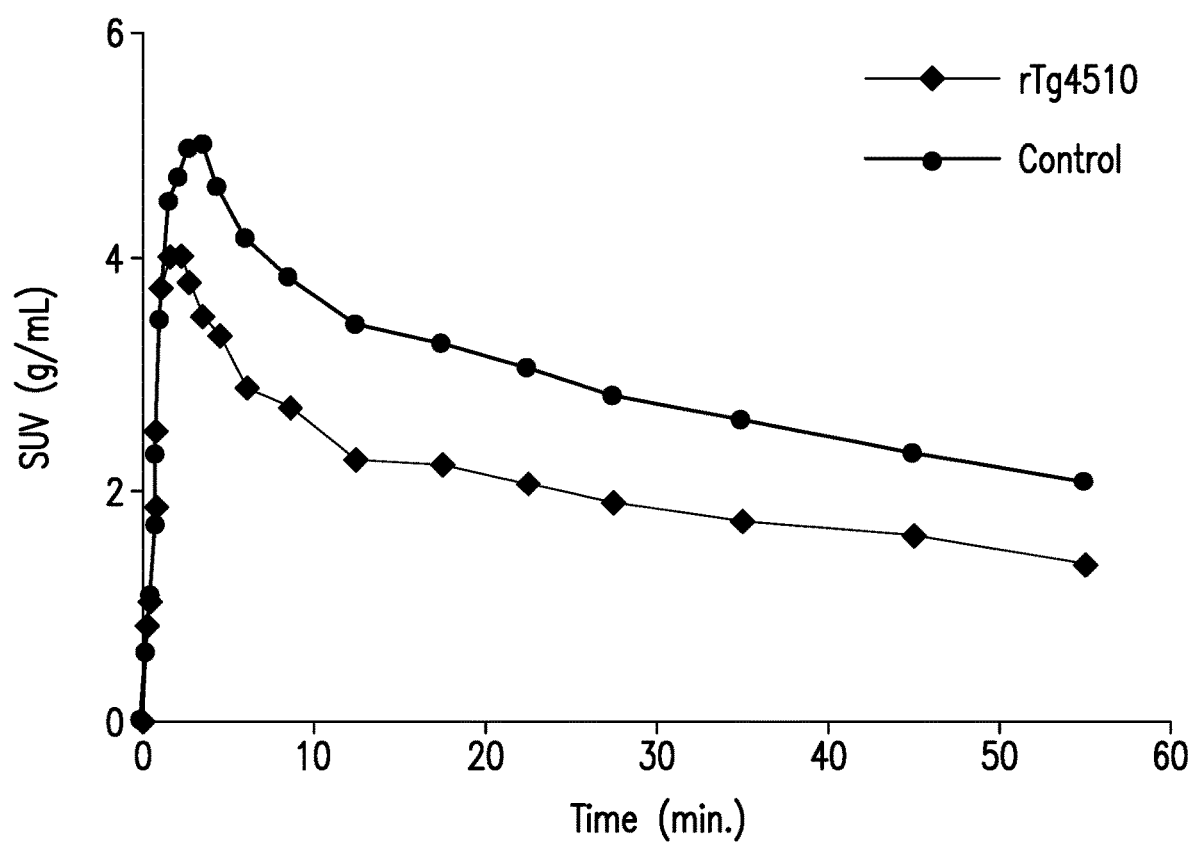
FIG. 13. Time activity curves of [$^{11}$C]MPC-6827 in AD animal model rTg4510.

MicroPET studies with 9-month old, tau-overexpressing rTg4510 mice (Alzheimer disease-tau pathology) show ~35% lower binding of [$^{11}$C]MPC-6827 brain activity in comparison to the control mice (FIGS. 12 and 13). These data shows that [$^{11}$C]MPC-6827 can be an imaging agent for AD and related tauopathies.

Example 2 Synthesis of Unlabeled HD-800 and Radiosynthesis of [¹¹C]HD-800
Synthesis of HD-800 (2) is accomplished via appropriate modifications of a previous report.[12]
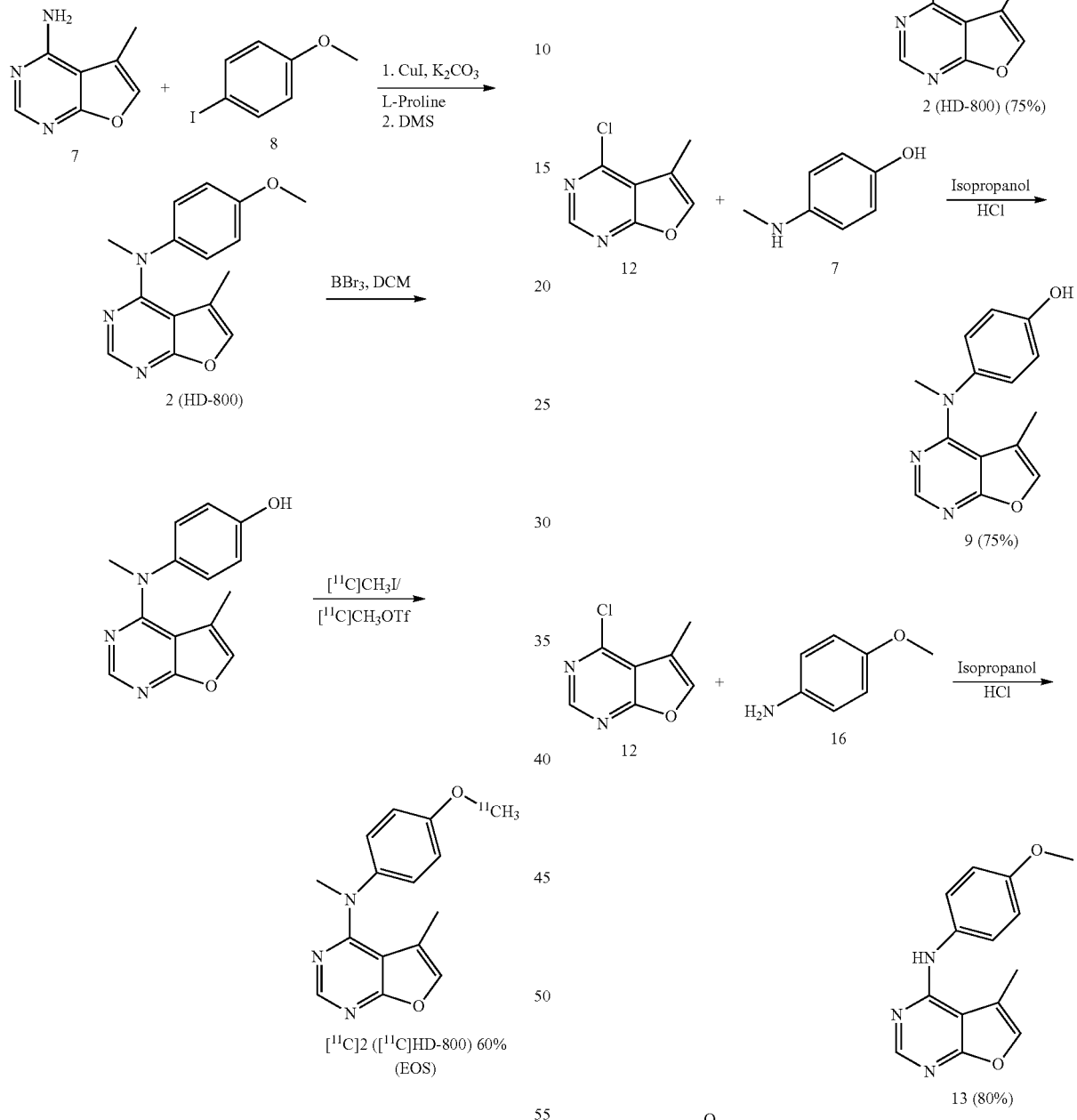
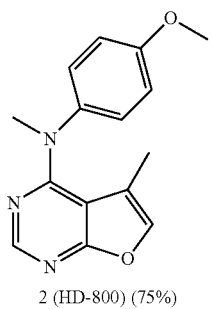
Alternatively, 2, 9 and 13 are synthesized by HCl mediated coupling reactions as show below.
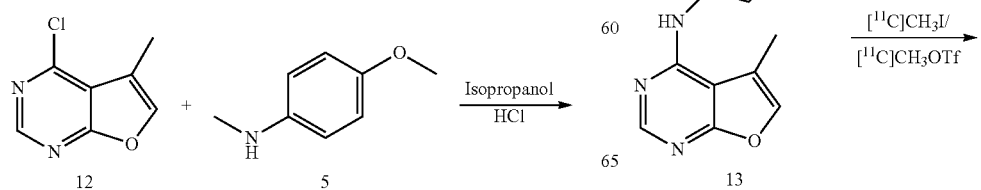

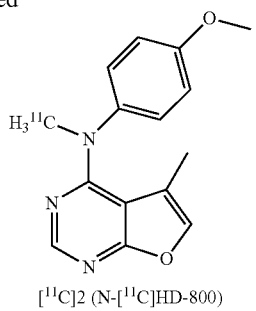

[11C]2 (N-[11C]HD-800)

Desmethyl-HD-800 (9): 2 mL anhydrous dichloromethane was added to an argon charged reaction vessel containing HD-800 (81 mg, 0.3 mmol) at 0° C. 1M solution of BBr3 in dichloromethane (1 mL) was added dropwise to it at 0° C. The solution was stirred for 1 h at room temperature. An aliquot of reaction mixture was quenched with methanol, performed analytical HPLC and conformed complete conversion of HD-800. The reaction was quenched by dropwise addition of methanol (1 mL) at 0° C., diluted with water (5 mL), extracted with 50 mL of dichloromethane (2×25 mL) followed by 50 mL of ethyl acetate (2×25 mL). The combined organic extracts were washed with brine, dried over anhydrous $MgSO_4$. Solvent was evaporated under reduced pressure and the residue obtained was washed with ice cold hexane to obtain compound 9 (65 mg, 90%) as a brown solid. 9: $^1$H NMR (400 MHz, $CD_3OD$) δ: 1.15 (s, 3H, $CH_3$), 3.7 (s, 3H, $CH_3$), 6.8 (d, 2H), 7.2 (d, 2H), 7.5 (s, 1H), 8 (s, 1H); HRMS (EI+) calculated for: $C_{14}H_{14}N_3O_2$: 256.1090; Found: 256.1086.

Alternative synthesis of compound 2. To a solution of 4-chloro-5-methylfuro[2,3-d]pyrimidine (12, 85 mg, 0.5 mmol) and 4-methoxy-N-methylaniline (5, 80 mg, 5.75 mmol) in 2 mL of anhydrous isopropanol (IPA) added 2 drops of concentrated HCl and the reaction mixture was stirred at room temperature overnight. The brown precipitate was collected by filtration, washed with cold isopropanol, and dried under vacuum to afford compound 2 (95 mg, 75%) as brown solid. Analytical data of compound 2 is identical with the product obtained using previous method.[12]

Alternative synthesis of compound 9. To a solution of 4-chloro-5-methylfuro[2,3-d]pyrimidine (12, 42.5 mg, 0.25 mmol) and 4-(methylamino)phenol (7, 35 mg, 0.28 mmol) in 2 mL of anhydrous isopropanol (IPA) added 2 drops of concentrated HCl and the reaction mixture was stirred at room temperature overnight. The brown precipitate was collected by filtration, washed with cold isopropanol, and dried under vacuum to afford compound 9 (52 mg, 75%) as yellow solid. Analytical data of compound 9 is identical with the product obtained using previous method.

Apart from tubuline affinity, compound 2 did not exhibit binding affinity to a variety of brain targets (Table 2).

TABLE 2

| Affinity of HD-800 to brain targets. | | | |
|---|---|---|---|
| Targets | Affinity (nM) | Targets | Affinity (nM) |
| MT | IC50 3.2[12] | 5-HT1A-1E | >10,000 |
| MT | GI50 < 10[12] | | |
| 5-HT2A-2C | >10,000 | 5-HT3-7 | >10,000 |
| 5-HT2A-2C | >10,000 | A | |
| 5-HT3-7 | >10,000 | α1A-1C | >10,000 |
| α2A-2C | >10,000 | β1-3 | >10,000 |

TABLE 2-continued

| Affinity of HD-800 to brain targets. | | | |
|---|---|---|---|
| Targets | Affinity (nM) | Targets | Affinity (nM) |
| AMPA | >10,000 | BZP | >10000 |
| Ca+ channel | >10,000 | CB1, CB2 | >10,000 |
| D1-D5 | >10,000 | DAT | >10,000 |
| DOR | >10,000 | H1 | >10,000 |
| H2 | >10,000 | H3, H4 | >10,000 |
| HERG | >10,000 | GABA | >10,000 |
| EP | >10,000 | I | >10,000 |
| KOR | >10,000 | KA | >10,000 |
| M | >10,000 | mGluR | >10,000 |
| MDR1 | >10,000 | MOR | >10,000 |
| NET | >10,000 | NK | >10,000 |
| NMDA | >10,000 | NOP | >10,000 |
| NT | >10,000 | Oxytocin | >10,000 |
| PBR | 2364 | PKC | >10,000 |
| SERT | >10,000 | Sigma1 | >10,000 |
| Sigma 2 | >10,000 | Na+ Channel | >10,000 |
| Smoothened | >10,000 | VMAT 1,2 | >10,000 |

Synthesis of 13: To a solution of 4-chloro-5-methylfuro[2,3-d]pyrimidine (12, 85 mg, 0.25 mmol) and anisole (16, 70 mg, 0.28 mmol) in 2 mL of anhydrous isopropanol (IPA) added 2 drops of concentrated HCl and the reaction mixture was stirred at room temperature overnight. The brown precipitate was collected by filtration, washed with cold isopropanol, and dried under vacuum to afford compound 13 (52 mg, 80%) as a brown solid. 13: $^1$H NMR (400 MHz, $CD_3OD$) δ: 2.4 (s, 3H, $CH_3$), 3.8 (s, 3H, $CH_3$), 6.9 (d, 2H), 7.4 (m, 2H), 7.7 (s, 1H); HRMS (EI+) calculated for: $C_{14}H_{14}N_3O_2$: 256.1084; Found: 256.1086.

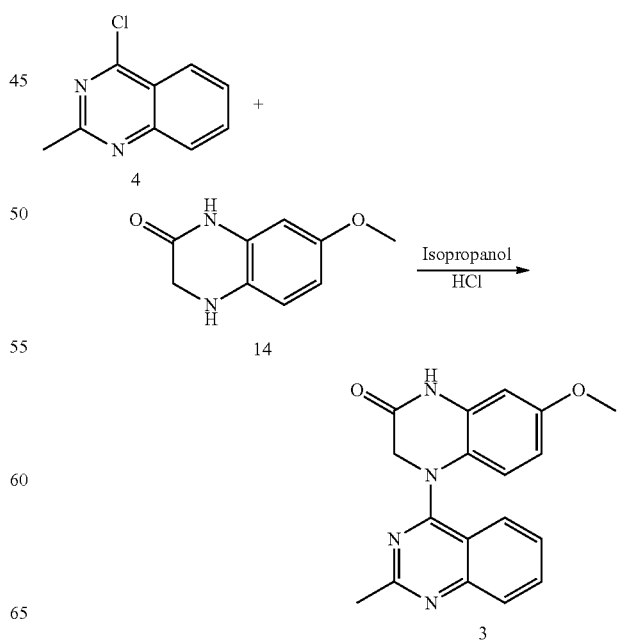

-continued

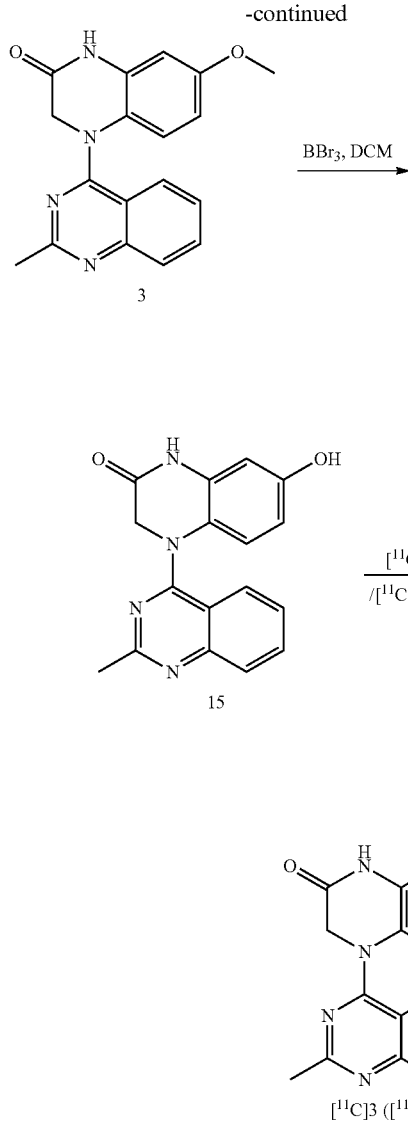

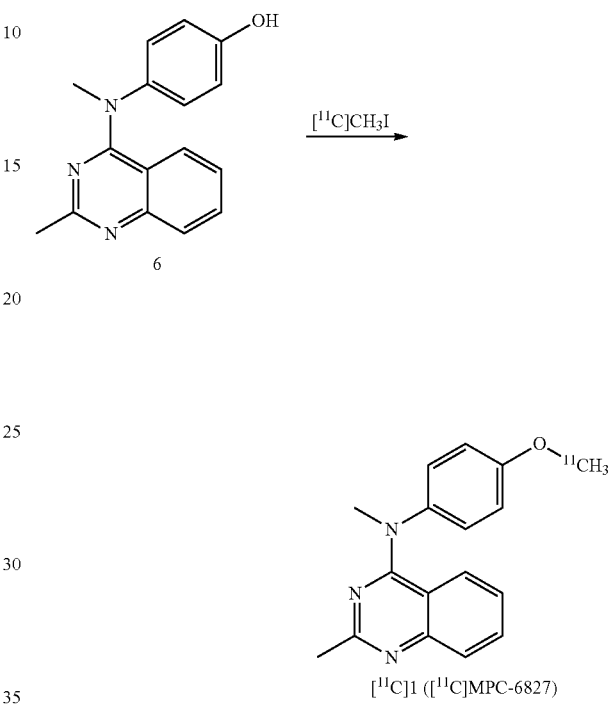

Synthesis of reference standard 3 can be achieved via a reported procedure [13] or via coupling of compound 4 with commercial 7-methoxy-3,4-dihydroquinoxalin-2(1H)-one (14). Compounds 2 and 3 are selective over a variety of kinases [13, 14]. The compounds 2 and 3 upon demethylation with BBr3 will afford the radiolabeling precursors 8 and 11. Radiolabeling of [$^{11}$C]2 ([$^{11}$C]HD-800) and [$^{11}$C]3 ([$^{11}$C] WX-132-18B) can be accomplished via methylation of corresponding phenolate using [$^{11}$C] MeI/[$^{11}$C] MeOTf.

HD-800 and WX-132-18B are established BBB penetrant MTAs with higher tumor growth inhibition (TGI) than paclitaxel and also exhibited anti-drug resistant properties in a variety of tumor xenografts [12-14].

Figure 8:
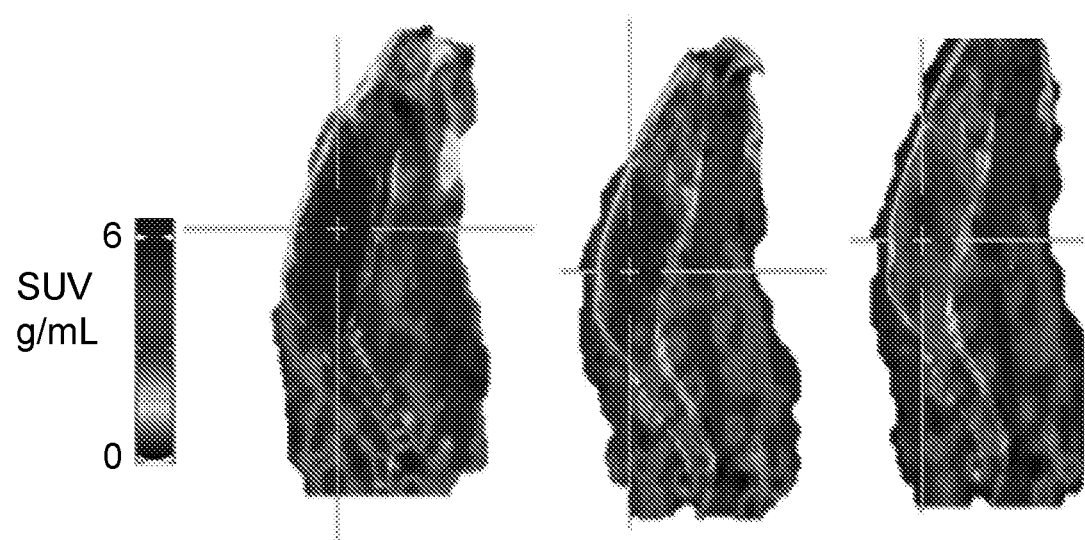
FIG. 8. MicroPET images of [$^{11}$C]HD-800 in mice.
Figure 9:
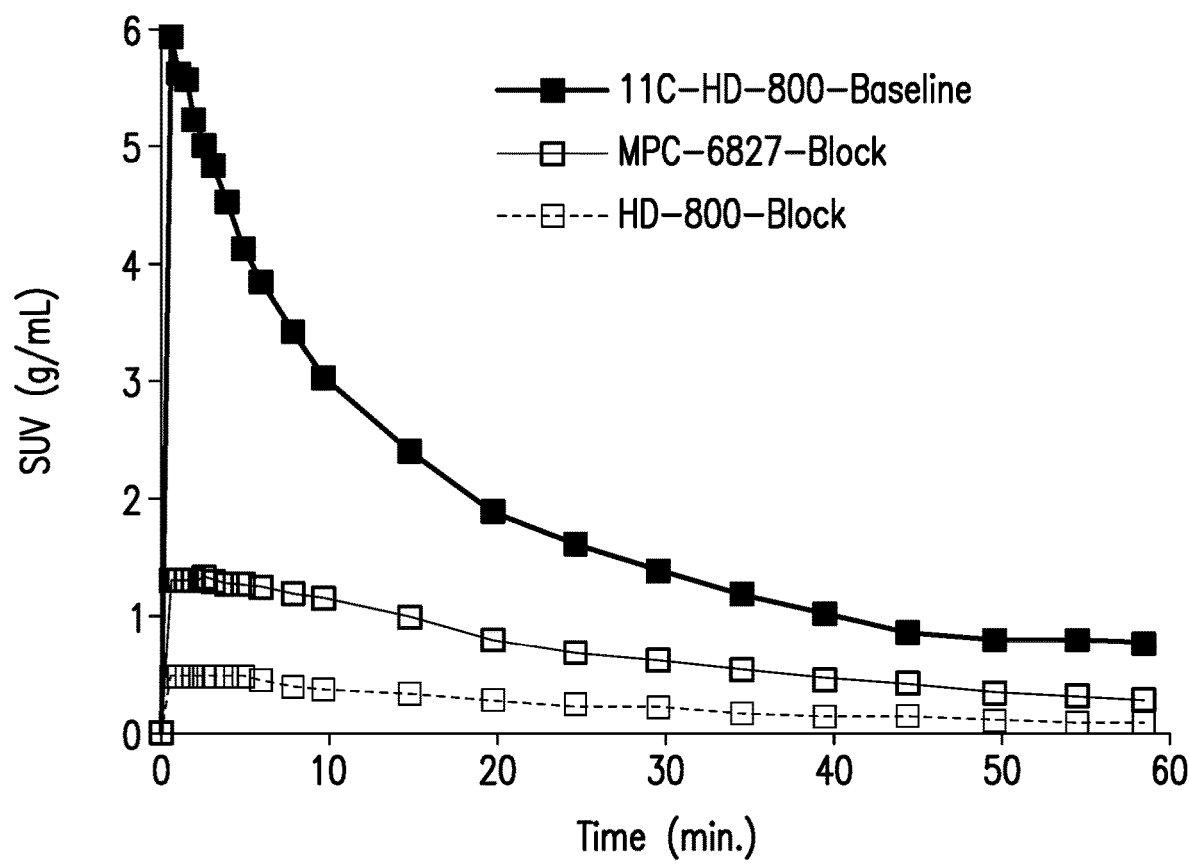
FIG. 9. Time activity curves of [$^{11}$C]HD-800 in mice.

As is evident from the microPET images (FIG. 8), [$^{11}$C]HD-800 penetrated the BBB followed by a homogeneous distribution in the mouse brain. Blocking with unlabeled MPC-6827 and HD-800 (5 mg/kg/i.v) 20 minute prior to radioligand administration indicates specific binding of radiotracer to brain MTs. Both blocking agents show significant decreasing activity of [$^{11}$C]HD-800 in the brain. Time activity curves (TACs) further confirm the washout of [$^{11}$C]HD-800 in mice brain and excellent specific binding with unlabeled HD-800 and MPC-6827 as blocking agents (FIG. 9).[23-24]

Example 3 Radiosynthesis of O-[$^{11}$C]MPC-6827

[$^{11}$C]MeI from FX2MeI module was bubbled to the reaction vial placed in FX2M module containing precursor 4 (~0.5-0.8 mg) in anhydrous DMF (0.6 mL) and 5N NaOH aqueous solution (10.0 µL) for ~5 min at room temperature. After the complete transfer of radioactivity, the sealed reaction vial was then heated at 80° C. for 5 min. The reaction mixture was quenched with HPLC mobile phase (1.0 mL) and injected onto a reverse-phase semi-preparative C18 Phenomenex ODS (250×10 mm, 10µ) HPLC column to purify [$^{11}$C]MPC6827. The isocratic HPLC mobile phase solution consisted of 60% acetonitrile, 40% 0.1 M aqueous ammonium formate buffer solution (pH 6.0-6.5) with UVλ@254 nm and a flow rate of 7.0 mL/min. The product [11C]MPC6827 (Rt=9.0-11.0 min) was collected and diluted with 100 mL deionized water, and passed through C18 SepPak cartridge (WAT036800, Waters, Milford, MA) to trap the radioactive product. [$^{11}$C]MPC6827 was then directly eluted from the cartridge with absolute ethanol (1.0 mL) and formulated with saline (10% ethanol in saline) into a sterile vial through a sterile 0.22 µm pyrogen-free filter for further animal studies and quality control analysis. [$^{11}$C]MPC6827 purity was assessed using an analytical Phenomenex C18 HPLC column (250×4.6 mm, 5µ) and with UV λ@254 nm. The mobile phase (1.0 mL/min) consisted of 60% acetonitrile and 40% 0.1M aqueous ammonium formate pH 6.0-6.5 solution. [$^{11}$C]MPC6827 showed a retention at 7.1 min, and authentication of the product was performed with co-injection of the non-radioactive standard MPC6827, which demonstrated a similar retention times.

Example 4 Radiosynthesis of N-[¹¹C]MPC-6827

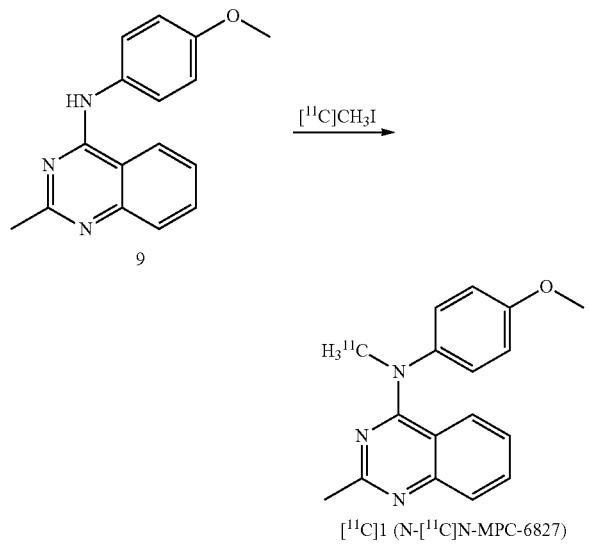

N-desmethyl-MPC-6827 (9, ~0.5 mg) was dissolved in 500 μL of DMF in a capped 1 mL V-vial. ~1 mg of NaH was added the precursor solution at 0° C. under argon atmosphere and the resultant solution was allowed to stand for 2 minutes in an ice bath. [¹¹C]CH₃I was transported into the reaction mixture over approximately 5 minutes at room temperature. At the end of the trapping, the product mixture was heated for 20 min at 100° C. The reaction mixture was allowed to cool, diluted with 0.5 mL of mobile phase and was directly injected into a semi preparative HPLC Column (Phenomenex ODS (250×10 mm, 10μ) to purify N-[¹¹C]MPC-6827. The product N-[¹¹C]MPC-6827 ($R_t$=9-11 min) was collected and diluted with 100 mL deionized water, and passed through C18 SepPak cartridge (WAT036800, Waters, Milford, MA) to trap the radiotracer N-[¹¹C]MPC-6827. Radioactive product was then eluted from the cartridge with absolute ethanol (1.0 mL) and formulated with saline (10% ethanol in saline). The final product N-[¹¹C]MPC-6827 (5-8% yield) was directly collected into a sterile vial through a sterile 0.22 μm pyrogen-free filter (Millipore Corp., Billerica, MA).

Example 5 Radiosynthesis of O-[¹¹C]HD-800

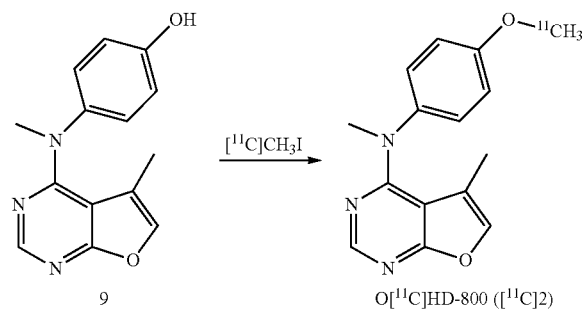

The precursor 11 (~0.5 mg) was dissolved in 500 μL of DMF in a capped 1 mL V-vial. 10 microL of TBAOH was added and the resultant solution was allowed to stand for 2 minutes. [¹¹C]CH₃I was transported into the reaction vial over approximately 5 minutes at room temperature. At the end of the trapping, the product mixture was heated for 5 min at 80° C. The reaction mixture was allowed to cool, diluted with 0.5 mL of mobile phase and was directly injected into a semi preparative HPLC Column (Phenomenex ODS (250×10 mm, 10μ, 60:40 acetonitrile and 0.1M ammonium formate, Flow rate: 10 mL/min; λ=254 nM) to purify [¹¹C]HD-800. The radioproduct [¹¹C]HD-800 ($R_t$=7-8 min) was collected and diluted with 100 mL deionized water, and passed through C18 SepPak cartridge (WAT036800, Waters, Milford, MA) to trap the radiotracer. Radioactive product was then eluted from the cartridge with absolute ethanol (1.0 mL) and formulated with saline (10% ethanol in saline). The final product [¹¹C]HD-800 (60% yield) was directly collected into a sterile vial through a sterile 0.22 μm pyrogen-free filter (Millipore Corp., Billerica, MA) for further studies and quality control analysis. [¹¹C]HD-800 purity was assessed using an analytical reverse phase Phenomenex ODS HPLC column (250×4.6 mm, 5μ) and UV detection set at 254 nm. The analytical mobile phase (2 mL/min) consisted of 60% acetonitrile and 40% 0.1M aqueous ammonium formate pH 6.0-6.5 solution.

Example 6 Radiosynthesis of N-[¹¹C]HD-800

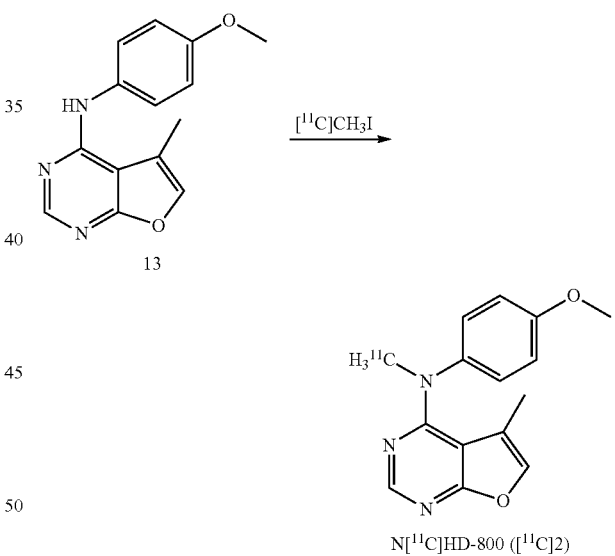

N-desmethyl-HD-800 (13, ~0.5 mg) was dissolved in 500 μL of DMF in a capped 1 mL V-vial. ~1 mg of NaH was added and the resultant solution was allowed to stand for 2 minutes in an ice bath under argon atmosphere. [¹¹C]CH₃I was transported into the reaction mixture over approximately 5 minutes at room temperature. At the end of the trapping, the product mixture was heated for 20 min at 100° C. The reaction mixture was allowed to cool, diluted with 0.5 mL of mobile phase and was directly injected into a semi preparative HPLC Column (Phenomenex ODS (250×10 mm, 10μ) to purify N-[¹¹C]HD-800, same as reported for O[¹¹C]HD-800. The radioproduct was obtained in 5-8% yield.

Example 7 Synthesis of FE-MPC-6827 and Radiosynthesis of [$^{18}$F]FE-MPC-6827 ([$^{18}$F]fluoroethyl-MPC-6827)

Synthesis of fluoroethylMPC-6827 (16)

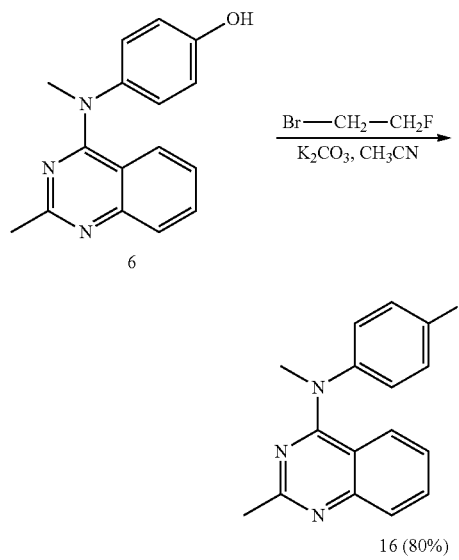

1-Bromo-2-fluoroethane (125 mg, 1 mmol) and potassium carbonate (160 mg, 1.15 mmol) were added to the solution of 6 (53 mg, 0.2 mmol) in dry CH$_3$CN (4 ml). The reaction mixture was heated at 80° C. for overnight. The reaction mixture was cooled to rt, filtered and evaporated under high vacuum. The residue was chromagraphed over silicagel using 2% methanol in CH$_2$Cl$_2$ to give the compound 16 as a pale-yellow solid (51 mg, 80%).

16: $^1$H NMR (400 MHz, CDCl$_3$) δ 7.7 (dd, 1H), 7.6 (m, 1H); 7.1 (m, 2H), 6.8 (m, 4H), 4.8 (m, 1H), 4.6 (m, 1H), 4.2 (m, 1H), 4.1 (m, 1H), 3.5 (3H, s, CH$_3$), 2.65 (3H, s, CH$_3$); HRMS Calcd for C$_{18}$H$_{19}$FN$_3$O (MH+): 311.1454; Found: 311.1468.

Table 3 indicate FEMPC-6827 did not exhibit affinity to a variety of brain targets.

TABLE 3

Affinity of FEMPC-6827 to brain targets.

| Targets | Affinity (nM) | Targets | Affinity (nM) |
| --- | --- | --- | --- |
| 5-HT1A-1E | >10,000 | 5-HT3-7 | >10,000 |
| 5-HT2A-2C | >10,000 | A | >10,000 |
| 5-HT2A-2C | >10,000 | α1A-1C | >10,000 |
| 5-HT3-7 | >10,000 | β1-3 | >10,000 |
| α2A-2C | >10,000 | BZP | >10000 |
| AMPA | >10,000 | CB1, CB2 | >10,000 |
| Ca+ channel | >10,000 | DAT | >10,000 |
| D1-D5 | >10,000 | H1 | 305 |
| DOR | >10,000 | H3, H4 | >10,000 |
| H2 | 2310 | GABA | >10,000 |
| HERG | >10,000 | I | >10,000 |
| EP | >10,000 | KA | >10,000 |
| KOR | >10,000 | mGluR | >10,000 |
| M | >10,000 | MOR | >10,000 |
| MDR1 | >10,000 | NK | >10,000 |
| NET | >10,000 | NOP | >10,000 |
| NMDA | >10,000 | Oxytocin | >10,000 |
| NT | >10,000 | PKC | >10,000 |
| PBR | 1592 | Sigma1 | 51 |
| SERT | >10,000 | Na+ Channel | >10,000 |
| Sigma 2 | 2464 | VMAT 1,2 | >10,000 |
| Smoothened | >10,000 | | |

Radiosynthesis of [$^{18}$F]FE-MPC-6827 ([$^{18}$F]Fluoroethy-MPC-6827)

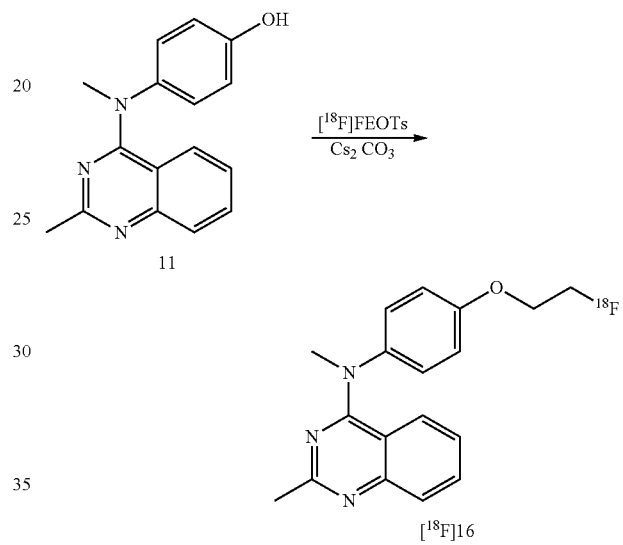

The [$^{18}$F]fluoroethyltosylate is added to a solution of 2 mg of 11 in 0.25 mL DMSO and heated for 30 minutes at 90° C. The crude product was diluted with 0.25 mL of acetonitrile and was directly injected into a semi preparative RP-HPLC (Phenomenex C18, 10×250 mm, 10) and eluted with acetonitrile: 0.1 M ammonium formate solution (45:55) at a flow rate of 10 mL/min. The precursor eluted after 3-4 minute during the HPLC analysis. The radioproduct fraction with a retention time of 9-10 minutes based on γ-detector was collected, diluted with 50 mL of deionized water, and passed through a C-18 Sep-Pak® cartridge. Reconstitution of the product in 1 mL of absolute ethanol afforded [$^{18}$F]16 (<5% radiochemical yield).

Figure 14:
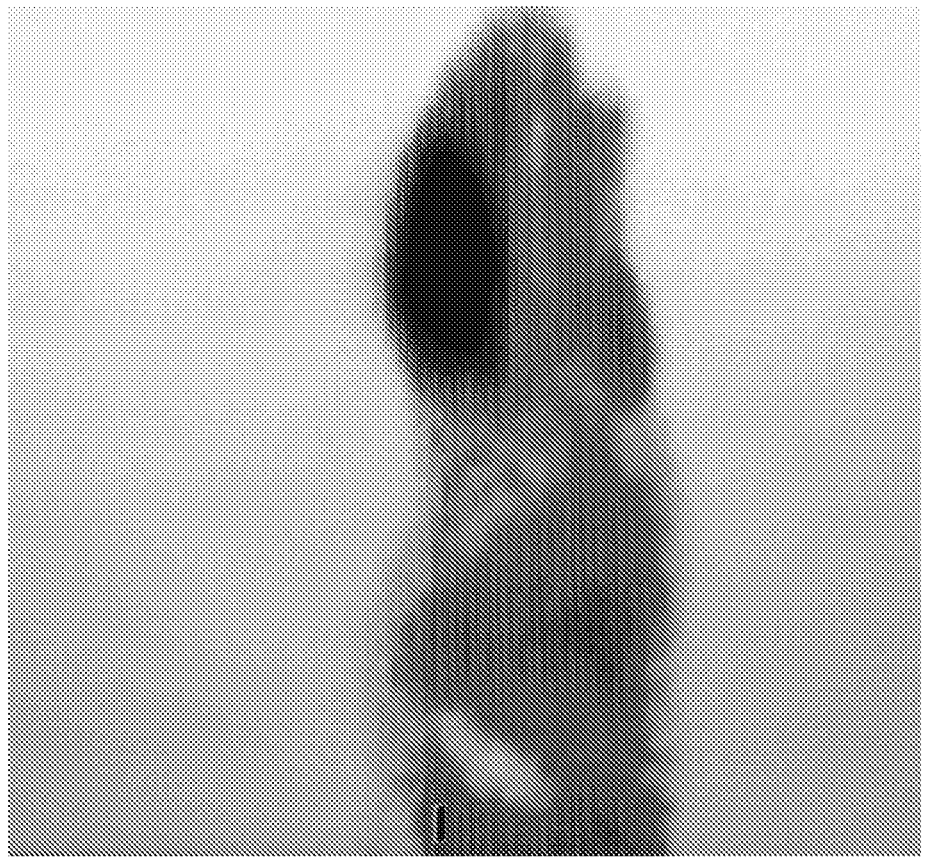
FIG. 14. MicroPET images of [$^{18}$F]FEMPC-6827 in mice.

MicroPET studies of [$^{18}$F]FEMPC-6827 in the mice brain indicate blood brain barrier penetration and accumulation in the brain (FIG. 14). The distribution pattern of [$^{18}$F]FEMPC-6827 in the mice brain is similar to that of [$^{11}$C]MPC-6827 and [$^{11}$C]HD-800.

Example 8 Alternative Radiosynthesis of [$^{18}$F]FE-MPC-6827 ([$^{18}$F]16)

Since the radiochemical yield of [$^{18}$F]16 was low as well as it is a 2 steps procedure in example 6, an one step sradiosynthesis of [$^{18}$F]16 was achieved by radiofluorination of compound 21.

a. Synthesis of Radiolabeling Precursor 2-(4-(methyl(2-methylauinazolin-4-yl)amino) phenoxy) ethyl 4-methylbenzenesulfonate (MPC-O-ethyltosylate)

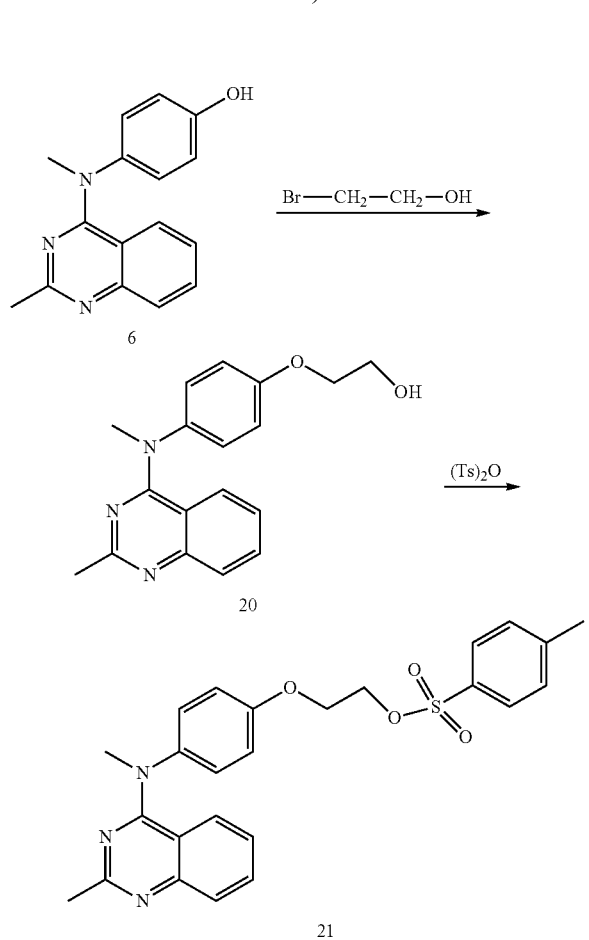

1-Bromo-2-ethanol (50 mg, 0.4 mmol) and potassium carbonate (140 mg, 1 mmol) were added to the solution of 6 (53 mg, 0.2 mmol) in dry DMF (5 ml). The reaction mixture was heated at 120° C. for overnight. The reaction mixture was cooled to RT, diluted with 5 mL water and extracted with ethyl acetate (2×25 mL). The combined ethyl acetate washed water, brine and evaporated under high vacuum. The residue was chromatographed over silicagel using methanol-dichloromethane to afford compound 20 as pale-yellow solid (51 mg, 80%). Compound 16 was used for tosylation reaction.

Tosyl anhydride (70 mg, 0.21 mmol) was added to a solution of 20 (51 mg, 0.16 mmol) containing 0.1 mL of trimethylamine in 5 mL dry dichloromethane. The reaction mixture was allowed to stirrer at RT for 4 h. After the complete conversion of compound 20 by TLC, the crude reaction was evaporated under high vacuum. The residue was chromatographed using ethyl acetate hexane to afford compound 21 as yellow solid (44 mg, 58%).

21: $^1$H NMR (400 MHz, CDCl$_3$) δ 7.9 (d, 2H), 7.8 (m, 1H); 7.6 (m, 1H), 7.4 (d, 2H), 7.2 (d, H), 7.0 (d, 2H), 6.9 (d, 2H), 4.4 (t, 2H), 4.2 (t, 2H), 3.6 (3H, s, CH$_3$), 2.75 (3H, s, CH$_3$), 2.5 (3H, s, CH$_3$); HRMS Calcd for $C_3H_{24}N_3O_5S$ (MH+): 454.1441; Found: 454.1427.

b. Radiosynthesis of [$^{18}$F]FE-MPC-6827

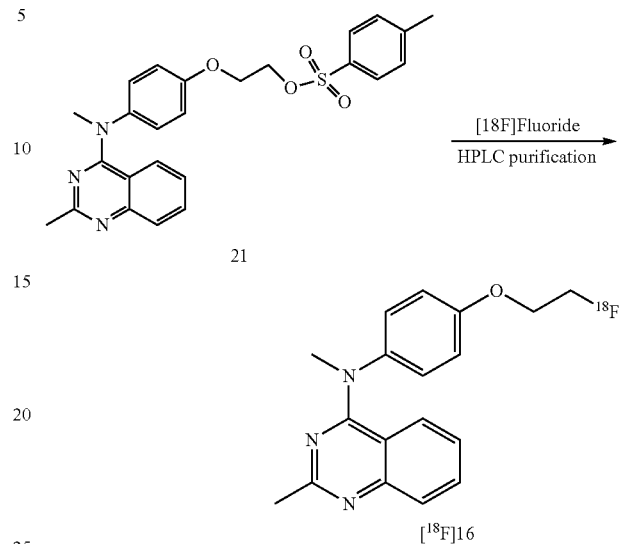

The precursor 21 (1-2 mg) in 500 μL of acetonitrile was added to azeotropically dried [$^{18}$F]fluoride. The reaction mixture was allowed to heat 20 minutes at 100° C. The reaction mixture was allowed to cool, diluted with 20 mL water and pass through a C18 Sepack. The Sepack was washed with 1 mL acetonitrile and was injected into a semipreparative HPLC system (Phenomenex ODS (250×10 mm, 10μ) to purify [$^{18}$F]FE-MPC-6827. HPLC mobile phase solution consisted of 50% acetonitrile, 50% 0.1 M aqueous ammonium formate solution (pH value 6.0-6.5) with a flow rate of 7.0 mL/min. The product [$^{18}$F]FE-MPC-6827 (R$_t$=~8 min) was collected and diluted with 100 mL deionized water, and passed through C18 SepPak cartridge to trap the radiotracer. Radioactive product was then eluted from the cartridge with absolute ethanol (1.0 mL) and formulated with saline (10% ethanol in saline) (40% radiochemical yield). The quality control analysis[$^{18}$F]FE-MPC-6827 was assessed using an analytical reverse phase Phenomenex ODS HPLC column (250×4.6 mm, 5μ) with mobile phase consisted of 60% acetonitrile, 40% 0.1 M aqueous ammonium formate solution (pH value 6.0-6.5) and a flow rate of 1.5 mL/min and retention time (~5.5 minute).

Example 9 Radiosynthesis of [$^{18}$F]18

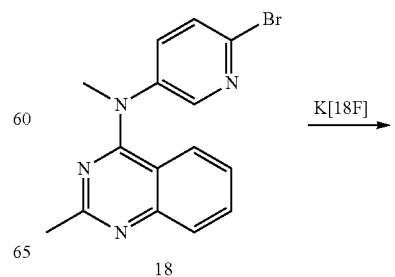

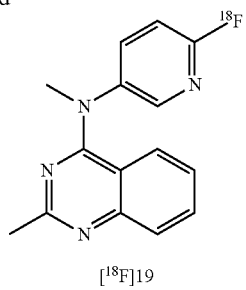

[18F]19

Radiochemistry

A solution of radiolabeling precursor 18 (2-3 mg) in DMSO (0.5 mL) was added to the azeotropically dried [$^{18}$F]KF/kryptofox/K$_2$CO$_3$. The mixture was heated at 150° C. for 30 minute or microwave irradiation for 5 minutes. The reaction mixture was allowed to cool, diluted with 50 mL deionized water, passed through a C-18 Sep-Pak® cartridge (Waters), washed with 20 mL water to remove unreacted [$^{18}$F]fluoride and other polar impurities. The crude radio-product was eluted with 1 mL of acetonitrile and injected on to a semipreparative RP-HPLC. The product fraction based on γ-detector was collected, diluted with 100 mL of deionized water, and passed through C-18 Sep-Pak® cartridge (Waters). Reconstitution of the product in 1 mL of absolute ethanol afforded [$^{18}$F]19.

Radiosynthesis of

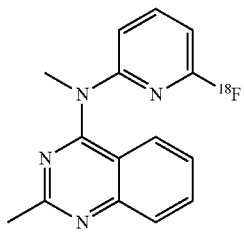 [SMILES: Cc1nc(N(C)c2cccc([18F])n2)c2ccccc2n1]

may be carried out following similar procedures.

Example 10 Synthesis of

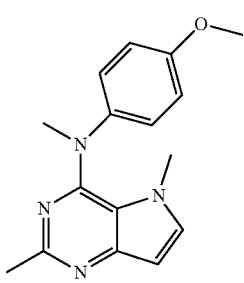

Acid catalyzed condensation of pyrrole 6 with acetonitrile lead to the pyrrolo[3,2-d]pyridimidine 7. Chlorination with POCl$_3$ generates 8. Nucleophilic displacements of 8 using N-methyl-p-anisidine and (4-methylthio)-N-methyl-aniline afford 1 and 4 respectively. Alkylation of the 5-N with appropriate alkyl halides results in

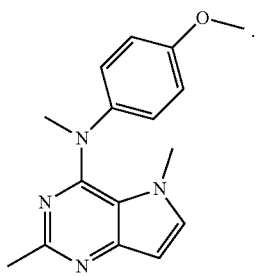

WO 2016/168637.

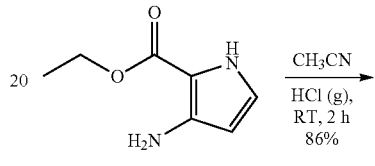

6

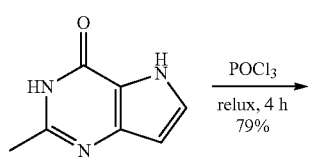

7

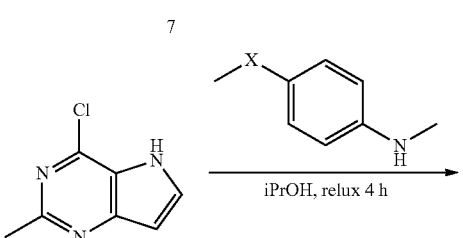

8

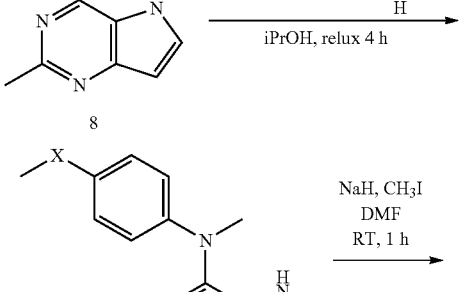

1 X = O 72%
4 X = S 65%

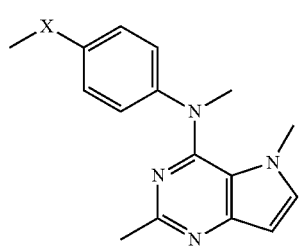

2 X = O 89%
5 X = S 80%

Example 10 Synthesis of

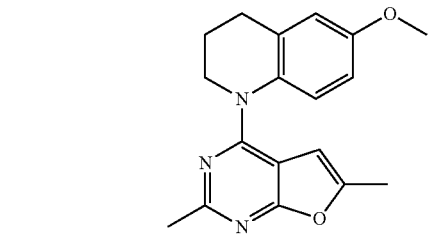

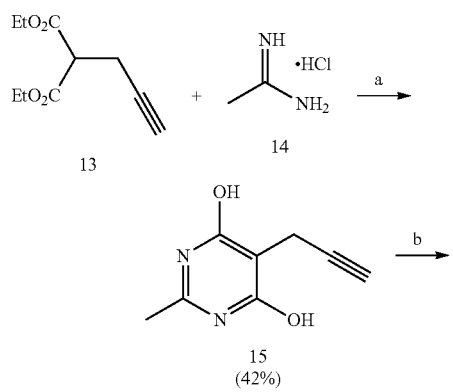

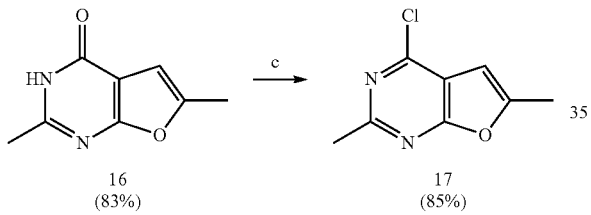

Reagents and Conditions:
(a) Na/MeOH/reflux, 24 h; (b) H$_2$SO$_4$ (conc.), rt, overnight; (c) POCl$_3$. reflux, 2 h The synthesis of 4-chloro-2,6-dimethylfuro[2,3-d]pyrimidine, compound 17. The synthesis of the intermediate, compound 17, is shown in the above scheme. A three-step reaction, starting from diethyl propargyl malonate compound 13, is employed in the synthesis of 4-chloro-2,6-dimethylfuro[2,3-d]pyrimidine, compound 17. The condensation of diethyl propargyl malonate compound 13 and acetamidine hydrochloride compound 14 is carried out as a route to pyrimidine compound 15. Intramolecular cyclization of compound 15 to the furo[2,3-d]pyrimidine compound 16 proceeds under H$_2$SO$_4$ (conc.) at room temperature. Chlorination of compound 16 with POCl$_3$ affords the 4-chloro-2,6-dimethylfuro[2,3-d]pyrimidine compound 17.

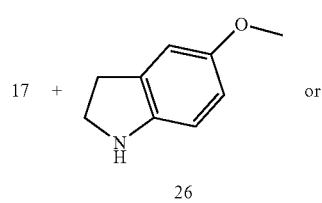

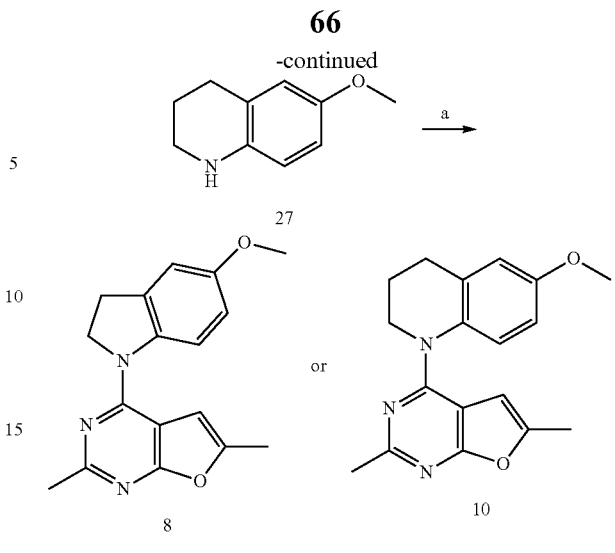

Reagents and Conditions:
(a) "BuOH. 1 drop of HCl (conc.), reflux

Under nucleophilic displacement condition, intermediate compound 17 reacts with compounds 27 at reflux in nBuOH and a catalytic amount of HCl to provide compound 10. WO 2016/100495.

Example 11 Radiosynthesis of [18F]FE-HD-800 (([$^{18}$F]fluoroethy-HD-800; [18F]22)

Synthesis of FEHD-800

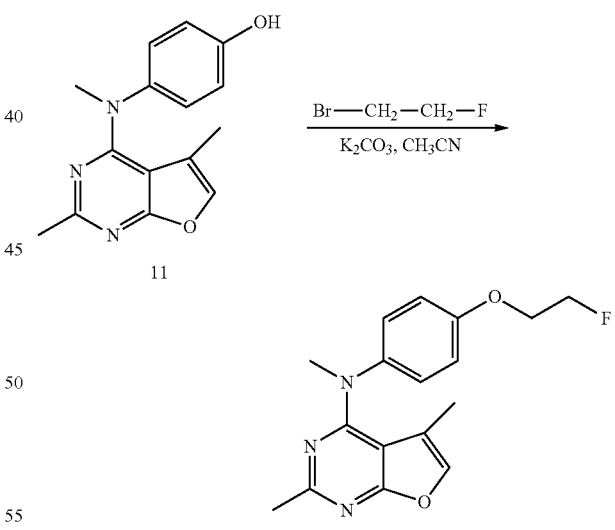

1-Bromo-2-fluoroethane (125 mg, 1 mmol) and potassium carbonate (160 mg, 1.15 mmol) were added to the solution of 11 (54 mg, 0.2 mmol) in dry CH$_3$CN (4 ml). The reaction mixture was heated at 80° C. for overnight. The reaction mixture was cooled to rt, filtered and evaporated under high vacuum. The residue was chromagraphed over silicagel using 2% methanol in CH$_2$Cl$_2$ to give the compound 22 as a pale-yellow solid (50 mg, 80%). 22: $^1$H NMR (400 MHz, CDCl$_3$) δ 8.5 (1H, s), 7.1 (m, 3H); 7.0 (d, 2H), 4.8 (m, 1H), 4.6 (m, 1H), 4.3 (m, 1H), 4.1 (m, 1H), 3.5 (3H, s, CH$_3$), 1.1 (3H, s, CH$_3$); HRMS Calcd for C$_{17}$H$_{19}$FN$_3$O$_2$ (MH+): 316.1454; Found: 316.1462.

Table 4 shows cross selectivity of FEHD-800 which did not exhibit binding to a large panel of brain targets.

TABLE 4

Affinity of FE-HD-800 to brain targets.

| Targets | Affinity (nM) | Targets | Affinity (nM) |
|---|---|---|---|
| 5-HT1A-1E | >10,000 | 5-HT3-7 | >10,000 |
| 5-HT2A-2C | >10,000 | A | >10,000 |
| 5-HT2A-2C | >10,000 | α1A-1C | >10,000 |
| 5-HT3-7 | >10,000 | β1-3 | >10,000 |
| α2A-2C | >10,000 | BZP | >10000 |
| AMPA | >10,000 | CB1, CB2 | >10,000 |
| Ca+ channel | >10,000 | DAT | >10,000 |
| D1-D5 | >10,000 | H1 | 3368 |
| DOR | >10,000 | H3, H4 | >10,000 |
| H2 | >10,000 | GABA | >10,000 |
| HERG | >10,000 | I | >10,000 |
| EP | >10,000 | KA | >10,000 |
| KOR | >10,000 | mGluR | >10,000 |
| M | >10,000 | MOR | >10,000 |
| MDR1 | >10,000 | NK | >10,000 |
| NET | >10,000 | NOP | >10,000 |
| NMDA | >10,000 | Oxytocin | >10,000 |
| NT | >10,000 | PKC | >10,000 |
| PBR | >10,000 | Sigma1 | 832 |
| SERT | >10,000 | Na+ Channel | >10,000 |
| Sigma 2 | 2464 | VMAT 1,2 | >10,000 |
| Smoothened | >10,000 | | |

Radiosynthesis of [$^{18}$]FEHD-800

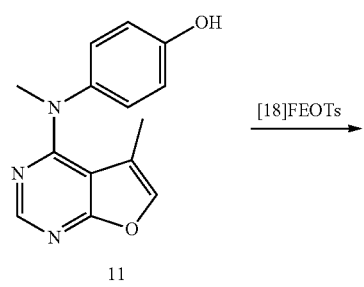

The [$^{18}$F]fluoroethyltosylate is added to a solution of ~2 mg of 11 in 0.25 mL DMSO and heated for 30 minutes at 90° C. The crude product was diluted with 0.25 mL of acetonitrile and was directly injected into a semi preparative RP-HPLC (Phenomenex C18, 10×250 mm, 10) and eluted with acetonitrile: 0.1 M ammonium formate solution (50:50) at a flow rate of 7 mL/min. The precursor eluted after 2-3 minute during the HPLC analysis. The radioproduct fraction with a retention time of 8-9 minutes based on γ-detector was collected, diluted with 50 mL of deionized water, and passed through a C-18 Sep-Pak® cartridge. Reconstitution of the product in 1 mL of absolute ethanol afforded [$^{18}$F]22 (<5% radiochemical yield). The quality control analysis of [$^{18}$F]22 was assessed using an analytical reverse phase Phenomenex ODS HPLC column (250×4.6 mm, 5µ) consisted of 60% acetonitrile, 40% 0.1 M aqueous ammonium formate solution (pH value 6.0-6.5) and a flow rate of 1.5 mL/min and retention time (~6 minute).

Example 12 Alternative Radiosynthesis of [18F]FE-HD-800 (([$^{18}$F]fluoroethy-HD-800; [18F]22)

Since the radiochemical yield of [$^{18}$F]FE-HD-800 was low with the prosthetic labeling approach using [$^{18}$F]FEOTs strategy, we adopted a single step approach for the radiosynthesis of [$^{18}$F]FE-HD-800.

Alternative One Pot Synthesis of [$^{18}$F]22

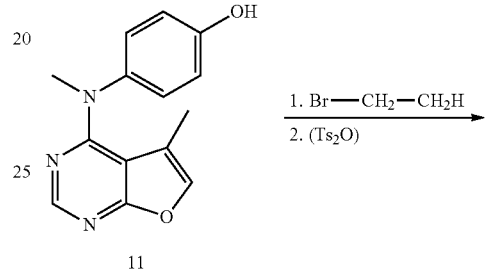

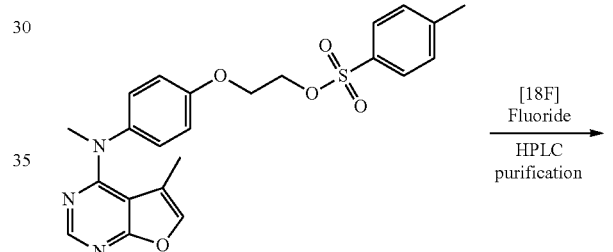

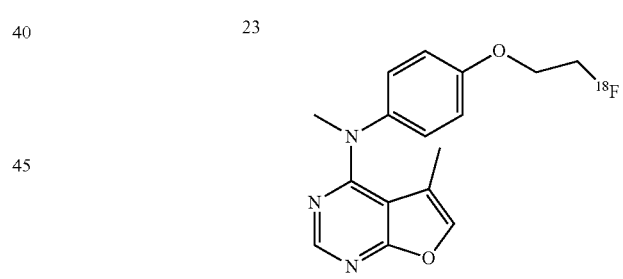

1-Bromo-2-ethanol (100 mg, 0.8 mmol) and potassium carbonate (140 mg, 1 mmol) were added to the solution of 11 (51 mg, 0.2 mmol) in dry DMF (5 ml). The reaction mixture was heated at 120° C. for overnight. The reaction mixture was cooled to RT, diluted with 5 mL water and extracted with ethyl acetate (2×25 mL). The combined ethyl acetate washed water, brine and evaporated under high vacuum. The residue was chromatographed over silicagel using 5% methanol-dichloromethane to afford desired compound as pale-yellow solid (55 mg, 92%) and was used for tosylation reaction.

Tosyl anhydride (100 mg, 0.3 mmol) was added to a solution of 55 mg (0.18 mmol) alcohol, 0.1 mL of trimethylamine in 5 mL dry dichloromethane. The reaction mixture was allowed to stirrer at RT for 4 h. After the complete conversion of compound 20 by TLC, the crude reaction was evaporated under high vacuum. The residue was chromatographed using ethyl acetate-hexane to afford compound 23 as yellow solid (70 mg, 84%).

23: $^1$H NMR (400 MHz, CDCl$_3$) δ 8.5 (1H, s), 7.7 (d, 2H); 7.3 (d, 2H), 7.2 (m, 3H), 6.7 (d, 2H), 4.3 (t, 2H), 4.1 (t, 2H), 3.5 (3H, s, CH$_3$), 2.4 (3H, s, CH$_3$), 1.1 (3H, s, CH$_3$); HRMS Calcd for C$_{25}$H$_{26}$N$_3$O$_4$S (MH+): 464.1642; Found: 464.1644.

Precursor 23 (1-2 mg) in 500 μL of acetonitrile was added to azeotropically dried [$^{18}$F]fluoride. The reaction mixture was allowed to heat 20 minutes at 90° C. The reaction mixture was allowed to cool, diluted with 20 mL water and pass through a C18 Seppack. The Sepack was washed with 1 mL acetonitrile and was injected into a semipreparative HPLC system (Phenomenex ODS (250×10 mm, 10μ) to purify [18F]HD-800. HPLC mobile phase solution consisted of 50% acetonitrile, 50% 0.1 M aqueous ammonium formate solution (pH value 6.0-6.5) with a flow rate of 7.0 mL/min. The product [$^{18}$F]FEHD-800 (R$_t$=~9 min) was collected and diluted with 50 mL deionized water, and passed through C18 SepPak cartridge to trap the radiotracer. Radioactive product was then eluted from the cartridge with absolute ethanol (1.0 mL) and formulated with saline (10% ethanol in saline) (40% radiochemical yield). The quality control analysis[$^{18}$F] FEHD-800 was assessed using an analytical reverse phase Phenomenex ODS HPLC column (250×4.6 mm, 5μ) with mobile phase consisted of 60% acetonitrile, 40% 0.1 M aqueous ammonium formate solution (pH value 6.0-6.5) and a flow rate of 1.5 mL/min and retention time (~6.0 minute).

Example 13 Synthesis and Radiosynthesis of [$^{11}$C]AG488 ([$^{11}$C]25)

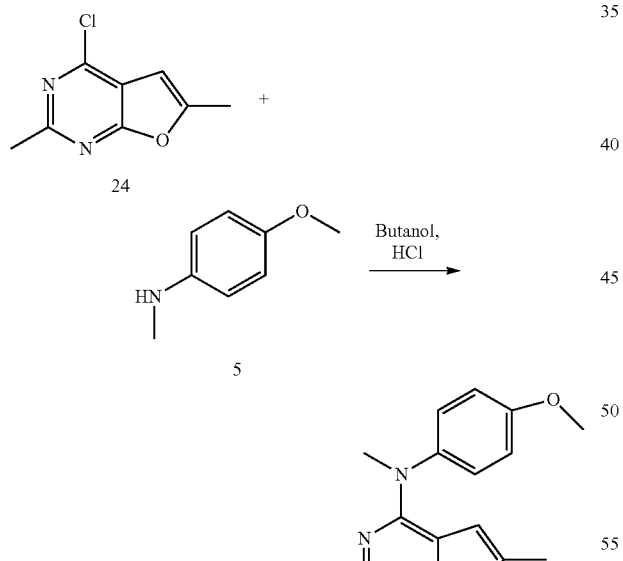

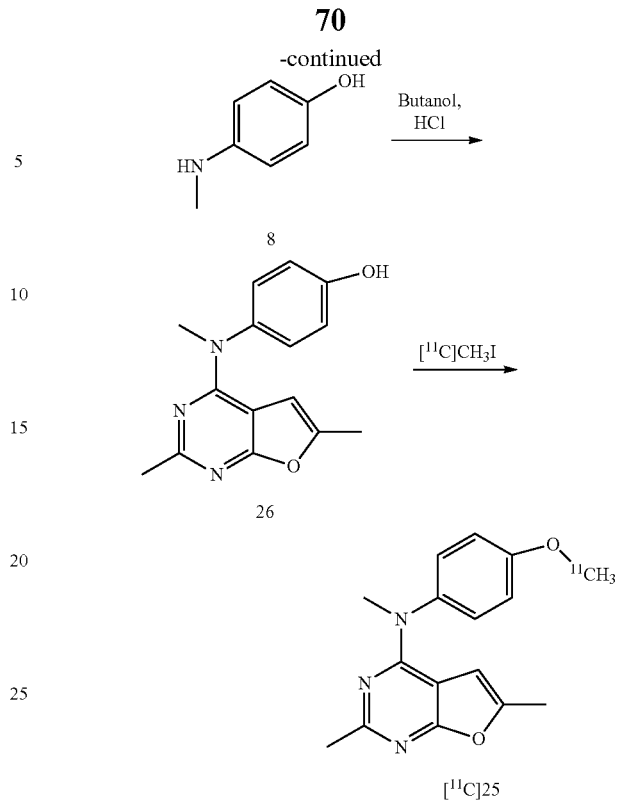

Synthesis of 25

To a solution of 4-chloro-2,6-dimethylfuro[2,3-d]pyrimidine (24, 36 mg, 0.2 mmol) and 4-methoxy-N-methylaniline (5, 42 mg, 0.3 mmol) in 3 mL of butanol was added 2 drops of concentrated HCl and the reaction mixture refluxed to overnight. After the complete conversion of 24 through HPLC, the reaction mixture was allowed to cool, and evaporated under high vacuum. The crude product was chromatographed using methanol-dichloromethane to afford AG-488 (25) as pale yellow solid (40 mg, 72%). Analytical data of compound 25 is identical to the reported product (Zhang et al, Bioorganic Med Chem let. 2014, 22, 3753).

25: $^1$H NMR (400 MHz, CDCl$_3$) δ: 7.2 (2H, d), 7.0 (3H, m), 3.9 (s, 3H, CH$_3$), 3.6 (s, 3H, CH$_3$), 2.7 (s, 3H, CH$_3$), 2.2 (s, 3H, CH$_3$)

Synthesis of 26

To a solution of 4-chloro-2,6-dimethylfuro[2,3-d]pyrimidine (24, 36 mg, 0.2 mmol) and 4- and 4-(methylamino) phenol (7, 40 mg, 0.3 mmol) in 3 mL of butanol was added 2 drops of concentrated HCl and the reaction mixture refluxed to overnight. After the complete conversion of 24 through HPLC, the reaction mixture was allowed to cool, and evaporated under high vacuum. The crude product was chromatographed using methanol-dichloromethane to afford 25 as yellow solid (44 mg, 83%).

26: $^1$H NMR (400 MHz, CDCl$_3$) δ: 7.2 (2H, d), 7.0 (3H, m), 4.6 (1H, b, OH), 3.7 (s, 3H, CH$_3$), 2.7 (s, 3H, CH$_3$), 2.2 (s, 3H, CH$_3$); HRMS (MH+) calculated for: C$_{15}$H$_6$N$_3$O$_2$: 270.1236; Found: 270.1243.

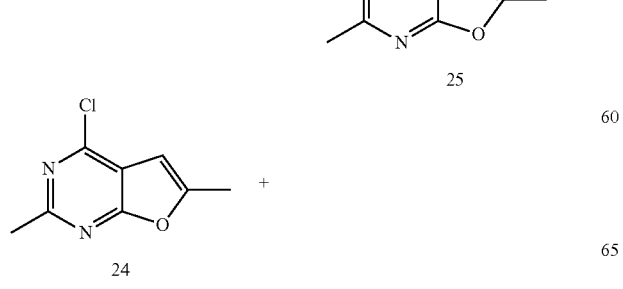

Alternate Synthesis of Compound 26

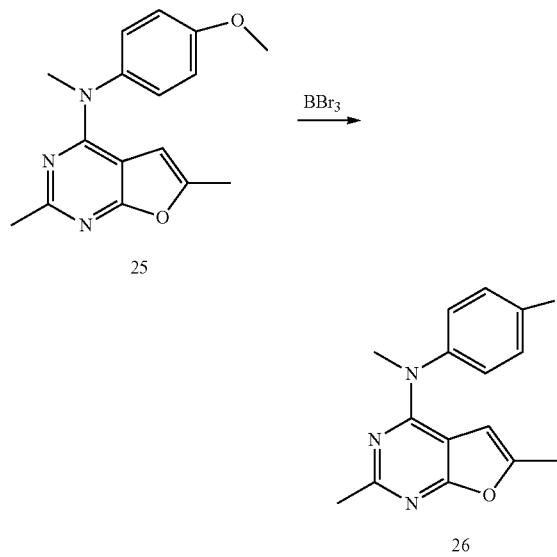

BBr$_3$ (0.4 mL, 1M solution) was added to a solution of 25 (56 mg, 0.2 mmol) in 2 mL anhydrous dichloromethne at 0° C. The solution was stirred at 40° C. for 4 h. An aliquot of reaction mixture was quenched with methanol, performed analytical HPLC and conformed complete conversion of 25. The reaction was allowed to cool, quenched by dropwise addition of methanol (0.5 mL) at 0° C., diluted with water (5 mL), extracted with ethyl acetate containing 5% butanol (3×25 mL). The combined organic extracts were washed saturated NaHCO$_3$, brine, water and dried over anhydrous MgSO$_4$. Solvent was evaporated under reduced pressure to afford crude product, which upon silica gel chromatography with methanol-dichloromathane to provide compound 26 as pale-yellow solid (42 mg, 80%).

Radiosynthesis of [$^{11}$C]AG488 ([$^{11}$C]25)

The precursor 26 (~0.5 mg) was dissolved in 500 μL of DMF in a capped 1 mL V-vial. 10 microL of TBAOH was added and the resultant solution was allowed to stand for 2 minutes. [$^{11}$C]CH$_3$I was transported into the reaction vial over approximately 5 minutes at room temperature. At the end of the trapping, the product mixture was heated for 5 min at 80° C. The reaction mixture was allowed to cool, diluted with 0.5 mL of mobile phase and was directly injected into a semi preparative HPLC Column (Phenomenex ODS (250×10 mm, 10μ, 50:40 acetonitrile and 0.1M ammonium formate, Flow rate: 10 mL/min; λ=254 nM) to purify [$^{11}$C]25. The radioproduct [$^{11}$C]25 (R$_f$=~8 min) was collected and diluted with 100 mL deionized water, and passed through C18 SepPak cartridge to trap the radiotracer. Radioactive product was then eluted from the cartridge with absolute ethanol (1.0 mL) and formulated with saline (10% ethanol in saline). [$^{11}$C]25 purity was assessed using an analytical reverse phase Phenomenex ODS HPLC column (250×4.6 mm, 5μ) using analytical mobile phase (2 mL/min) consisted of 50% acetonitrile and 50% 0.1M aqueous ammonium formate pH 6.0-6.5 solution (R$_f$~5 min, 35% radiochemical yield)

Example 14 Radiosynthesis of [$^{11}$C]WX-132-18B ([$^{11}$C]3)

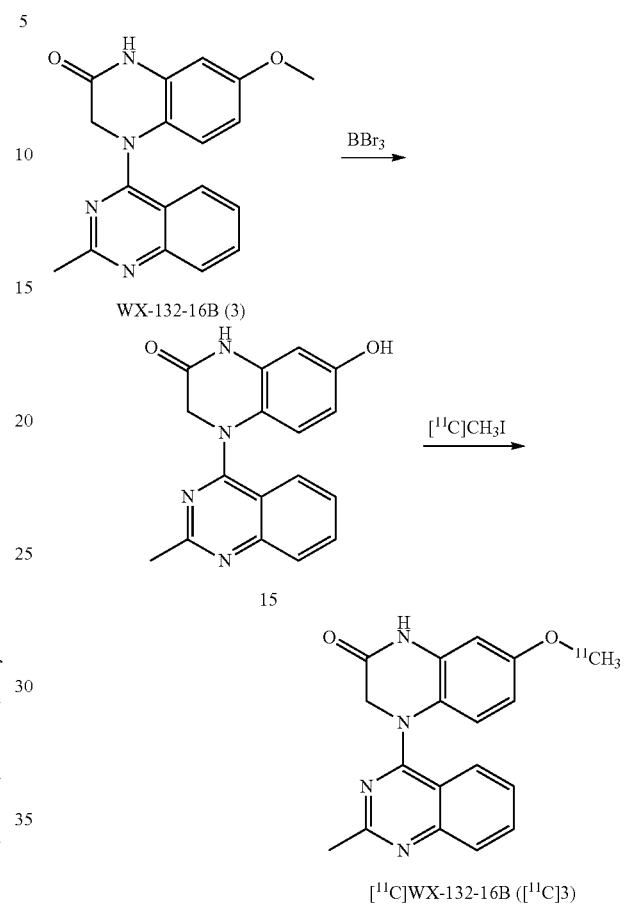

Synthesis of WX-132-18B was achieved based on a reported procedure with minor modification (J. Med. Chem., 2017, 60, 5586). Analytical data are in agreement with previous report (J. Med Chem., 2017, 60, 5586). The desmethyl-WX-132-18B, the radiolabeling precursor was synthesized by demethylation of compound 3 with BBr3.

Synthesis of desmethyl-WX-132-18B (15)

2 mL anhydrous dichloromethane was added to an argon charged reaction vessel containing WX-132-18B (32 mg, 0.1 mmol). 1M solution of BBr3 in dichloromethane (0.3 mL) was added dropwise to it at 0° C. The solution was stirred at 40° C. for 1 h. An aliquot of reaction mixture was quenched with methanol, performed analytical HPLC and conformed complete conversion of WX-132-18B. The reaction was allowed to cool, quenched by dropwise addition of methanol (0.5 mL) at 0° C., diluted with water (5 mL), extracted with ethyl acetate containing 5% butanol (3×25 mL). The combined organic extracts were washed saturated NaHCO$_3$, brine, water and dried over anhydrous MgSO$_4$. Solvent was evaporated under reduced pressure to afford crude product, which upon silica gel chromatography with methanol-dichloromathane to provide compound 15 as pale-yellow solid (24 mg, 80%).

15: $^1$H NMR (400 MHz, CD$_3$OD) δ: 7.8 (2H, m), 7.5 (1H, d), 7.4 (1H, t), 6.5-6.7 (2H, m), 6.3 (1H, m), 4.6 (2H, s, $CH_2$), 2.7 (3H, s, $CH_3$); HRMS (EI+) calculated for: $C_{17}H_{15}N_4O_2$: 307.1195; Found: 307.1195.

Radioynthesis of [$^{11}$C]WX-132-18B ([$^{11}$C]3)

The precursor 15 (~0.5 mg) was dissolved in 500 μL of DMF in a capped 1 mL V-vial. 10 microL of TBAOH was added and the resultant solution was allowed to stand for 2 minutes. [$^{11}$C]$CH_3$I was transported into the reaction vial over approximately 5 minutes at room temperature. At the end of the trapping, the product mixture was heated for 5 min at 80° C. The reaction mixture was allowed to cool, diluted with 0.5 mL of mobile phase and was directly injected into a semi preparative HPLC Column (Phenomenex ODS (250×10 mm, 10μ, 50:50 acetonitrile and 0.1M ammonium formate, Flow rate: 7 mL/min; λ=254 nM) to purify [$^{11}$C]3. The radioproduct [$^{11}$C]3 ($R_t$=~8 min) was collected and diluted with 100 mL deionized water, and passed through C18 SepPak cartridge (WAT036800, Waters, Milford, MA) to trap the radiotracer. Radioactive product was then eluted from the cartridge with absolute ethanol (1.0 mL) and formulated with saline (10% ethanol in saline). [$^{11}$C]3 purity was assessed using an analytical reverse phase Phenomenex ODS HPLC column (250×4.6 mm, 5μ) using analytical mobile phase (1 mL/min) consisted of 50% acetonitrile and 50% 0.1M aqueous ammonium formate pH 6.0-6.5 solution ($R_t$~6 min, 30% radiochemical yield).

Example 15: Synthesis and Radiosynthesis of [$^{11}$C]30 ([$^{11}$C]HD-900)

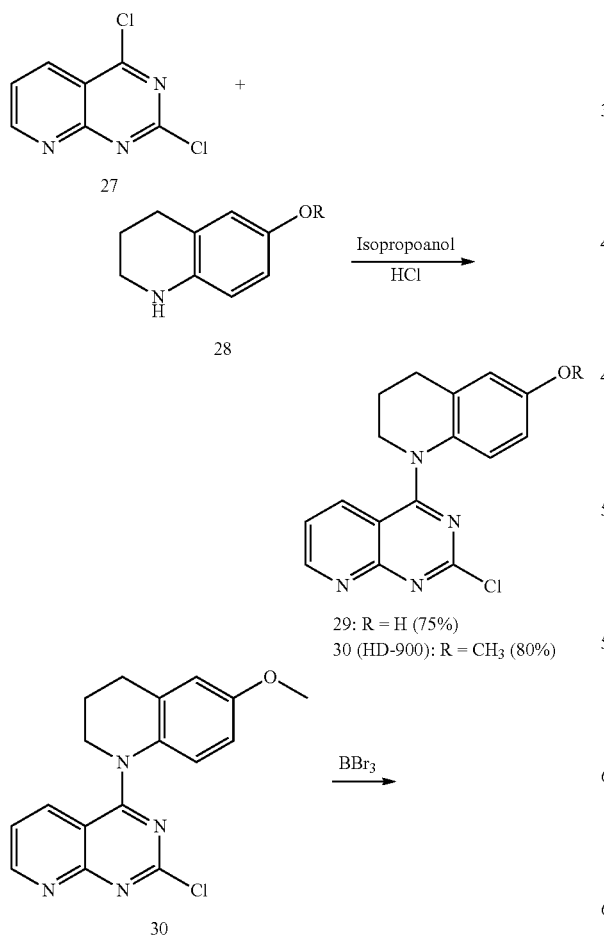

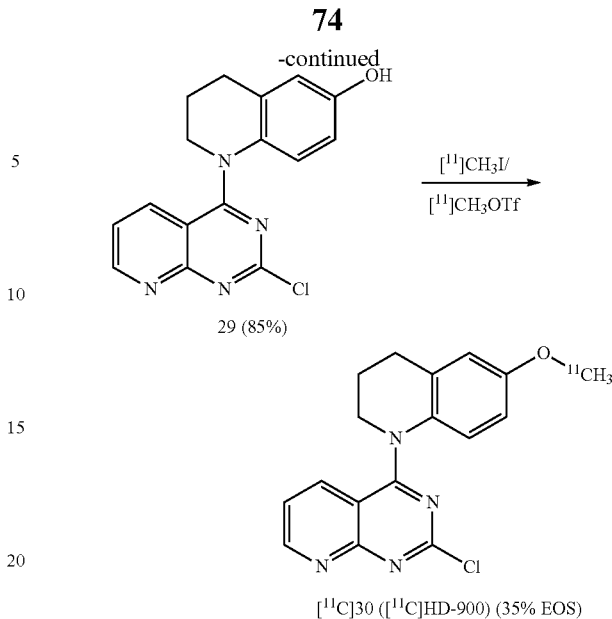

Synthesis of HD-900 (30) and desmethyl-HD-900 (29) has been achieved based on a reported procedure.[26] Alternatively, compound 29 was obtained from the demethylation of compound 30 with BBr3 in 85% yield.

Radioynthesis of [$^{11}$C]HD-900 ([$^{11}$C]30)

The precursor 29 (~0.5 mg) was dissolved in 500 μL of DMF in a capped 1 mL V-vial. 10 microL of TBAOH was added and the resultant solution was allowed to stand for 2 minutes. [$^{11}$C]$CH_3$I was transported into the reaction vial over approximately 5 minutes at room temperature. At the end of the trapping, the product mixture was heated for 5 min at 80° C. The reaction mixture was allowed to cool, diluted with 0.5 mL of mobile phase and was directly injected into a semi preparative HPLC Column (Phenomenex ODS (250×10 mm, 10μ, 50:50 acetonitrile and 0.1M ammonium formate, Flow rate: 7 mL/min; λ=254 nM) to purify [$^{11}$C]30. The radioproduct [$^{11}$C]30 ($R_t$=~8 min) was collected and diluted with 100 mL deionized water, and passed through C18 SepPak cartridge (WAT036800, Waters, Milford, MA) to trap the radiotracer. Radioactive product was then eluted from the cartridge with absolute ethanol (1.0 mL) and formulated with saline (10% ethanol in saline). [$^{11}$C]30 purity was assessed using an analytical reverse phase Phenomenex ODS HPLC column (250×4.6 mm, 5μ) using analytical mobile phase (1 mL/min) consisted of 50% acetonitrile and 50% 0.1M aqueous ammonium formate pH 6.0-6.5 solution ($R_t$~6.5 min, 35% radiochemical yield).

Example 16 Radiosynthesis of [$^{18}$F]31 ([$^{18}$F]FHD-900)

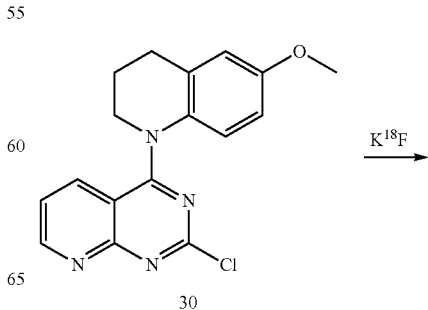

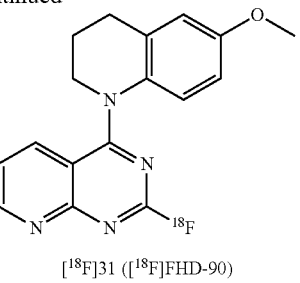

[¹⁸F]31 ([¹⁸F]FHD-90)

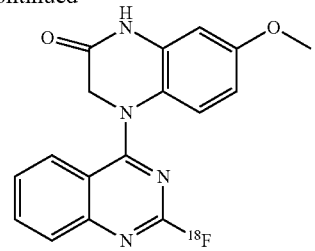

[¹⁸F]35 ([¹⁸F]FHD-910)

The precursor 30 (~2 mg) in 500 µL of DMSO was added to a azeotropically dried [¹⁸F]KF/Kryptofix/K$_2$CO$_3$ mixture in a capped 1 mL V-vial. The reaction mixture was heated at 140° C. for 30 minute, allow to cool and diluted with 20 mL water. The resulting mixture was passed through a C18 SepPak cartridge (WAT036800, Waters, Milford, MA) to trap the radiotracer. The C18 sepack was eluted with 1 mL acetonitrile and was injected into a semi preparative HPLC Column (Phenomenex ODS (250×10 mm, 10µ, 45:55 acetonitrile and 0.1M ammonium formate, Flow rate: 7 mL/min; λ=254 nM) to purify [¹⁸F]31. The radioproduct [¹⁸F]31 (R$_t$=~10 min) was collected and diluted with 100 mL deionized water, and passed through C18 SepPak cartridge to trap the radiotracer. Radioactive product was then eluted from the cartridge with absolute ethanol (1.0 mL) and formulated with saline (10% ethanol in saline). [¹⁸F]31 purity was assessed using an analytical reverse phase Phenomenex ODS HPLC column (250×4.6 mm, 5µ) using analytical mobile phase (1 mL/min) consisted of 50% acetonitrile and 50% 0.1M aqueous ammonium formate pH 6.0-6.5 solution (R$_t$~6 min, 20% radiochemical yield).

Example 17 Radiosynthesis of [¹⁸F]32 ([¹⁸F]FHD-910)

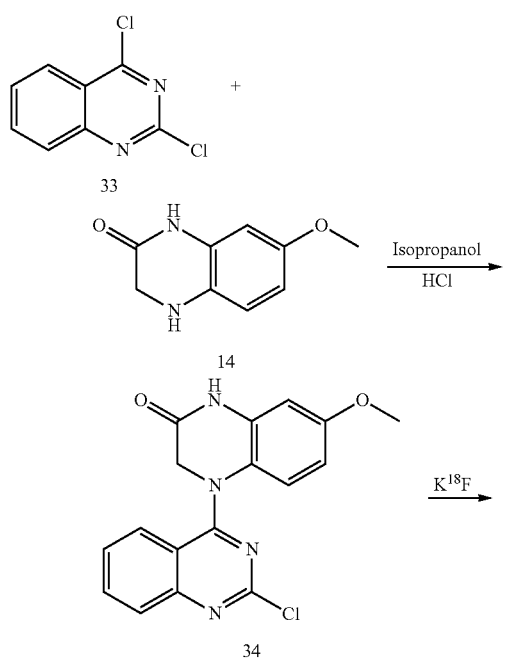

Synthesis of compound 34 is achieved based on a reported procedure.[13,27]

The precursor 34 (~2 mg) in 500 µL of DMSO was added to a azeotropically dried [¹⁸F]KF/Kryptofix/K$_2$CO$_3$ mixture in a capped 1 mL V-vial. The reaction mixture was heated at 140° C. for 30 minute, allow to cool and diluted with 20 mL water. The resulting mixture was passed through a C18 SepPak cartridge (WAT036800, Waters, Milford, MA) to trap the radiotracer. The C18 sepack was eluted with 1 mL acetonitrile and was injected into a semi preparative HPLC Column (Phenomenex ODS (250×10 mm, 10µ, 45:55 acetonitrile and 0.1M ammonium formate, Flow rate: 7 mL/min; λ=254 nM) to purify [¹⁸F]35. The radioproduct [¹⁸F]35 (R=~9 min) was collected and diluted with 100 mL deionized water, and passed through C18 SepPak cartridge to trap the radiotracer. Radioactive product was then eluted from the cartridge with absolute ethanol (1.0 mL) and formulated with saline (10% ethanol in saline). [¹⁸F]31 purity was assessed using an analytical reverse phase Phenomenex ODS HPLC column (250×4.6 mm, 5µ) using analytical mobile phase (1 mL/min) consisted of 45% acetonitrile and 55% 0.1M aqueous ammonium formate pH 6.0-6.5 solution (R$_t$~7 min, 20% radiochemical yield).

Example 18 Radioynthesis of [¹¹C]36

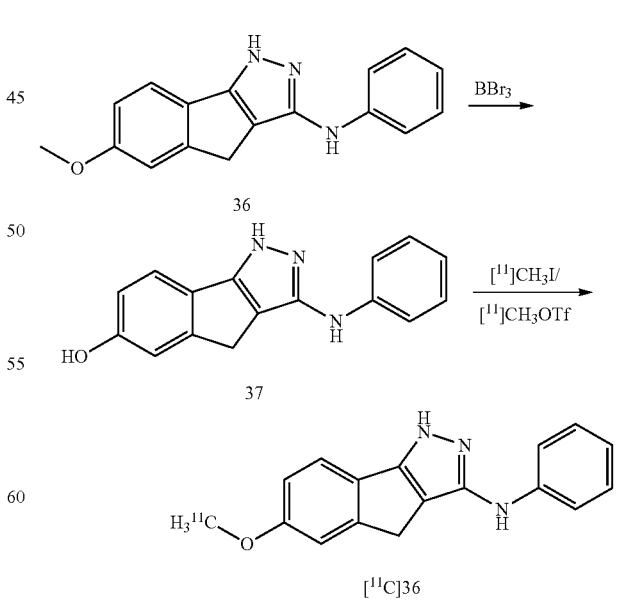

The reference compound 36 was synthesized using a reported procedure.[28] The precursor 37 was obtained by demethylation of compound 36 with BBr3. Radiosynthesis of [¹¹C]36 was performed by reacting 37 (~0.5 mg, in 500 μL of DMF) in a capped 1 mL V-vial with 10 microL of TBAOH and [¹¹C]CH₃I at 80° C. for 5 minutes. The reaction mixture was allowed to cool, diluted with 0.5 mL of mobile phase and was directly injected into a semi-preparative HPLC Column (Phenomenex ODS (250×10 mm, 10 it, 50:50 acetonitrile and 0.1M ammonium formate) to purify [¹¹C]36. The radioproduct [¹¹C]36 was collected and diluted with 100 mL deionized water, and passed through C18 SepPak cartridge (WAT036800, Waters, Milford, MA) to trap the radiotracer. Radioactive product was then eluted from the cartridge with absolute ethanol (1.0 mL) and formulated with saline (10% ethanol in saline). [¹¹C]36 purity was assessed using an analytical reverse phase Phenomenex ODS HPLC column (250×4.6 mm, 5μ) using analytical mobile phase consisted of 50% acetonitrile and 50% 0.1M aqueous ammonium formate pH 6.0-6.5 solution.

Example 19 Radioynthesis of [¹¹C]39 ([¹¹C]GN39482)

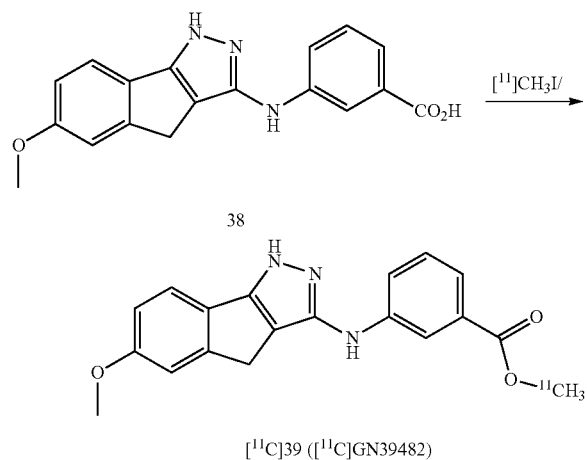

Radiosynthesis of [¹¹C]39 was performed by reacting 38 (~0.5 mg, in 500 μL of DMF) in a capped 1 mL V-vial with 10 microL of NaOH and [¹¹C]CH₃I at 80° C. for 5 minutes. The reaction mixture was allowed to cool, diluted with 0.5 mL of mobile phase and was directly injected into a semi-preparative HPLC Column (Phenomenex ODS (250×10 mm, 10μ, 50:50 acetonitrile and 0.1M ammonium formate) to purify [¹¹C]39. The radioproduct [¹¹C]39 was collected and diluted with 100 mL deionized water, and passed through C18 SepPak cartridge (WAT036800, Waters, Milford, MA) to trap the radiotracer. Radioactive product was then eluted from the cartridge with absolute ethanol (1.0 mL) and formulated with saline (10% ethanol in saline). [¹¹C]39 purity was assessed using an analytical reverse phase Phenomenex ODS HPLC column (250×4.6 mm, 5μ) using analytical mobile phase consisted of 50% acetonitrile and 50% 0.1M aqueous ammonium formate pH 6.0-6.5 solution.

REFERENCES

1. Harada R, Furumoto S, Tago T, Katsutoshi F, Ishiki A, Tomita N, Iwata R, Tashiro M, Arai H, Yanai K, Kudo Y, Okamura N. *Eur J Nucl Med Mol Imaging*. 2016 November; 43(12):2211-2218.
2. Bickel, U. *NeuroRx*. 2005 January; 2(1): 15-26.
3. Jordan, M A and Wilson, L. Nature Reviews *Cancer* 4, 253-265 (April 2004)
4. van der Veldt A A, Lammertsma A A. In vivo imaging as a pharmacodynamic marker. Clin Cancer Res. 2014 May 15; 20(10):2569-77.
5. Pike V W. *Trends Pharmacol Sci*. 2009 August; 30(8): 431-440.
6. Remington: The Science and Practice of Pharmacy, 21st Edition; Lippincott Williams & Wilkins: Philadelphia, PA 2005.
7. "Handbook of Pharmaceutical Salts, Properties, and Use," Stah and Wermuth, Ed.; (Wiley-VCH and VHCA, Zurich, 2002) and Berge et al., *J. Pharm. Sci.* 1977, 66, 1-19.
8. Sirisoma N, Pervin A, Zhang H, Jiang S, Willardsen J A, Anderson M B, Mather G, Pleiman C M, Kasibhatla S, Tseng B, Drewe J, Cai S X. Discovery of N-(4-methoxyphenyl)-N,2-dimethylquinazolin-4-amine, a potent apoptosis inducer and efficacious anticancer agent with high blood brain barrier penetration. *J Med Chem.* 2009 Apr. 23; 52(8):2341-51.
9. Kasibhatla S, Baichwal V, Cai S X, Roth B, Skvortsova I, Skvortsov S, Lukas P, English N M, Sirisoma N, Drewe J, Pervin A, Tseng B, Carlson R O, Pleiman C M. MPC-6827: a small-molecule inhibitor of microtubule formation that is not a substrate for multidrug resistance pumps. *Cancer Res.* 2007 Jun. 15; 67(12):5865-71.
10. Tsimberidou A M, Akerley W, Schabel M C, Hong D S, Uehara C, Chhabra A, Warren T, Mather G G, Evans B A, Woodland D P, Swabb E A, Kurzrock R. Phase I clinical trial of MPC-6827 (Azixa), a microtubule destabilizing agent, in patients with advanced cancer. *Mol Cancer Ther.* 2010 December; 9(12):3410-9.
11. Grossmann K F, Colman H, Akerley W A, Glantz M, Matsuoko Y, Beelen A P, Yu M, De Groot J F, Aiken R D, Olson J J, Evans B A, Jensen R L. Phase I trial of verubulin (MPC-6827) plus carboplatin in patients with relapsed glioblastoma multiforme. *J Neurooncol.* 2012 November; 110(2):257-64.
12. Devambatla R K, Namjoshi O A, Choudhary S, Hamel E, Shaffer C V, Rohena C C, Mooberry S L, Gangjee A. Design, Synthesis, and Preclinical Evaluation of 4-Substituted-5-methyl-furo[2,3-d] pyrimidines as Microtubule Targeting Agents That Are Effective against Multidrug Resistant Cancer Cells. *J Med Chem.* 2016 Jun. 23; 59(12):5752-65.
13. Wang X F, Guan F, Ohkoshi E, Guo W, Wang L, Zhu D Q, Wang S B, Wang L T, Hamel E, Yang D, Li L, Qian K, Morris-Natschke S L, Yuan S, Lee K H, Xie L. Optimization of 4-(N-cycloamino) phenylquinazolines as a novel class of tubulin-polymerization inhibitors targeting the colchicine site. *J Med Chem.* 2014 Feb. 27; 57(4):1390-402.
14. Guan F, Ding R, Zhang Q, Chen W, Li F, Long L, Li W, Li L, Yang D, Xie L, Yuan S, Wang L1. WX-132-18B, a novel microtubule inhibitor, exhibits promising anti-tumor effects, Oncotarget, 2017 May 9. doi: 10.18632/oncotarget.17710.
15. Wilson A A, Jin L, Garcia A, DaSilva J N and Houle S, An admonition when measuring the lipophilicity of radiotracers using counting techniques. *Applied Radiation and Isotopes,* 2001, 54: 203-208.
16. Kitange G J, Carlson B L, Mladek A C, Decker P A, Schroeder M A, Wu W, Grogan P T, Giannini C, Ballman K V, Buckner J C, James C D, Sarkaria J N. Evaluation of mgmt promoter methylation status and correlation with temozolomide response in orthotopic glioblastoma xenograft model. *J Neurooncol.* 2009; 92:23-31
17. Sarkaria J N, Carlson B L, Schroeder M A, Grogan P, Brown P D, Giannini C, Ballman K V, Kitange G J, Guha A, Pandita A, James C D. Use of an orthotopic xenograft model for assessing the effect of epidermal growth factor receptor amplification on glioblastoma radiation response. *Clin Cancer Res.* 2006; 12:2264-2271
18. Sarkaria J N, Yang L, Grogan P T, Kitange G J, Carlson B L, Schroeder M A, Galanis E, Giannini C, Wu W, Dinca E B, James C D. Identification of molecular characteristics correlated with glioblastoma sensitivity to egfr kinase inhibition through use of an intracranial xenograft test panel. *Mol Cancer Ther.* 2007; 6:1167-1174.
19. Fournier A E, McKerracher L. Expression of specific tubulin isotypes increases during regeneration of injured CNS neurons, but not after the application of brain-derived neurotrophic factor (BDNF). *J Neurosci.* 1997 Jun. 15; 17(12):4623-32.
20. Lockman J. W, Klimova Y, Anderson M. B., Willardsen J. A. Synthesis of Substituted Quinazolines: Application to the Synthesis of Verubulin. *Synthetic Communications*, 2012, 42 (12), 1715-1723.
21. Kumar J S D, Solingapuram Sai K K, Prabhakaran J, Dileep H, Mintz A, Mann J J. Radiosynthesis and In vivo evaluation of [11C]MPC-6827, the first brain penetrant microtubule PET ligand, J. Med. Chem. 2018, 61(5): 2118-2123.
22. Solingapuram Sai K K, Prabhakaran J, Oufkir H R, Ramanathan G, Whitlow C T, Dileep H, Mann J J, Mintz A, Kumar J S D. Radiosynthesis and in vivo evaluation of [$^{11}$C]MPC-6827, the first brain penetrant microtubule PET ligand, SNM 2018.
23. Kumar J S D, Solingapuram Sai K K, Prabhakaran J, Oufkir H R, Ramanathan G, Whitlow C T, Dileep H, Mintz A, Mann J J, Radiosynthesis and in vivo evaluation of [$^{11}$C]MPC-6827, the first brain penetrant microtubule PET ligand, NRM 2018.
24. Solingapuram Sai K K, Prabhakaran J, Dileep H, Rideout S, Oufkir H R, Ramanathan G, Mintz A, Mann J J, Kumar J S D. Development of [$^{11}$C]HD-800, a high affinity PET tracer for imaging microtubule, SNM 2018.
25. Solingapuram Sai K K, Prabhakaran J, Ramanathan G, Rideout S, Whitlow C, Mintz A, Mann J J, Kumar J S D, Radiosynthesis and evaluation of [$^{11}$C]HD-800, a high affinity brain penetrant PET tracer for imaging microtubules, ACS Medicinal Chemistry Letters, 2018, 9 (5), 452-456.
26. Banerjee S, Arnst K E, Wang Y, Kumar G, Deng S, Yang L, Li G B, Yang J, White S W, Li W, Miller D D. Heterocyclic-Fused Pyrimidines as Novel Tubulin Polymerization Inhibitors Targeting the Colchicine Binding Site: Structural Basis and Antitumor Efficacy. *J Med Chem.* 2018; 61(4):1704-1718.
27. Cui M T, Jiang L, Goto M, Hsu P L, Li L, Zhang Q, Wei L, Yuan S J, Hamel E, Morris-Natschke S L, Lee K H, Xie L. In Vivo and Mechanistic Studies on Antitumor Lead 7-Methoxy-4-(2-methylquinazolin-4-yl)-3,4-dihydroquinoxalin-2(1H)-one and Its Modification as a Novel Class of Tubulin-Binding Tumor-Vascular Disrupting Agents. J Med Chem. 2017 Jul. 13; 60(13):5586-5598
28. Minegishi M, Futamura Y, Fukashiro S, Muroi M, Kawatani M, Osada H, Nakamura H. Methyl 3-((6-Methoxy-1,4-dihydroindeno[1,2-c]pyrazol-3-yl)amino) benzoate (GN39482) as a Tubulin Polymerization Inhibitor Identified by MorphoBase and ChemProteoBase Profiling Methods. J. Med. Chem. 2015, 58, 4230-4241

The scope of the present disclosure is not limited by what has been specifically shown and described hereinabove. Numerous references, including patents and various publications, are cited and discussed in the description of this invention. The citation and discussion of such references is provided merely to clarify the description of the present disclosure and is not an admission that any reference is prior art to the invention described herein. All references cited and discussed in this specification are incorporated herein by reference in their entirety. Variations, modifications and other implementations of what is described herein will occur to those of ordinary skill m the art without departing from the spirit and scope of the invention. While certain embodiments of the present disclosure have been shown and described, it will be obvious to those skilled in the art that changes and modifications may be made without departing from the spirit and scope of the invention. The matter set forth in the foregoing description and accompanying drawings is offered by way of illustration only and not as a limitation. The actual scope of the invention is intended to be defined in the following claims.

What is claimed is:

1. A method for imaging or detecting microtubules in a subject, the method comprising administering to the subject a positron emission tomography (PET) radioligand, wherein the PET radioligand is:

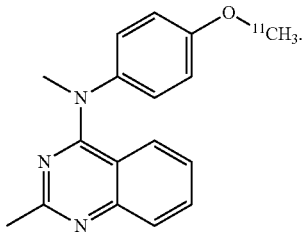

2. The method of claim 1, for imaging microtubules in the brain or spinal cord of the subject.

3. A method for imaging or detecting microtubules in a subject, the method comprising administering to the subject a positron emission tomography (PET) radioligand, p1 wherein the PET radioligand is:

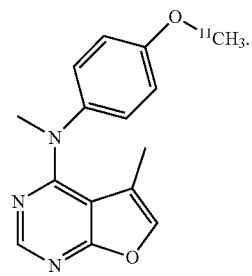

4. The method of claim 3, for imaging microtubules in the brain or spinal cord of the subject.

* * * * *